US008186555B2

(12) United States Patent
Shelton, IV et al.

(10) Patent No.: US 8,186,555 B2
(45) Date of Patent: May 29, 2012

(54) MOTOR-DRIVEN SURGICAL CUTTING AND FASTENING INSTRUMENT WITH MECHANICAL CLOSURE SYSTEM

(75) Inventors: Frederick E. Shelton, IV, New Vienna, OH (US); Christoph L. Gillum, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1231 days.

(21) Appl. No.: 11/344,024

(22) Filed: Jan. 31, 2006

(65) Prior Publication Data
US 2007/0175953 A1    Aug. 2, 2007

(51) Int. Cl.
*A61B 17/072* (2006.01)
(52) U.S. Cl. .............. 227/176.1; 227/19; 227/175.1
(58) Field of Classification Search ........... 227/175.1, 227/176.1, 19, 180.1; 606/1, 51, 52, 139, 606/142, 205, 219
See application file for complete search history.

(56) References Cited

U.S. PATENT DOCUMENTS

| 66,052 A | 6/1867 | Smith |
| 2,037,727 A | 4/1936 | La Chapelle |
| 2,214,870 A | 9/1940 | West |
| 2,441,096 A | 5/1948 | Happe |
| 2,526,902 A | 10/1950 | Rublee |
| 2,804,848 A | 9/1957 | O'Farrell et al. |
| 2,808,482 A | 10/1957 | Zanichkowsky et al. |
| 2,853,074 A | 9/1958 | Olson |
| 3,032,769 A | 5/1962 | Palmer |
| 3,075,062 A | 1/1963 | Iaccarino |
| 3,078,465 A | 2/1963 | Bobrov |
| 3,266,494 A | 8/1966 | Brownrigg et al. |
| 3,269,630 A | 8/1966 | Fleischer |
| 3,357,296 A | 12/1967 | Lefever |
| 3,490,675 A | 1/1970 | Green et al. |
| 3,551,987 A | 1/1971 | Wilkinson |
| 3,598,943 A | 8/1971 | Barrett |
| 3,643,851 A | 2/1972 | Green et al. |

(Continued)

FOREIGN PATENT DOCUMENTS

| CA | 2458946 A1 | 3/2003 |
| CA | 2512960 A1 | 1/2006 |

(Continued)

OTHER PUBLICATIONS

U.S. Appl. No. 11/807,693, filed May 30, 2007.

(Continued)

*Primary Examiner* — Rinaldi Rada
*Assistant Examiner* — Nathaniel Chukwurah

(57) ABSTRACT

A surgical cutting and fastening instrument is disclosed. According to various embodiments, the instrument includes an end effector comprising an elongate channel, a clamping member pivotably connected to the channel, and a moveable cutting instrument for traversing the channel to cut an object clamped in the end effector by the clamping member when the clamping member is in a clamped position. The instrument may also comprise a main drive shaft assembly for actuating the cutting instrument in the end effector, a gear drive train connected to the main drive shaft assembly, and a motor for actuating the gear drive train. The instrument may also includes a closure trigger and a firing trigger, separate from the closure trigger, for actuating the motor when the firing trigger is retracted. Also, the instrument may comprise a mechanical closure system connected to the closure trigger and to the clamping member for causing the clamping member to pivot to the clamped position when the closure trigger is retracted.

22 Claims, 39 Drawing Sheets

U.S. PATENT DOCUMENTS

| | | |
|---|---|---|
| 3,662,939 A | 5/1972 | Bryan |
| 3,717,294 A | 2/1973 | Green |
| 3,734,207 A | 5/1973 | Fishbein |
| 3,751,902 A | 8/1973 | Kingsbury et al. |
| 3,819,100 A | 6/1974 | Noiles et al. |
| 3,821,919 A | 7/1974 | Knohl |
| 3,892,228 A | 7/1975 | Mitsui |
| 3,894,174 A | 7/1975 | Cartun |
| 3,940,844 A | 3/1976 | Colby et al. |
| 4,129,059 A | 12/1978 | Van Eck |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,415,112 A | 11/1983 | Green |
| 4,428,376 A | 1/1984 | Mericle |
| 4,429,695 A | 2/1984 | Green |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,892,244 A | 1/1990 | Fox et al. |
| 4,915,100 A | 4/1990 | Green |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A * | 10/1991 | Muller ............................ 606/83 |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,156,614 A | 10/1992 | Green et al. |
| 5,158,567 A | 10/1992 | Green |
| 5,163,598 A | 11/1992 | Peters et al. |
| 5,171,247 A | 12/1992 | Hughett et al. |
| 5,171,249 A | 12/1992 | Stefanchik et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |

| | | | | | |
|---|---|---|---|---|---|
| 5,236,440 A | 8/1993 | Hlavacek | 5,421,829 A | 6/1995 | Olichney et al. |
| 5,242,457 A | 9/1993 | Akopov et al. | 5,422,567 A | 6/1995 | Matsunaga |
| 5,244,462 A | 9/1993 | Delahuerga et al. | 5,423,809 A | 6/1995 | Klicek |
| 5,246,156 A | 9/1993 | Rothfuss et al. | 5,425,745 A | 6/1995 | Green et al. |
| 5,246,443 A | 9/1993 | Mai | 5,431,322 A | 7/1995 | Green et al. |
| 5,253,793 A | 10/1993 | Green et al. | 5,431,668 A | 7/1995 | Burbank, III et al. |
| 5,258,009 A | 11/1993 | Conners | 5,433,721 A | 7/1995 | Hooven et al. |
| 5,259,366 A | 11/1993 | Reydel et al. | 5,438,302 A | 8/1995 | Goble |
| 5,260,637 A | 11/1993 | Pizzi | 5,441,193 A | 8/1995 | Gravener |
| 5,263,629 A | 11/1993 | Trumbull et al. | 5,441,494 A | 8/1995 | Ortiz |
| 5,263,973 A | 11/1993 | Cook | 5,445,304 A | 8/1995 | Plyley et al. |
| 5,268,622 A | 12/1993 | Philipp | 5,445,644 A | 8/1995 | Pietrafitta et al. |
| 5,271,543 A | 12/1993 | Grant et al. | 5,447,417 A | 9/1995 | Kuhl et al. |
| 5,271,544 A | 12/1993 | Fox et al. | 5,447,513 A | 9/1995 | Davison et al. |
| RE34,519 E | 1/1994 | Fox et al. | 5,449,355 A | 9/1995 | Rhum et al. |
| 5,275,323 A | 1/1994 | Schulze et al. | 5,449,365 A | 9/1995 | Green et al. |
| 5,275,608 A | 1/1994 | Forman et al. | 5,452,836 A | 9/1995 | Huitema et al. |
| 5,281,216 A | 1/1994 | Klicek | 5,454,827 A | 10/1995 | Aust et al. |
| 5,282,806 A | 2/1994 | Haber et al. | 5,456,401 A | 10/1995 | Green et al. |
| 5,282,829 A | 2/1994 | Hermes | 5,462,215 A | 10/1995 | Viola et al. |
| 5,297,714 A | 3/1994 | Kramer | 5,465,894 A | 11/1995 | Clark et al. |
| 5,304,204 A | 4/1994 | Bregen | 5,465,895 A | 11/1995 | Knodel et al. |
| 5,307,976 A | 5/1994 | Olson et al. | 5,465,896 A | 11/1995 | Allen et al. |
| 5,309,927 A | 5/1994 | Welch | 5,466,020 A | 11/1995 | Page et al. |
| 5,312,023 A | 5/1994 | Green et al. | 5,467,911 A * | 11/1995 | Tsuruta et al. ............ 227/175.1 |
| 5,312,329 A | 5/1994 | Beaty et al. | 5,470,006 A | 11/1995 | Rodak |
| 5,314,424 A | 5/1994 | Nicholas | 5,470,007 A | 11/1995 | Plyley et al. |
| 5,318,221 A | 6/1994 | Green et al. | 5,472,132 A | 12/1995 | Savage et al. |
| 5,330,502 A | 7/1994 | Hassler et al. | 5,472,442 A | 12/1995 | Klicek |
| 5,332,142 A | 7/1994 | Robinson et al. | 5,473,204 A | 12/1995 | Temple |
| 5,333,422 A | 8/1994 | Warren et al. | 5,474,057 A | 12/1995 | Makower et al. |
| 5,334,183 A | 8/1994 | Wuchinich | 5,474,566 A | 12/1995 | Alesi et al. |
| 5,339,799 A | 8/1994 | Kami et al. | 5,476,479 A | 12/1995 | Green et al. |
| 5,341,724 A | 8/1994 | Vatel | 5,478,003 A | 12/1995 | Green et al. |
| 5,342,395 A | 8/1994 | Jarrett et al. | 5,478,354 A | 12/1995 | Tovey et al. |
| 5,342,396 A | 8/1994 | Cook | 5,480,089 A | 1/1996 | Blewett |
| 5,344,060 A | 9/1994 | Gravener et al. | 5,480,409 A * | 1/1996 | Riza ............................. 606/205 |
| 5,350,400 A | 9/1994 | Esposito et al. | 5,482,197 A | 1/1996 | Green et al. |
| 5,352,235 A | 10/1994 | Koros et al. | 5,484,095 A | 1/1996 | Green et al. |
| 5,352,238 A | 10/1994 | Green et al. | 5,484,398 A | 1/1996 | Stoddard |
| 5,354,303 A | 10/1994 | Spaeth et al. | 5,484,451 A | 1/1996 | Akopov et al. |
| 5,356,006 A | 10/1994 | Alpern et al. | 5,485,947 A | 1/1996 | Olson et al. |
| 5,358,510 A | 10/1994 | Luscombe et al. | 5,485,952 A | 1/1996 | Fontayne |
| 5,359,231 A | 10/1994 | Flowers et al. | 5,487,499 A | 1/1996 | Sorrentino et al. |
| D352,780 S | 11/1994 | Glaeser et al. | 5,487,500 A | 1/1996 | Knodel et al. |
| 5,360,428 A | 11/1994 | Hutchinson, Jr. | 5,489,058 A | 2/1996 | Plyley et al. |
| 5,364,003 A | 11/1994 | Williamson, IV | 5,489,256 A | 2/1996 | Adair |
| 5,366,134 A | 11/1994 | Green et al. | 5,496,312 A | 3/1996 | Klicek |
| 5,366,479 A | 11/1994 | McGarry et al. | 5,496,317 A | 3/1996 | Goble et al. |
| 5,370,645 A | 12/1994 | Klicek et al. | 5,503,320 A | 4/1996 | Webster et al. |
| 5,372,596 A | 12/1994 | Klicek et al. | 5,503,635 A | 4/1996 | Sauer et al. |
| 5,372,602 A | 12/1994 | Burke | 5,503,638 A | 4/1996 | Cooper et al. |
| 5,374,277 A | 12/1994 | Hassler | 5,505,363 A | 4/1996 | Green et al. |
| 5,379,933 A | 1/1995 | Green et al. | 5,509,596 A | 4/1996 | Green et al. |
| 5,381,782 A | 1/1995 | DeLaRama et al. | 5,509,916 A | 4/1996 | Taylor |
| 5,382,247 A | 1/1995 | Cimino et al. | 5,511,564 A | 4/1996 | Wilk |
| 5,383,880 A | 1/1995 | Hooven | 5,514,129 A | 5/1996 | Smith |
| 5,383,881 A | 1/1995 | Green et al. | 5,514,157 A | 5/1996 | Nicholas et al. |
| 5,383,888 A | 1/1995 | Zvenyatsky et al. | 5,518,163 A | 5/1996 | Hooven |
| 5,383,895 A | 1/1995 | Holmes et al. | 5,518,164 A | 5/1996 | Hooven |
| 5,389,098 A | 2/1995 | Tsuruta et al. | 5,520,700 A | 5/1996 | Beyar et al. |
| 5,391,180 A | 2/1995 | Tovey et al. | 5,522,817 A | 6/1996 | Sander et al. |
| 5,392,979 A | 2/1995 | Green et al. | 5,527,320 A | 6/1996 | Carruthers et al. |
| 5,395,030 A | 3/1995 | Kuramoto et al. | 5,529,235 A | 6/1996 | Boiarski et al. |
| 5,395,033 A | 3/1995 | Byrne et al. | D372,086 S | 7/1996 | Grasso et al. |
| 5,395,312 A | 3/1995 | Desai | 5,531,744 A | 7/1996 | Nardella et al. |
| 5,397,046 A | 3/1995 | Savage et al. | 5,533,521 A | 7/1996 | Granger |
| 5,397,324 A | 3/1995 | Carroll et al. | 5,533,581 A | 7/1996 | Barth et al. |
| 5,403,312 A | 4/1995 | Yates et al. | 5,533,661 A | 7/1996 | Main et al. |
| 5,405,072 A | 4/1995 | Zlock et al. | 5,535,934 A | 7/1996 | Boiarski et al. |
| 5,405,344 A | 4/1995 | Williamson et al. | 5,535,935 A | 7/1996 | Vidal et al. |
| 5,409,498 A | 4/1995 | Braddock et al. | 5,535,937 A | 7/1996 | Boiarski et al. |
| 5,411,508 A | 5/1995 | Bessler et al. | 5,540,375 A | 7/1996 | Bolanos et al. |
| 5,413,267 A | 5/1995 | Solyntjes et al. | 5,541,376 A | 7/1996 | Ladtkow et al. |
| 5,413,268 A | 5/1995 | Green et al. | 5,542,594 A | 8/1996 | McKean et al. |
| 5,413,272 A | 5/1995 | Green et al. | 5,543,119 A | 8/1996 | Sutter et al. |
| 5,415,334 A | 5/1995 | Williamson, IV et al. | 5,547,117 A | 8/1996 | Hamblin et al. |
| 5,415,335 A | 5/1995 | Knodell, Jr. | 5,549,628 A | 8/1996 | Cooper et al. |
| 5,417,361 A | 5/1995 | Williamson, IV | 5,549,637 A | 8/1996 | Crainich |

| | | | | | |
|---|---|---|---|---|---|
| 5,553,675 A | 9/1996 | Pitzen et al. | 5,667,517 A | 9/1997 | Hooven |
| 5,553,765 A | 9/1996 | Knodel et al. | 5,667,527 A | 9/1997 | Cook |
| 5,554,169 A | 9/1996 | Green et al. | 5,669,544 A | 9/1997 | Schulze et al. |
| 5,556,416 A | 9/1996 | Clark et al. | 5,669,904 A | 9/1997 | Platt, Jr. et al. |
| 5,558,665 A | 9/1996 | Kieturakis | 5,669,907 A | 9/1997 | Platt, Jr. et al. |
| 5,558,671 A | 9/1996 | Yates | 5,669,918 A | 9/1997 | Balazs et al. |
| 5,560,530 A | 10/1996 | Bolanos et al. | 5,673,840 A | 10/1997 | Schulze et al. |
| 5,560,532 A | 10/1996 | DeFonzo et al. | 5,673,841 A | 10/1997 | Schulze et al. |
| 5,562,239 A | 10/1996 | Boiarski et al. | 5,673,842 A | 10/1997 | Bittner et al. |
| 5,562,241 A | 10/1996 | Knodel et al. | 5,678,748 A | 10/1997 | Plyley et al. |
| 5,562,682 A | 10/1996 | Oberlin et al. | 5,680,981 A | 10/1997 | Mililli et al. |
| 5,562,701 A | 10/1996 | Huitema et al. | 5,680,982 A | 10/1997 | Schulze et al. |
| 5,562,702 A | 10/1996 | Huitema et al. | 5,680,983 A | 10/1997 | Plyley et al. |
| 5,564,615 A | 10/1996 | Bishop et al. | 5,683,349 A | 11/1997 | Makower et al. |
| 5,571,090 A | 11/1996 | Sherts | 5,685,474 A | 11/1997 | Seeber |
| 5,571,100 A | 11/1996 | Goble et al. | 5,688,270 A | 11/1997 | Yates et al. |
| 5,571,116 A | 11/1996 | Bolanos et al. | 5,692,668 A | 12/1997 | Schulze et al. |
| 5,573,543 A | 11/1996 | Akopov et al. | 5,693,042 A | 12/1997 | Boiarski et al. |
| 5,574,431 A | 11/1996 | McKeown et al. | 5,693,051 A | 12/1997 | Schulze et al. |
| 5,575,789 A | 11/1996 | Bell et al. | 5,695,494 A | 12/1997 | Becker |
| 5,575,803 A | 11/1996 | Cooper et al. | 5,695,504 A | 12/1997 | Gifford, III et al. |
| 5,577,654 A | 11/1996 | Bishop | 5,697,943 A | 12/1997 | Sauer et al. |
| 5,579,978 A | 12/1996 | Green et al. | 5,700,270 A | 12/1997 | Peyser et al. |
| 5,580,067 A | 12/1996 | Hamblin et al. | 5,702,387 A | 12/1997 | Arts et al. |
| 5,582,611 A | 12/1996 | Tsuruta et al. | 5,702,408 A | 12/1997 | Wales et al. |
| 5,582,617 A | 12/1996 | Klieman et al. | 5,702,409 A | 12/1997 | Rayburn et al. |
| 5,584,425 A | 12/1996 | Savage et al. | 5,704,087 A | 1/1998 | Strub |
| 5,586,711 A | 12/1996 | Plyley et al. | 5,704,534 A | 1/1998 | Huitema et al. |
| 5,588,579 A | 12/1996 | Schnut et al. | 5,706,997 A | 1/1998 | Green et al. |
| 5,588,580 A | 12/1996 | Paul et al. | 5,706,998 A | 1/1998 | Plyley et al. |
| 5,588,581 A | 12/1996 | Conlon et al. | 5,707,392 A | 1/1998 | Kortenbach |
| 5,591,170 A * | 1/1997 | Spievack et al. ............... 606/82 | 5,709,334 A | 1/1998 | Sorrentino et al. |
| 5,591,187 A | 1/1997 | Dekel | 5,709,680 A | 1/1998 | Yates et al. |
| 5,597,107 A | 1/1997 | Knodel et al. | 5,711,472 A | 1/1998 | Bryan |
| 5,599,151 A | 2/1997 | Daum et al. | 5,713,128 A | 2/1998 | Schrenk et al. |
| 5,599,344 A | 2/1997 | Paterson | 5,713,505 A | 2/1998 | Huitema |
| 5,599,350 A | 2/1997 | Schulze et al. | 5,713,895 A | 2/1998 | Lontine et al. |
| 5,601,224 A | 2/1997 | Bishop et al. | 5,715,987 A | 2/1998 | Kelley et al. |
| 5,603,443 A | 2/1997 | Clark et al. | 5,715,988 A | 2/1998 | Palmer |
| 5,605,272 A | 2/1997 | Witt et al. | 5,716,366 A | 2/1998 | Yates |
| 5,605,273 A | 2/1997 | Hamblin et al. | 5,718,359 A | 2/1998 | Palmer et al. |
| 5,607,094 A | 3/1997 | Clark et al. | 5,718,360 A | 2/1998 | Green et al. |
| 5,607,095 A | 3/1997 | Smith et al. | 5,718,548 A | 2/1998 | Cotellessa |
| 5,607,450 A | 3/1997 | Zvenyatsky et al. | 5,720,744 A | 2/1998 | Eggleston et al. |
| 5,609,285 A | 3/1997 | Grant et al. | D393,067 S | 3/1998 | Geary et al. |
| 5,611,709 A | 3/1997 | McAnulty | 5,725,536 A | 3/1998 | Oberlin et al. |
| 5,613,966 A | 3/1997 | Makower et al. | 5,725,554 A | 3/1998 | Simon et al. |
| 5,618,294 A | 4/1997 | Aust et al. | 5,728,121 A | 3/1998 | Bimbo et al. |
| 5,618,303 A | 4/1997 | Marlow et al. | 5,730,758 A | 3/1998 | Allgeyer |
| 5,620,289 A | 4/1997 | Curry | 5,732,871 A | 3/1998 | Clark et al. |
| 5,624,452 A | 4/1997 | Yates | 5,732,872 A | 3/1998 | Bolduc et al. |
| 5,626,587 A | 5/1997 | Bishop et al. | 5,735,445 A | 4/1998 | Vidal et al. |
| 5,628,446 A | 5/1997 | Geiste et al. | 5,735,848 A | 4/1998 | Yates et al. |
| 5,628,743 A | 5/1997 | Cimino | 5,735,874 A | 4/1998 | Measamer et al. |
| 5,630,539 A | 5/1997 | Plyley et al. | 5,738,474 A | 4/1998 | Blewett |
| 5,630,540 A | 5/1997 | Blewett | 5,738,648 A | 4/1998 | Lands et al. |
| 5,630,782 A | 5/1997 | Adair | 5,743,456 A | 4/1998 | Jones et al. |
| 5,632,432 A | 5/1997 | Schulze et al. | 5,747,953 A | 5/1998 | Philipp |
| 5,632,433 A | 5/1997 | Grant et al. | 5,749,889 A | 5/1998 | Bacich et al. |
| 5,634,584 A | 6/1997 | Okorocha et al. | 5,749,893 A | 5/1998 | Vidal et al. |
| 5,636,779 A | 6/1997 | Palmer | 5,752,644 A | 5/1998 | Bolanos et al. |
| 5,636,780 A | 6/1997 | Green et al. | 5,752,965 A | 5/1998 | Francis et al. |
| 5,639,008 A | 6/1997 | Gallagher et al. | 5,755,717 A | 5/1998 | Yates et al. |
| 5,643,291 A | 7/1997 | Pier et al. | 5,758,814 A | 6/1998 | Gallagher et al. |
| 5,645,209 A | 7/1997 | Green et al. | 5,762,256 A | 6/1998 | Mastri et al. |
| 5,647,526 A | 7/1997 | Green et al. | 5,766,188 A | 6/1998 | Igaki |
| 5,647,869 A | 7/1997 | Goble et al. | 5,766,205 A | 6/1998 | Zvenyatsky et al. |
| 5,649,937 A | 7/1997 | Bito et al. | 5,769,892 A | 6/1998 | Kingwell |
| 5,651,491 A | 7/1997 | Heaton et al. | 5,772,578 A | 6/1998 | Heimberger et al. |
| 5,653,373 A | 8/1997 | Green et al. | 5,772,659 A | 6/1998 | Becker et al. |
| 5,653,374 A | 8/1997 | Young et al. | 5,776,130 A | 7/1998 | Buysse et al. |
| 5,653,677 A | 8/1997 | Okada et al. | 5,779,130 A | 7/1998 | Alesi et al. |
| 5,653,721 A | 8/1997 | Knodel et al. | 5,779,131 A | 7/1998 | Knodel et al. |
| 5,655,698 A | 8/1997 | Yoon | 5,779,132 A | 7/1998 | Knodel et al. |
| 5,657,921 A | 8/1997 | Young et al. | 5,782,396 A | 7/1998 | Mastri et al. |
| 5,658,281 A | 8/1997 | Heard | 5,782,397 A | 7/1998 | Koukline |
| 5,658,300 A | 8/1997 | Bito et al. | 5,782,859 A | 7/1998 | Nicholas et al. |
| 5,662,258 A | 9/1997 | Knodel et al. | 5,784,934 A | 7/1998 | Izumisawa |
| 5,662,260 A | 9/1997 | Yoon | 5,785,232 A | 7/1998 | Vidal et al. |

| | | | | | | |
|---|---|---|---|---|---|---|
| 5,787,897 A | 8/1998 | Kieturakis | | 6,033,378 A | 3/2000 | Lundquist et al. |
| 5,792,135 A | 8/1998 | Madhani et al. | | 6,033,399 A | 3/2000 | Gines |
| 5,794,834 A | 8/1998 | Hamblin et al. | | 6,033,427 A | 3/2000 | Lee |
| 5,796,188 A | 8/1998 | Bays | | 6,039,733 A | 3/2000 | Buysse et al. |
| 5,797,536 A | 8/1998 | Smith et al. | | 6,039,734 A | 3/2000 | Goble |
| 5,797,537 A | 8/1998 | Oberlin et al. | | 6,045,560 A | 4/2000 | McKean et al. |
| 5,797,538 A | 8/1998 | Heaton et al. | | 6,050,472 A | 4/2000 | Shibata |
| 5,797,906 A | 8/1998 | Rhum et al. | | 6,053,390 A | 4/2000 | Green et al. |
| 5,797,959 A | 8/1998 | Castro et al. | | 6,056,746 A | 5/2000 | Goble et al. |
| 5,799,857 A | 9/1998 | Robertson et al. | | 6,063,097 A | 5/2000 | Oi et al. |
| 5,807,393 A | 9/1998 | Williamson, IV et al. | | 6,068,627 A | 5/2000 | Orszulak et al. |
| 5,809,441 A | 9/1998 | McKee | | 6,071,233 A | 6/2000 | Ishikawa et al. |
| 5,810,855 A | 9/1998 | Rayburn et al. | | 6,074,386 A | 6/2000 | Goble et al. |
| 5,813,813 A | 9/1998 | Daum et al. | | 6,077,286 A | 6/2000 | Cuschieri et al. |
| 5,814,057 A | 9/1998 | Oi et al. | | 6,079,606 A | 6/2000 | Milliman et al. |
| 5,817,084 A | 10/1998 | Jensen | | 6,083,234 A | 7/2000 | Nicholas et al. |
| 5,817,091 A | 10/1998 | Nardella et al. | | 6,083,242 A | 7/2000 | Cook |
| 5,817,093 A | 10/1998 | Williamson, IV et al. | | 6,086,600 A | 7/2000 | Kortenbach |
| 5,817,109 A | 10/1998 | McGarry et al. | | 6,090,106 A | 7/2000 | Goble et al. |
| 5,820,009 A | 10/1998 | Melling et al. | | 6,093,186 A | 7/2000 | Goble |
| 5,823,066 A | 10/1998 | Huitema et al. | | 6,099,537 A | 8/2000 | Sugai et al. |
| 5,826,776 A | 10/1998 | Schulze et al. | | 6,099,551 A | 8/2000 | Gabbay |
| 5,827,271 A | 10/1998 | Buysse et al. | | 6,109,500 A | 8/2000 | Alli et al. |
| 5,829,662 A | 11/1998 | Allen et al. | | 6,117,158 A | 9/2000 | Measamer et al. |
| 5,833,690 A | 11/1998 | Yates et al. | | 6,119,913 A | 9/2000 | Adams et al. |
| 5,833,695 A | 11/1998 | Yoon | | 6,123,241 A | 9/2000 | Walter et al. |
| 5,833,696 A | 11/1998 | Whitfield et al. | | H1904 H | 10/2000 | Yates et al. |
| 5,836,503 A | 11/1998 | Ehrenfels et al. | | 6,126,058 A | 10/2000 | Adams et al. |
| 5,839,639 A | 11/1998 | Sauer et al. | | 6,126,670 A | 10/2000 | Walker et al. |
| 5,843,132 A | 12/1998 | Ilvento | | 6,131,789 A | 10/2000 | Schulze et al. |
| 5,846,254 A | 12/1998 | Schulze et al. | | 6,132,368 A | 10/2000 | Cooper |
| 5,849,011 A | 12/1998 | Jones et al. | | 6,139,546 A | 10/2000 | Koenig et al. |
| 5,855,311 A | 1/1999 | Hamblin et al. | | 6,155,473 A | 12/2000 | Tompkins et al. |
| 5,860,975 A | 1/1999 | Goble et al. | | 6,156,056 A | 12/2000 | Kearns et al. |
| 5,865,361 A | 2/1999 | Milliman et al. | | 6,159,146 A | 12/2000 | El Gazayerli |
| 5,868,760 A | 2/1999 | McGuckin, Jr. | | 6,159,200 A | 12/2000 | Verdura et al. |
| 5,871,135 A | 2/1999 | Williamson, IV et al. | | 6,162,208 A | 12/2000 | Hipps |
| 5,876,401 A | 3/1999 | Schulze et al. | | 6,165,175 A | 12/2000 | Wampler et al. |
| 5,878,193 A | 3/1999 | Wang et al. | | 6,168,605 B1 | 1/2001 | Measamer et al. |
| 5,878,937 A | 3/1999 | Green et al. | | 6,171,316 B1 | 1/2001 | Kovac et al. |
| 5,878,938 A | 3/1999 | Bittner et al. | | 6,171,330 B1 | 1/2001 | Benchetrit |
| 5,891,160 A | 4/1999 | Williamson, IV et al. | | 6,174,308 B1 | 1/2001 | Goble et al. |
| 5,893,506 A | 4/1999 | Powell | | 6,179,776 B1 | 1/2001 | Adams et al. |
| 5,894,979 A | 4/1999 | Powell | | 6,181,105 B1 | 1/2001 | Cutolo et al. |
| 5,897,562 A | 4/1999 | Bolanos et al. | | 6,193,129 B1 | 2/2001 | Bittner et al. |
| 5,899,914 A | 5/1999 | Zirps et al. | | 6,197,042 B1 | 3/2001 | Ginn et al. |
| 5,901,895 A | 5/1999 | Heaton et al. | | 6,202,914 B1 | 3/2001 | Geiste et al. |
| 5,902,312 A | 5/1999 | Frater et al. | | 6,214,028 B1 | 4/2001 | Yoon et al. |
| 5,904,693 A | 5/1999 | Dicesare et al. | | 6,220,368 B1 | 4/2001 | Ark et al. |
| 5,906,625 A | 5/1999 | Bito et al. | | 6,223,835 B1 | 5/2001 | Habedank et al. |
| 5,908,402 A | 6/1999 | Blythe | | 6,228,081 B1 | 5/2001 | Goble |
| 5,908,427 A | 6/1999 | McKean et al. | | 6,228,084 B1 | 5/2001 | Kirwan, Jr. |
| 5,911,353 A | 6/1999 | Bolanos et al. | | 6,231,565 B1 | 5/2001 | Tovey et al. |
| 5,918,791 A | 7/1999 | Sorrentino et al. | | 6,234,178 B1 | 5/2001 | Goble et al. |
| 5,919,198 A | 7/1999 | Graves, Jr. et al. | | 6,241,139 B1 | 6/2001 | Milliman et al. |
| 5,928,256 A | 7/1999 | Riza | | 6,241,723 B1 | 6/2001 | Heim et al. |
| 5,931,847 A | 8/1999 | Bittner et al. | | 6,249,076 B1 | 6/2001 | Madden et al. |
| 5,938,667 A | 8/1999 | Peyser et al. | | 6,250,532 B1 | 6/2001 | Green et al. |
| 5,941,442 A | 8/1999 | Geiste et al. | | 6,258,107 B1 | 7/2001 | Balázs et al. |
| 5,944,172 A | 8/1999 | Hannula | | 6,261,286 B1 | 7/2001 | Goble et al. |
| 5,944,715 A | 8/1999 | Goble et al. | | 6,264,086 B1 | 7/2001 | McGuckin, Jr. |
| 5,948,030 A | 9/1999 | Miller et al. | | 6,264,087 B1 | 7/2001 | Whitman |
| 5,951,552 A | 9/1999 | Long et al. | | 6,270,508 B1 | 8/2001 | Klieman et al. |
| 5,951,574 A | 9/1999 | Stefanchik et al. | | 6,273,897 B1 | 8/2001 | Dalessandro et al. |
| 5,954,259 A | 9/1999 | Viola et al. | | 6,277,114 B1 | 8/2001 | Bullivant et al. |
| 5,964,774 A | 10/1999 | McKean et al. | | 6,293,942 B1 | 9/2001 | Goble et al. |
| 5,988,479 A | 11/1999 | Palmer | | 6,296,640 B1 | 10/2001 | Wampler et al. |
| 6,003,517 A | 12/1999 | Sheffield et al. | | 6,302,311 B1 | 10/2001 | Adams et al. |
| 6,004,319 A | 12/1999 | Goble et al. | | 6,306,134 B1 | 10/2001 | Goble et al. |
| 6,010,054 A | 1/2000 | Johnson et al. | | 6,315,184 B1 | 11/2001 | Whitman |
| 6,012,494 A | 1/2000 | Balazs | | 6,320,123 B1 | 11/2001 | Reimers |
| 6,013,076 A | 1/2000 | Goble et al. | | 6,324,339 B1 | 11/2001 | Hudson et al. |
| 6,015,406 A | 1/2000 | Goble et al. | | 6,325,799 B1 | 12/2001 | Goble |
| 6,017,356 A | 1/2000 | Frederick et al. | | 6,325,810 B1 | 12/2001 | Hamilton et al. |
| 6,022,352 A | 2/2000 | Vandewalle | | 6,330,965 B1 | 12/2001 | Milliman et al. |
| 6,024,741 A | 2/2000 | Williamson, IV et al. | | 6,331,761 B1 | 12/2001 | Kumar et al. |
| 6,024,748 A | 2/2000 | Manzo et al. | | 6,336,926 B1 | 1/2002 | Goble |
| 6,027,501 A | 2/2000 | Goble et al. | | 6,346,077 B1 | 2/2002 | Taylor et al. |
| 6,032,849 A | 3/2000 | Mastri et al. | | 6,352,503 B1 | 3/2002 | Matsui et al. |

| | | |
|---|---|---|
| 6,358,224 B1 | 3/2002 | Tims et al. |
| 6,364,877 B1 | 4/2002 | Goble et al. |
| 6,364,888 B1 | 4/2002 | Niemeyer et al. |
| 6,387,113 B1 | 5/2002 | Hawkins et al. |
| 6,387,114 B2 | 5/2002 | Adams |
| 6,398,781 B1 | 6/2002 | Goble et al. |
| 6,398,797 B2 | 6/2002 | Bombard et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| RE37,814 E | 8/2002 | Allgeyer |
| 6,436,097 B1 | 8/2002 | Nardella |
| 6,436,107 B1 | 8/2002 | Wang et al. |
| 6,436,122 B1 | 8/2002 | Frank et al. |
| 6,440,146 B2 | 8/2002 | Nicholas et al. |
| 6,443,973 B1 | 9/2002 | Whitman |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,685,727 B2 | 2/2004 | Fisher et al. |
| 6,695,199 B2 | 2/2004 | Whitman |
| 6,698,643 B2 | 3/2004 | Whitman |
| 6,704,210 B1 | 3/2004 | Myers |
| 6,716,223 B2 | 4/2004 | Leopold et al. |
| 6,716,232 B1 | 4/2004 | Vidal et al. |
| 6,716,233 B1 | 4/2004 | Whitman |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |

| | | |
|---|---|---|
| 6,984,203 B2 | 1/2006 | Tartaglia et al. |
| 6,984,231 B2 | 1/2006 | Goble et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,037,344 B2 | 5/2006 | Kagan et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,087,071 B2 | 8/2006 | Nicholas et al. |
| 7,090,637 B2 | 8/2006 | Danitz et al. |
| 7,090,684 B2 | 8/2006 | McGuckin, Jr. et al. |
| 7,094,202 B2 | 8/2006 | Nobis et al. |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,143,925 B2 | 12/2006 | Shelton, IV et al. |
| 7,143,926 B2 | 12/2006 | Shelton, IV et al. |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,161,036 B2 | 1/2007 | Oikawa et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,211,081 B2 | 5/2007 | Goble |
| 7,211,084 B2 | 5/2007 | Goble et al. |
| 7,214,224 B2 | 5/2007 | Goble |
| 7,220,260 B2 | 5/2007 | Fleming et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,303,106 B2 | 12/2007 | Milliman et al. |
| 7,303,107 B2 | 12/2007 | Milliman et al. |
| 7,303,556 B2 | 12/2007 | Metzger |
| 7,324,572 B2 | 1/2008 | Chang |
| 7,328,829 B2 | 2/2008 | Arad et al. |
| 7,330,004 B2 | 2/2008 | DeJonge et al. |
| 7,334,717 B2 | 2/2008 | Rethy et al. |
| 7,336,184 B2 | 2/2008 | Smith et al. |
| 7,338,513 B2 | 3/2008 | Lee et al. |
| 7,348,763 B1 | 3/2008 | Reinhart et al. |
| 7,351,258 B2 | 4/2008 | Ricotta et al. |
| 7,364,060 B2 | 4/2008 | Milliman |
| 7,377,928 B2 | 5/2008 | Zubik et al. |
| 7,388,217 B2 | 6/2008 | Buschbeck et al. |
| 7,397,364 B2 | 7/2008 | Govari |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,418,078 B2 | 8/2008 | Blanz et al. |
| 7,419,080 B2 | 9/2008 | Smith et al. |
| 7,422,136 B1 | 9/2008 | Marczyk |
| 7,424,965 B2 | 9/2008 | Racenet et al. |
| 7,431,188 B1 | 10/2008 | Marczyk |
| 7,431,694 B2 | 10/2008 | Stefanchik et al. |
| 7,438,209 B1 | 10/2008 | Hess et al. |
| 7,439,354 B2 | 10/2008 | Lenges et al. |
| 7,441,685 B1 | 10/2008 | Boudreaux |
| 7,461,767 B2 | 12/2008 | Viola et al. |
| 7,464,847 B2 | 12/2008 | Viola et al. |
| 7,472,814 B2 | 1/2009 | Mastri et al. |
| 7,473,253 B2 | 1/2009 | Dycus et al. |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,506,790 B2 | 3/2009 | Shelton, IV |
| 7,510,107 B2 | 3/2009 | Timm et al. |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,563,862 B2 | 7/2009 | Sieg et al. |
| 7,566,300 B2 | 7/2009 | Devierre et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |

| Patent No. | Date | Inventor |
|---|---|---|
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,611,038 B2 | 11/2009 | Racenet et al. |
| 7,615,003 B2 | 11/2009 | Stefanchik et al. |
| 7,631,793 B2 | 12/2009 | Rethy et al. |
| 7,641,092 B2 | 1/2010 | Kruszynski et al. |
| 7,641,093 B2 | 1/2010 | Doll et al. |
| 7,651,498 B2 | 1/2010 | Shifrin et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 7,674,255 B2 | 3/2010 | Braun |
| 7,682,307 B2 | 3/2010 | Danitz et al. |
| 7,686,826 B2 | 3/2010 | Lee et al. |
| 7,691,098 B2 | 4/2010 | Wallace et al. |
| 7,699,204 B2 | 4/2010 | Viola |
| 7,717,312 B2 | 5/2010 | Beetel |
| 7,721,930 B2 | 5/2010 | McKenna et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,743,960 B2 | 6/2010 | Whitman et al. |
| 7,744,627 B2 | 6/2010 | Orban, III et al. |
| 7,753,245 B2 | 7/2010 | Boudreaux et al. |
| 7,766,209 B2 | 8/2010 | Baxter, III et al. |
| 7,771,396 B2 | 8/2010 | Stefanchik et al. |
| 7,780,685 B2 | 8/2010 | Hunt et al. |
| 7,793,812 B2 | 9/2010 | Moore et al. |
| 7,798,386 B2 | 9/2010 | Schall et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,401 B2 | 11/2010 | Manzo et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,836,400 B2 | 11/2010 | May et al. |
| 7,837,080 B2 | 11/2010 | Schwemberger |
| 7,845,533 B2 | 12/2010 | Marczyk et al. |
| 7,845,534 B2 | 12/2010 | Viola et al. |
| 7,846,149 B2 | 12/2010 | Jankowski |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,887,530 B2 | 2/2011 | Zemlok et al. |
| 7,900,191 B1 | 3/2011 | Baker et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,950,560 B2 | 5/2011 | Zemlok et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,980,443 B2 | 7/2011 | Scheib et al. |
| 8,002,795 B2 | 8/2011 | Beetel |
| 8,011,551 B2 | 9/2011 | Marczyk et al. |
| 8,020,743 B2 | 9/2011 | Shelton, IV |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 2002/0022836 A1 | 2/2002 | Goble et al. |
| 2002/0029036 A1 | 3/2002 | Goble et al. |
| 2002/0117534 A1 | 8/2002 | Green et al. |
| 2002/0134811 A1 | 9/2002 | Napier et al. |
| 2002/0165541 A1 | 11/2002 | Whitman |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0216732 A1 | 11/2003 | Truckai et al. |
| 2003/0216778 A1 | 11/2003 | Weadock |
| 2003/0220660 A1 | 11/2003 | Kortenbach et al. |
| 2004/0002726 A1 | 1/2004 | Nunez et al. |
| 2004/0006340 A1 | 1/2004 | Latterell et al. |
| 2004/0006372 A1 | 1/2004 | Racenet et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0101822 A1 | 5/2004 | Wiesner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0122471 A1 | 6/2004 | Toby et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0222268 A1 | 11/2004 | Bilotti et al. |
| 2004/0232199 A1 | 11/2004 | Shelton, IV et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0006434 A1 | 1/2005 | Wales et al. |
| 2005/0021026 A1 | 1/2005 | Baily |
| 2005/0021078 A1* | 1/2005 | Vleugels et al. ............... 606/205 |
| 2005/0023324 A1 | 2/2005 | Doll et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070925 A1 | 3/2005 | Shelton, IV et al. |
| 2005/0070929 A1 | 3/2005 | Dalessandro et al. |
| 2005/0070958 A1 | 3/2005 | Swayze et al. |
| 2005/0072827 A1 | 4/2005 | Mollenauer |
| 2005/0080454 A1 | 4/2005 | Drews et al. |
| 2005/0085693 A1 | 4/2005 | Belson et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |

| | | |
|---|---|---|
| 2005/0137455 A1 | 6/2005 | Ewers et al. |
| 2005/0143759 A1 | 6/2005 | Kelly |
| 2005/0145671 A1 | 7/2005 | Viola |
| 2005/0154258 A1 | 7/2005 | Tartaglia et al. |
| 2005/0165415 A1 | 7/2005 | Wales |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0173490 A1 | 8/2005 | Shelton et al. |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0230453 A1 | 10/2005 | Viola |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263562 A1 | 12/2005 | Shelton, IV et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton |
| 2006/0047275 A1 | 3/2006 | Goble |
| 2006/0047307 A1 | 3/2006 | Ortiz et al. |
| 2006/0047308 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087442 A1 | 4/2006 | Smith et al. |
| 2006/0100643 A1 | 5/2006 | Laufer et al. |
| 2006/0108393 A1 | 5/2006 | Heinrich et al. |
| 2006/0111710 A1 | 5/2006 | Goble et al. |
| 2006/0111711 A1 | 5/2006 | Goble |
| 2006/0122636 A1 | 6/2006 | Bailley et al. |
| 2006/0142772 A1 | 6/2006 | Ralph et al. |
| 2006/0149163 A1 | 7/2006 | Hibner et al. |
| 2006/0151567 A1 | 7/2006 | Roy |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0190028 A1 | 8/2006 | Wales et al. |
| 2006/0190029 A1 | 8/2006 | Wales |
| 2006/0190031 A1 | 8/2006 | Wales et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0229665 A1 | 10/2006 | Wales et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0045379 A1 | 3/2007 | Shelton |
| 2007/0055219 A1 | 3/2007 | Whitman et al. |
| 2007/0070574 A1 | 3/2007 | Nerheim et al. |
| 2007/0073340 A1 | 3/2007 | Shelton, IV et al. |
| 2007/0073341 A1 | 3/2007 | Smith et al. |
| 2007/0075114 A1 | 4/2007 | Shelton, IV et al. |
| 2007/0078484 A1 | 4/2007 | Talarico et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0135803 A1 | 6/2007 | Belson |
| 2007/0158358 A1 | 7/2007 | Mason, II et al. |
| 2007/0173806 A1 | 7/2007 | Orszulak et al. |
| 2007/0173813 A1 | 7/2007 | Odom |
| 2007/0175958 A1 | 8/2007 | Shelton, IV et al. |
| 2007/0175959 A1 | 8/2007 | Shelton, IV et al. |
| 2007/0181632 A1 | 8/2007 | Milliman |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton, IV et al. |
| 2007/0246505 A1 | 10/2007 | Pace-Floridia et al. |
| 2007/0260278 A1 | 11/2007 | Wheeler et al. |
| 2007/0262116 A1 | 11/2007 | Hueil et al. |
| 2007/0270784 A1 | 11/2007 | Smith et al. |
| 2007/0288044 A1 | 12/2007 | Jinno et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |

| | | |
|---|---|---|
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0228029 A1 | 9/2008 | Mikkaichi et al. |
| 2008/0251568 A1 | 10/2008 | Zemlok et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0292283 A1 | 11/2009 | Odom |
| 2009/0308907 A1 | 12/2009 | Nalagatla et al. |
| 2010/0001036 A1 | 1/2010 | Marczyk et al. |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0069942 A1 | 3/2010 | Shelton, IV |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2010/0312261 A1 | 12/2010 | Suzuki et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |

| | | | |
|---|---|---|---|
| 2011/0295269 A1 | 12/2011 | Swensgard et al. | |
| 2011/0295270 A1 | 12/2011 | Giordano et al. | |
| 2011/0295295 A1 | 12/2011 | Shelton, IV et al. | |

FOREIGN PATENT DOCUMENTS

| | | | |
|---|---|---|---|
| CA | 2514274 A1 | 1/2006 | |
| CN | 1868411 A | 11/2006 | |
| CN | 1915180 A | 2/2007 | |
| DE | 273689 C | 5/1914 | |
| DE | 1775926 A | 1/1972 | |
| DE | 3036217 A1 | 4/1982 | |
| DE | 3210466 A1 | 9/1983 | |
| DE | 9412228 U | 9/1994 | |
| DE | 19509116 A1 | 9/1996 | |
| DE | 19851291 A1 | 1/2000 | |
| DE | 19924311 A1 | 11/2000 | |
| DE | 69328576 T2 | 1/2001 | |
| DE | 10052679 A1 | 5/2001 | |
| DE | 20112837 U1 | 10/2001 | |
| DE | 20121753 U1 | 4/2003 | |
| DE | 202007003114 U1 | 6/2007 | |
| EP | 0122046 A1 | 10/1984 | |
| EP | 0070230 B1 | 10/1985 | |
| EP | 0387980 B1 | 10/1985 | |
| EP | 0033548 B1 | 5/1986 | |
| EP | 0276104 A2 | 7/1988 | |
| EP | 0248844 B1 | 1/1993 | |
| EP | 0545029 A1 | 6/1993 | |
| EP | 0277959 B1 | 10/1993 | |
| EP | 0233940 B1 | 11/1993 | |
| EP | 0261230 B1 | 11/1993 | |
| EP | 0639349 A2 | 2/1994 | |
| EP | 0324636 B1 | 3/1994 | |
| EP | 0593920 A1 | 4/1994 | |
| EP | 0523174 B1 | 6/1994 | |
| EP | 0310431 B1 | 11/1994 | |
| EP | 0375302 B1 | 11/1994 | |
| EP | 0376562 81 | 11/1994 | |
| EP | 0630612 A1 | 12/1994 | |
| EP | 0634144 A1 | 1/1995 | |
| EP | 0646356 A2 | 4/1995 | |
| EP | 0646357 A1 | 4/1995 | |
| EP | 0653189 A2 | 5/1995 | |
| EP | 0669104 A1 | 8/1995 | |
| EP | 0511470 B1 | 10/1995 | |
| EP | 0679367 A2 | 11/1995 | |
| EP | 0685204 A1 | 12/1995 | |
| EP | 0364216 B1 | 1/1996 | |
| EP | 0699418 A1 | 3/1996 | |
| EP | 0702937 A1 | 3/1996 | |
| EP | 0705571 A1 | 4/1996 | |
| EP | 0711611 A2 | 5/1996 | |
| EP | 0484677 B2 | 6/1996 | |
| EP | 0541987 B1 | 7/1996 | |
| EP | 0667119 B1 | 7/1996 | |
| EP | 0708618 B1 | 3/1997 | |
| EP | 0770355 A1 | 5/1997 | |
| EP | 0503662 B1 | 6/1997 | |
| EP | 0447121 B1 | 7/1997 | |
| EP | 0625077 B1 | 7/1997 | |
| EP | 0633749 B1 | 8/1997 | |
| EP | 0710090 B1 | 8/1997 | |
| EP | 0578425 B1 | 9/1997 | |
| EP | 0625335 B1 | 11/1997 | |
| EP | 0552423 B1 | 1/1998 | |
| EP | 0592244 B1 | 1/1998 | |
| EP | 0648476 B1 | 1/1998 | |
| EP | 0649290 B1 | 3/1998 | |
| EP | 0598618 B1 | 9/1998 | |
| EP | 0676173 B1 | 9/1998 | |
| EP | 0678007 81 | 9/1998 | |
| EP | 0603472 B1 | 11/1998 | |
| EP | 0605351 B1 | 11/1998 | |
| EP | 0878169 A1 | 11/1998 | |
| EP | 0879742 A1 | 11/1998 | |
| EP | 0695144 B1 | 12/1998 | |
| EP | 0722296 B1 | 12/1998 | |
| EP | 0760230 B1 | 2/1999 | |
| EP | 0623316 B1 | 3/1999 | |
| EP | 0650701 B1 | 3/1999 | |
| EP | 0537572 B1 | 6/1999 | |
| EP | 0923907 A1 | 6/1999 | |
| EP | 0843906 B1 | 3/2000 | |
| EP | 0552050 B1 | 5/2000 | |
| EP | 0833592 B1 | 5/2000 | |
| EP | 0830094 B1 | 9/2000 | |
| EP | 1034747 A1 | 9/2000 | |
| EP | 1034748 A1 | 9/2000 | |
| EP | 0694290 B1 | 11/2000 | |
| EP | 1050278 A1 | 11/2000 | |
| EP | 1053719 A1 | 11/2000 | |
| EP | 1053720 A1 | 11/2000 | |
| EP | 1055399 A1 | 11/2000 | |
| EP | 1055400 A1 | 11/2000 | |
| EP | 1080694 A1 | 3/2001 | |
| EP | 1095627 A1 | 5/2001 | |
| EP | 1256318 B1 | 5/2001 | |
| EP | 0806914 B1 | 9/2001 | |
| EP | 0768840 B1 | 12/2001 | |
| EP | 0908152 B1 | 1/2002 | |
| EP | 0872213 B1 | 5/2002 | |
| EP | 0862386 B1 | 6/2002 | |
| EP | 0949886 B1 | 9/2002 | |
| EP | 1238634 A2 | 9/2002 | |
| EP | 0858295 B1 | 12/2002 | |
| EP | 0656188 B1 | 1/2003 | |
| EP | 1284120 A1 | 2/2003 | |
| EP | 1287788 A1 | 3/2003 | |
| EP | 0717966 B1 | 4/2003 | |
| EP | 0869742 B1 | 5/2003 | |
| EP | 0829235 B1 | 6/2003 | |
| EP | 0887046 B1 | 7/2003 | |
| EP | 0852480 B1 | 8/2003 | |
| EP | 0891154 B1 | 9/2003 | |
| EP | 0873089 B1 | 10/2003 | |
| EP | 0856326 B1 | 11/2003 | |
| EP | 1374788 A1 | 1/2004 | |
| EP | 0741996 B1 | 2/2004 | |
| EP | 0814712 B1 | 2/2004 | |
| EP | 1402837 A1 | 3/2004 | |
| EP | 0705570 B1 | 4/2004 | |
| EP | 0959784 B1 | 4/2004 | |
| EP | 1407719 A2 | 4/2004 | |
| EP | 1086713 B1 | 5/2004 | |
| EP | 0996378 B1 | 6/2004 | |
| EP | 1426012 A1 | 6/2004 | |
| EP | 0833593 B2 | 7/2004 | |
| EP | 1442694 A1 | 8/2004 | |
| EP | 0888749 B1 | 9/2004 | |
| EP | 0959786 B1 | 9/2004 | |
| EP | 1459695 A1 | 9/2004 | |
| EP | 1473819 A1 | 11/2004 | |
| EP | 1477119 A1 | 11/2004 | |
| EP | 1479345 A1 | 11/2004 | |
| EP | 1479347 A1 | 11/2004 | |
| EP | 1479348 A1 | 11/2004 | |
| EP | 0754437 B2 | 12/2004 | |
| EP | 1025807 B1 | 12/2004 | |
| EP | 1001710 B1 | 1/2005 | |
| EP | 1520521 A1 | 4/2005 | |
| EP | 1520523 A1 | 4/2005 | |
| EP | 1520525 A1 | 4/2005 | |
| EP | 1523942 A2 | 4/2005 | |
| EP | 1550408 A1 | 7/2005 | |
| EP | 1557129 A1 | 7/2005 | |
| EP | 1064883 B1 | 8/2005 | |
| EP | 1067876 B1 | 8/2005 | |
| EP | 0870473 B1 | 9/2005 | |
| EP | 1157666 B1 | 9/2005 | |
| EP | 0880338 B1 | 10/2005 | |
| EP | 1158917 B1 | 11/2005 | |
| EP | 1344498 B1 | 11/2005 | |
| EP | 1330989 B1 | 12/2005 | |
| EP | 0771176 B2 | 1/2006 | |
| EP | 1621138 A2 | 2/2006 | |
| EP | 1621139 A2 | 2/2006 | |
| EP | 1621141 A2 | 2/2006 | |
| EP | 1621145 A2 | 2/2006 | |

| | | | | | | |
|---|---|---|---|---|---|---|
| EP | 1621151 A2 | 2/2006 | | JP | 8229050 A | 9/1996 |
| EP | 1034746 B1 | 3/2006 | | JP | 2000033071 A | 2/2000 |
| EP | 1632191 A2 | 3/2006 | | JP | 2000171730 A | 6/2000 |
| EP | 1065981 B1 | 5/2006 | | JP | 2000287987 A | 10/2000 |
| EP | 1082944 B1 | 5/2006 | | JP | 2000325303 A | 11/2000 |
| EP | 1652481 A2 | 5/2006 | | JP | 2001286477 A | 10/2001 |
| EP | 1253866 B1 | 7/2006 | | JP | 2002143078 A | 5/2002 |
| EP | 1032318 B1 | 8/2006 | | JP | 2002369820 A | 12/2002 |
| EP | 1045672 B1 | 8/2006 | | JP | 2005505322 T | 2/2005 |
| EP | 1617768 B1 | 8/2006 | | JP | 2005103293 A | 4/2005 |
| EP | 1693015 A2 | 8/2006 | | JP | 2005131163 A | 5/2005 |
| EP | 1400214 B1 | 9/2006 | | JP | 2005131164 A | 5/2005 |
| EP | 1129665 B1 | 11/2006 | | JP | 2005131173 A | 5/2005 |
| EP | 1400206 B1 | 11/2006 | | JP | 2005131211 A | 5/2005 |
| EP | 1721568 A1 | 11/2006 | | JP | 2005131212 A | 5/2005 |
| EP | 1256317 B1 | 12/2006 | | JP | 2005137423 A | 6/2005 |
| EP | 1728473 A1 | 12/2006 | | JP | 2005152416 A | 6/2005 |
| EP | 1728475 A2 | 12/2006 | | JP | 2006-281405 A | 10/2006 |
| EP | 1479346 B1 | 1/2007 | | RU | 2008830 C1 | 3/1994 |
| EP | 1484024 B1 | 1/2007 | | RU | 2187249 C2 | 8/2002 |
| EP | 1754445 A2 | 2/2007 | | RU | 2225170 C2 | 3/2004 |
| EP | 1759812 A1 | 3/2007 | | SU | 189517 A | 1/1967 |
| EP | 1767163 A1 | 3/2007 | | SU | 328636 A | 9/1972 |
| EP | 1769756 A1 | 4/2007 | | SU | 886900 A1 | 12/1981 |
| EP | 1769758 A1 | 4/2007 | | SU | 1009439 A | 4/1983 |
| EP | 1581128 B1 | 5/2007 | | SU | 1333319 A2 | 8/1987 |
| EP | 1785097 A2 | 5/2007 | | SU | 1377053 A1 | 2/1988 |
| EP | 1790293 A2 | 5/2007 | | SU | 1561964 A1 | 5/1990 |
| EP | 1800610 A1 | 6/2007 | | SU | 1722476 A1 | 3/1992 |
| EP | 1300117 B1 | 8/2007 | | WO | WO 91/15157 A1 | 10/1991 |
| EP | 1813199 A1 | 8/2007 | | WO | WO 92/20295 A1 | 11/1992 |
| EP | 1813201 A1 | 8/2007 | | WO | WO 92/21300 A1 | 12/1992 |
| EP | 1813203 A2 | 8/2007 | | WO | WO 93/13718 A1 | 7/1993 |
| EP | 1813207 A1 | 8/2007 | | WO | WO 93/14690 A1 | 8/1993 |
| EP | 1813209 A1 | 8/2007 | | WO | WO 93/15648 A1 | 8/1993 |
| EP | 1487359 B1 | 10/2007 | | WO | WO 93/15850 A1 | 8/1993 |
| EP | 1599146 B1 | 10/2007 | | WO | WO 93/19681 A1 | 10/1993 |
| EP | 1839596 A1 | 10/2007 | | WO | WO 94/00060 A1 | 1/1994 |
| EP | 1402821 B1 | 12/2007 | | WO | WO 94/11057 A1 | 5/1994 |
| EP | 1872727 A1 | 1/2008 | | WO | WO 94/12108 A1 | 6/1994 |
| EP | 1897502 A1 | 3/2008 | | WO | WO 94/18893 A1 | 9/1994 |
| EP | 1330201 B1 | 6/2008 | | WO | WO 94/22378 A1 | 10/1994 |
| EP | 1702568 B1 | 7/2008 | | WO | WO 94/23659 A1 | 10/1994 |
| EP | 1943976 A2 | 7/2008 | | WO | WO 95/02369 A1 | 1/1995 |
| EP | 1593337 B1 | 8/2008 | | WO | WO 95/03743 A1 | 2/1995 |
| EP | 1970014 A1 | 9/2008 | | WO | WO 95/06817 A1 | 3/1995 |
| EP | 1980213 A2 | 10/2008 | | WO | WO 95/09576 A1 | 4/1995 |
| EP | 1759645 B1 | 11/2008 | | WO | WO 95/09577 A1 | 4/1995 |
| EP | 1693008 B1 | 12/2008 | | WO | WO 95/14436 A1 | 6/1995 |
| EP | 1759640 B1 | 12/2008 | | WO | WO 95/17855 A1 | 7/1995 |
| EP | 2000102 A2 | 12/2008 | | WO | WO 95/18383 A1 | 7/1995 |
| EP | 1736104 B1 | 3/2009 | | WO | WO 95/18572 A1 | 7/1995 |
| EP | 1749486 B1 | 3/2009 | | WO | WO 95/19739 A1 | 7/1995 |
| EP | 1721576 B1 | 4/2009 | | WO | WO 95/20360 A1 | 8/1995 |
| EP | 1733686 B1 | 4/2009 | | WO | WO 95/23557 A1 | 9/1995 |
| EP | 1745748 B1 | 8/2009 | | WO | WO 95/24865 A1 | 9/1995 |
| EP | 2090256 A2 | 8/2009 | | WO | WO 95/25471 A3 | 9/1995 |
| EP | 1813208 B1 | 11/2009 | | WO | WO 95/26562 A1 | 10/1995 |
| EP | 1607050 B1 | 12/2009 | | WO | WO 95/29639 A1 | 11/1995 |
| EP | 1566150 B1 | 4/2010 | | WO | WO 96/04858 A1 | 2/1996 |
| EP | 1813206 B1 | 4/2010 | | WO | WO 96/19151 A1 | 6/1996 |
| EP | 1769754 B1 | 6/2010 | | WO | WO 96/19152 A1 | 6/1996 |
| EP | 1535565 B1 | 10/2010 | | WO | WO 96/20652 A1 | 7/1996 |
| EP | 1702570 B1 | 10/2010 | | WO | WO 96/21119 A1 | 7/1996 |
| EP | 1785098 B1 | 10/2010 | | WO | WO 96/22055 A1 | 7/1996 |
| FR | 999646 A | 2/1952 | | WO | WO 96/23448 A1 | 8/1996 |
| FR | 1112936 A | 3/1956 | | WO | WO 96/24301 A1 | 8/1996 |
| FR | 2765794 A | 1/1999 | | WO | WO 96/27337 A1 | 9/1996 |
| GB | 1210522 A | 10/1970 | | WO | WO 96/31155 A1 | 10/1996 |
| GB | 1217159 A | 12/1970 | | WO | WO 96/35464 A1 | 11/1996 |
| GB | 1339394 A | 12/1973 | | WO | WO 96/39085 A1 | 12/1996 |
| GB | 2109241 A | 6/1983 | | WO | WO 96/39086 A1 | 12/1996 |
| GB | 2272159 A | 5/1994 | | WO | WO 96/39087 A1 | 12/1996 |
| GB | 2284242 A | 5/1995 | | WO | WO 96/39088 A1 | 12/1996 |
| GB | 2336214 A | 10/1999 | | WO | WO 96/39089 A1 | 12/1996 |
| GB | 2425903 A | 11/2006 | | WO | WO 97/00646 A1 | 1/1997 |
| JP | 6007357 A | 1/1994 | | WO | WO 97/00647 A1 | 1/1997 |
| JP | 7051273 A | 2/1995 | | WO | WO 97/06582 A1 | 2/1997 |
| JP | 8033641 A | 2/1996 | | WO | WO 97/10763 A1 | 3/1997 |

| | | | | | | |
|---|---|---|---|---|---|---|
| WO | WO 97/10764 | A1 | 3/1997 | WO | WO 03/063694 A1 | 8/2003 |
| WO | WO 97/11648 | A2 | 4/1997 | WO | WO 03/077769 A1 | 9/2003 |
| WO | WO 97/11649 | A1 | 4/1997 | WO | WO 03/079911 A1 | 10/2003 |
| WO | WO 97/15237 | A1 | 5/1997 | WO | WO 03/082126 A1 | 10/2003 |
| WO | WO 97/24073 | A1 | 7/1997 | WO | WO 03/088845 A2 | 10/2003 |
| WO | WO 97/24993 | A1 | 7/1997 | WO | WO 03/090630 A2 | 11/2003 |
| WO | WO 97/30644 | A1 | 8/1997 | WO | WO 03/094743 A1 | 11/2003 |
| WO | WO 97/34533 | A1 | 9/1997 | WO | WO 03/094745 A1 | 11/2003 |
| WO | WO 97/37598 | A1 | 10/1997 | WO | WO 03/094746 A1 | 11/2003 |
| WO | WO 97/39688 | A2 | 10/1997 | WO | WO 03/094747 A1 | 11/2003 |
| WO | WO 98/17180 | A1 | 4/1998 | WO | WO 03/105698 A1 | 12/2003 |
| WO | WO 98/27880 | A1 | 7/1998 | WO | WO 03/105702 A2 | 12/2003 |
| WO | WO 98/30153 | A1 | 7/1998 | WO | WO 2004/006980 A2 | 1/2004 |
| WO | WO 98/47436 | A1 | 10/1998 | WO | WO 2004/019769 A1 | 3/2004 |
| WO | WO 99/03407 | A1 | 1/1999 | WO | WO 2004/021868 A2 | 3/2004 |
| WO | WO 99/03408 | A1 | 1/1999 | WO | WO 2004/028585 A2 | 4/2004 |
| WO | WO 99/03409 | A1 | 1/1999 | WO | WO 2004/032754 A2 | 4/2004 |
| WO | WO 99/12483 | A1 | 3/1999 | WO | WO 2004/032760 A2 | 4/2004 |
| WO | WO 99/12487 | A1 | 3/1999 | WO | WO 2004/032763 A2 | 4/2004 |
| WO | WO 99/12488 | A1 | 3/1999 | WO | WO 2004/034875 A2 | 4/2004 |
| WO | WO 99/15086 | A1 | 4/1999 | WO | WO 2004/047626 A1 | 6/2004 |
| WO | WO 99/15091 | A1 | 4/1999 | WO | WO 2004/047653 A2 | 6/2004 |
| WO | WO 99/23933 | A2 | 5/1999 | WO | WO 2004/052426 A2 | 6/2004 |
| WO | WO 99/23959 | A1 | 5/1999 | WO | WO 2004/056276 A1 | 7/2004 |
| WO | WO 99/25261 | A1 | 5/1999 | WO | WO 2004/056277 A1 | 7/2004 |
| WO | WO 99/29244 | A1 | 6/1999 | WO | WO 2004/062516 A1 | 7/2004 |
| WO | WO 99/34744 | A1 | 7/1999 | WO | WO 2004/078050 A2 | 9/2004 |
| WO | WO 99/45849 | A1 | 9/1999 | WO | WO 2004/078051 A2 | 9/2004 |
| WO | WO 99/48430 | A1 | 9/1999 | WO | WO 2004/086987 A1 | 10/2004 |
| WO | WO 99/51158 | A1 | 10/1999 | WO | WO 2004/096015 A2 | 11/2004 |
| WO | WO 00/24322 | A1 | 5/2000 | WO | WO 2004/096057 A2 | 11/2004 |
| WO | WO 00/24330 | A1 | 5/2000 | WO | WO 2004/103157 A2 | 12/2004 |
| WO | WO 00/41638 | A1 | 7/2000 | WO | WO 2004/105593 A1 | 12/2004 |
| WO | WO 00/48506 | A2 | 8/2000 | WO | WO 2004/105621 A1 | 12/2004 |
| WO | WO 00/53112 | A2 | 9/2000 | WO | WO 2004/112618 A2 | 12/2004 |
| WO | WO 00/54653 | A1 | 9/2000 | WO | WO 2004/112652 A2 | 12/2004 |
| WO | WO 00/57796 | A1 | 10/2000 | WO | WO 2005/027983 A2 | 3/2005 |
| WO | WO 00/64365 | A1 | 11/2000 | WO | WO 2005/037329 A2 | 4/2005 |
| WO | WO 00/72762 | A1 | 12/2000 | WO | WO 2005/044078 A2 | 5/2005 |
| WO | WO 00/72765 | A1 | 12/2000 | WO | WO 2005/055846 A1 | 6/2005 |
| WO | WO 01/03587 | A1 | 1/2001 | WO | WO 2005/072634 A2 | 8/2005 |
| WO | WO 01/05702 | A1 | 1/2001 | WO | WO 2005/078892 A1 | 8/2005 |
| WO | WO 01/10482 | A1 | 2/2001 | WO | WO 2005/096954 A2 | 10/2005 |
| WO | WO 01/35845 | A1 | 5/2001 | WO | WO 2005/112806 A2 | 12/2005 |
| WO | WO 01/54594 | A1 | 8/2001 | WO | WO 2005/112808 A1 | 12/2005 |
| WO | WO 01/58371 | A1 | 8/2001 | WO | WO 2005/115251 A2 | 12/2005 |
| WO | WO 01/62158 | A2 | 8/2001 | WO | WO 2005/117735 A1 | 12/2005 |
| WO | WO 01/62161 | A1 | 8/2001 | WO | WO 2005/122936 A1 | 12/2005 |
| WO | WO 01/62162 | A1 | 8/2001 | WO | WO 2006/027014 A1 | 3/2006 |
| WO | WO 01/62164 | A2 | 8/2001 | WO | WO 2006/044490 A2 | 4/2006 |
| WO | WO 01/62169 | A2 | 8/2001 | WO | WO 2006/044581 A2 | 4/2006 |
| WO | WO 01/78605 | A2 | 10/2001 | WO | WO 2006/044810 A2 | 4/2006 |
| WO | WO 01/91646 | A1 | 12/2001 | WO | WO 2006/051252 A2 | 5/2006 |
| WO | WO 02/07608 | A2 | 1/2002 | WO | WO 2006/059067 A1 | 6/2006 |
| WO | WO 02/07618 | A1 | 1/2002 | WO | WO 2006/083748 A1 | 8/2006 |
| WO | WO 02/17799 | A1 | 3/2002 | WO | WO 2006/092563 A1 | 9/2006 |
| WO | WO 02/19920 | A1 | 3/2002 | WO | WO 2006/092565 A1 | 9/2006 |
| WO | WO 02/19932 | A1 | 3/2002 | WO | WO 2006/115958 A1 | 11/2006 |
| WO | WO 02/30297 | A2 | 4/2002 | WO | WO 2006/125940 A1 | 11/2006 |
| WO | WO 02/32322 | A2 | 4/2002 | WO | WO 2006/132992 A1 | 12/2006 |
| WO | WO 02/36028 | A1 | 5/2002 | WO | WO 2007/002180 A2 | 1/2007 |
| WO | WO 02/43571 | A2 | 6/2002 | WO | WO 2007/016290 A2 | 2/2007 |
| WO | WO 02/058568 | A1 | 8/2002 | WO | WO 2007/018898 A2 | 2/2007 |
| WO | WO 02/060328 | A1 | 8/2002 | WO | WO 2007/098220 A2 | 8/2007 |
| WO | WO 02/067785 | A2 | 9/2002 | WO | WO 2007/121579 A1 | 11/2007 |
| WO | WO 02/098302 | A1 | 12/2002 | WO | WO 2007/137304 A2 | 11/2007 |
| WO | WO 03/000138 | A2 | 1/2003 | WO | WO 2007/139734 A2 | 12/2007 |
| WO | WO 03/001329 | A2 | 1/2003 | WO | WO 2007/142625 A2 | 12/2007 |
| WO | WO 03/013363 | A1 | 2/2003 | WO | WO 2008/021969 A2 | 2/2008 |
| WO | WO 03/015604 | A2 | 2/2003 | WO | WO 2008/039270 A1 | 4/2008 |
| WO | WO 03/020106 | A2 | 3/2003 | WO | WO 2008/045383 A2 | 4/2008 |
| WO | WO 03/020139 | A2 | 3/2003 | WO | WO 2008/109125 A1 | 9/2008 |
| WO | WO 03/024339 | A1 | 3/2003 | WO | WO 2010/063795 A1 | 6/2010 |
| WO | WO 03/079909 | A3 | 3/2003 | | | |
| WO | WO 03/030743 | A2 | 4/2003 | | | |
| WO | WO 03/047436 | A3 | 6/2003 | | | |
| WO | WO 03/055402 | A1 | 7/2003 | | | |
| WO | WO 03/057048 | A1 | 7/2003 | | | |
| WO | WO 03/057058 | A1 | 7/2003 | | | |

OTHER PUBLICATIONS

Office Action issued on Jun. 18, 2007 in U.S. Appl. No. 11/343,545.
Office Action issued on Jun. 25, 2007 in U.S. Appl. No. 11/343,546.
European Search Report, Application No. 07250383.2, dated Jun. 19, 2007 (9 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

Singapore Examination Report for Application No. 200700738-8, dated Jan. 20, 2009 (9 pages).

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online]URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

U.S. Appl. No. 12/032,024, filed Feb. 15, 2008.
U.S. Appl. No. 12/031,580, filed Feb. 14, 2008.
U.S. Appl. No. 12/031,368, filed Feb. 14, 2008.
U.S. Appl. No. 12/031,542, filed Feb. 14, 2008.
U.S. Appl. No. 12/031,556, filed Feb. 14, 2008.
U.S. Appl. No. 12/031,573, filed Feb. 14, 2008.
U.S. Appl. No. 13/118,241, filed May 27, 2011.

* cited by examiner

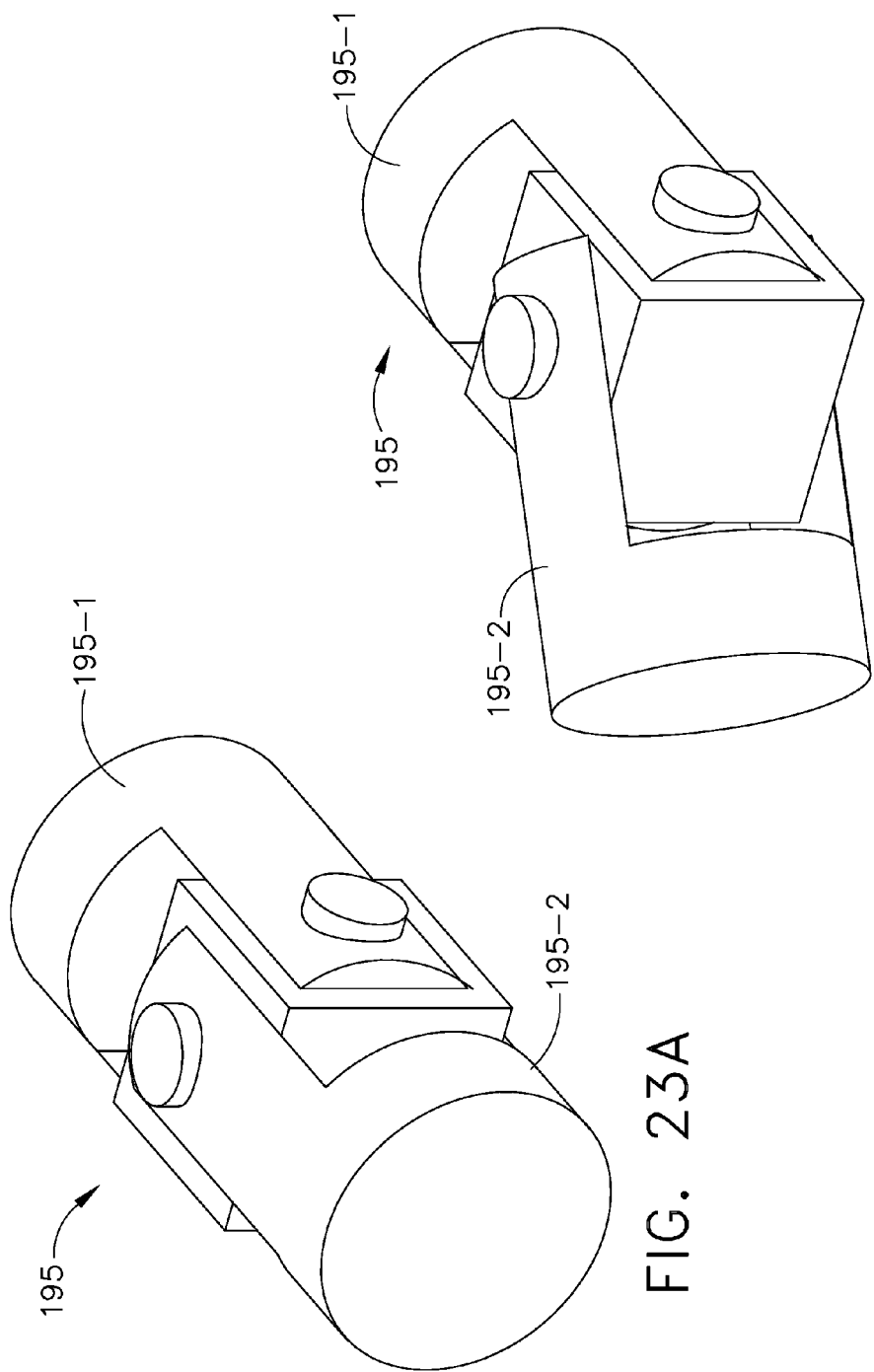

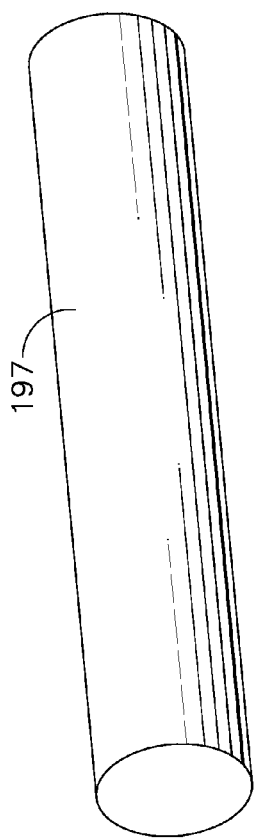
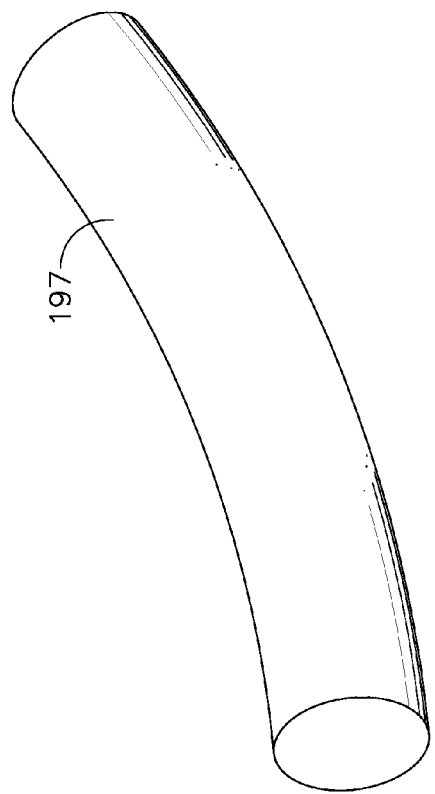
FIG. 24A
FIG. 24B

MOTOR-DRIVEN SURGICAL CUTTING AND FASTENING INSTRUMENT WITH MECHANICAL CLOSURE SYSTEM

CROSS-REFERENCE TO RELATED APPLICATIONS

The present application is related to the following concurrently-filed U.S. patent applications, which are incorporated herein by reference:

MOTOR-DRIVEN SURGICAL CUTTING AND FASTENING INSTRUMENT WITH USER FEEDBACK SYSTEM; Inventors: Frederick E. Shelton, IV, John Ouwerkerk and Jerome R. Morgan, Ser. No. 11/343,498

MOTOR-DRIVEN SURGICAL CUTTING AND FASTENING INSTRUMENT WITH LOADING FORCE FEEDBACK; Inventors: Frederick E. Shelton, IV, John N. Ouwerkerk, Jerome R. Morgan, and Jeffrey S. Swayze, Ser. No. 11/343,573

MOTOR-DRIVEN SURGICAL CUTTING AND FASTENING INSTRUMENT WITH TACTILE POSITION FEEDBACK; Inventors: Frederick E. Shelton, IV, John N. Ouwerkerk, Jerome R. Morgan, and Jeffrey S. Swayze, Ser. No. 11/344,035

MOTOR-DRIVEN SURGICAL CUTTING AND FASTENING INSTRUMENT WITH ADAPTIVE USER FEEDBACK; Inventors: Frederick E. Shelton, IV, John N. Ouwerkerk, and Jerome R. Morgan, Ser. No. 11/343,447

MOTOR-DRIVEN SURGICAL CUTTING AND FASTENING INSTRUMENT WITH ARTICULATABLE END EFFECTOR; Inventors: Frederick E. Shelton, IV and Christoph L. Gillum, Ser. No. 11/343,562

SURGICAL CUTTING AND FASTENING INSTRUMENT WITH CLOSURE TRIGGER LOCKING MECHANISM; Inventors: Frederick E. Shelton, IV and Kevin R. Doll, Ser. No. 11/343,321

GEARING SELECTOR FOR A POWERED SURGICAL CUTTING AND FASTENING STAPLING INSTRUMENT; Inventors: Frederick E. Shelton, IV, Jeffrey S. Swayze, Eugene L. Timperman, Ser. No. 11/343,563

SURGICAL INSTRUMENT HAVING RECORDING CAPABILITIES; Inventors: Frederick E. Shelton, IV, John N. Ouwerkerk, and Eugene L. Timperman, Ser. No. 11/343,803

SURGICAL INSTRUMENT HAVING A REMOVABLE BATTERY; Inventors: Frederick E. Shelton, IV, Kevin R. Doll, Jeffrey S. Swayze and Eugene Timperman, Ser. No. 11/344,020

ELECTRONIC LOCKOUTS AND SURGICAL INSTRUMENT INCLUDING SAME; Inventors: Jeffrey S. Swayze, Frederick E. Shelton, IV, Kevin R. Doll, Ser. No. 11/343,439

ENDOSCOPIC SURGICAL INSTRUMENT WITH A HANDLE THAT CAN ARTICULATE WITH RESPECT TO THE SHAFT; Inventors: Frederick E. Shelton, IV, Jeffrey S. Swayze, Mark S. Ortiz, and Leslie M. Fugikawa, Ser. No. 11/343,547

ELECTRO-MECHANICAL SURGICAL CUTTING AND FASTENING INSTRUMENT HAVING A ROTARY FIRING AND CLOSURE SYSTEM WITH PARALLEL CLOSURE AND ANVIL ALIGNMENT COMPONENTS; Inventors: Frederick E. Shelton, IV, Stephen J. Balek and Eugene L. Timperman, Ser. No. 11/344,021

DISPOSABLE STAPLE CARTRIDGE HAVING AN ANVIL WITH TISSUE LOCATOR FOR USE WITH A SURGICAL CUTTING AND FASTENING INSTRUMENT AND MODULAR END EFFECTOR SYSTEM THEREFOR; Inventors: Frederick E. Shelton, IV, Michael S. Cropper, Joshua M. Broehl, Ryan S. Crisp, Jamison J. Float, Eugene L. Timperman, Ser. No. 11/343,546

SURGICAL INSTRUMENT HAVING A FEEDBACK SYSTEM; Inventors: Frederick E. Shelton, IV, Jerome R. Morgan, Kevin R. Doll, Jeffrey S. Swayze and Eugene Timperman, Ser. No. 11/343,545

BACKGROUND

The present invention generally concerns surgical cutting and fastening instruments and, more particularly, motor-driven surgical cutting and fastening instruments.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, or multiple firing strokes, depending on the device. Firing the surgical stapler causes severing and stapling the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest for lower force-to-fire (FTF) to a level that all or a great majority of surgeons can handle. One known solution to lower FTF it use $CO_2$ or electrical motors. These devices have not faired much better than traditional hand-powered devices, but for a different reason. Surgeons typically prefer to experience proportionate force distribution to that being experienced by the end-effector in the forming the staple to assure them that the cutting/stapling cycle is complete, with the upper limit within the capabilities of most surgeons (usually around 15-30 lbs). They also typically want to maintain control of deploying the staple and being able to stop at anytime if the forces felt in the handle of the device feel too great or for some other clinical reason. These user-feedback effects are not suitably realizable in present motor-driven endocutters. As a result, there is a general lack of acceptance by physicians of motor-drive endocutters where the cutting/stapling operation is actuated by merely pressing a button.

SUMMARY

In one general aspect, the present invention is directed to a motorized surgical cutting and fastening instrument that provides feedback to the user regarding the position, force and/or deployment of the end effector. The instrument, in various embodiments, also allows the operator to control the end effector, including being able to stop deployment if so desired. The instrument may include two triggers in its handle—a closure trigger and a firing trigger—with separate actuation motions. When an operator of the instrument retracts the closure trigger, tissue positioned in the end effector may be clamped by the end effector. Then, when the operator retracts the firing trigger, a motor may power, via a gear drive train, a rotational main drive shaft assembly, which causes a cutting instrument in the end effector to severe the clamped tissue.

In various embodiments, the instrument may comprise a power assist system with loading force feedback and control to reduce the firing force required to be exerted by the operator in order to complete the cutting operation. In such embodiments, the firing trigger may be geared into the gear drive train of the main drive shaft assembly. In that way, the operator may experience feedback regarding the force being applied to the cutting instrument. That is, the loading force on the firing trigger may be related to the loading force experienced by the cutting instrument. Also in such embodiments, because the firing trigger is geared into the gear drive train, force applied by the operator may be added to the force applied to the motor.

According to various embodiments, when the firing trigger is retracted an appropriate amount (e.g., five degrees), an on/off switch may be actuated, which sends a signal to the motor to rotate at a specified rate, thus commencing actuation of the drive shaft assembly and end effector. According to other embodiments, a proportional sensor may be used. The proportional sensor may send a signal to the motor to rotate at a rate proportional to the force applied to the firing trigger by the operator. In that way, the rotational position of the firing trigger is generally proportional to where the cutting instrument is in the end effector (e.g., fully deployed or fully retracted). Further, the operator could stop retracting the firing trigger at some point in the stroke to stop the motor, and thereby stop the cutting motion. In addition, sensors may be used to detect the beginning of the stroke of the end effector (e.g., fully retracted position) and the end of the stroke (e.g., fully deployed position), respectively. Consequently, the sensors may provide an adaptive control system for controlling end effector deployment that is outside of the closed loop system of the motor, gear drive train, and end effector.

In other embodiments, the firing trigger may not be directly geared into the gear drive train used to actuate the end effector. In such embodiments, a second motor may be used to apply forces to the firing trigger to simulate the deployment of the cutting instrument in the end effector. The second motor may be controlled based on incremental rotations of the main drive shaft assembly, which may be measured by a rotary encoder. In such embodiment, the position of the rotational position of the firing trigger may be related to the position of the cutting instrument in the end effector. Additionally, an on/off switch or a proportional switch may be used to control the main motor (i.e., the motor that powers the main drive shaft).

In various implementations, the end effector may use a helical drive screw in the base of the end effector to drive the cutting instrument (e.g., knife). Also, the end effector may include a staple cartridge for stapling the severed tissue. According to other embodiments, other means for fastening (or sealing) the severed tissue may be used, including RF energy and adhesives.

Also, the instrument may include a mechanical closure system. The mechanical closure system may include an elongate channel having a clamping member, such as an anvil, pivotably connected to the channel to clamp tissue positioned in the end effector. The user may activate the clamping action of the end effector by retracting the closer trigger, which, through a mechanical closure system, causes the clamping action of the end effector. Once the clamping member is locked in place, the operator may activate the cutting operation by retracting the separate firing trigger. This may cause the cutting instrument to travel longitudinally along the channel in order to cut tissue clamped by the end effector.

In various implementations, the instrument may include a rotational main drive shaft assembly for actuating the end effector. Further, the main drive shaft may comprise an articulating joint such that the end effector may be articulated. The articulation joint may comprise, for example, a bevel gear assembly, a universal joint, or a flexible torsion cable capable of transmitting torsion force to the end effector.

Other aspects of the present invention are directed to various mechanisms for locking the closure trigger to a lower, pistol-grip portion of the handle. Such embodiments free up space in the handle directly above and behind the triggers for other components of the instrument, including components of the gear drive train and the mechanical closure system.

DRAWINGS

Various embodiments of the present invention are described herein by way of example in conjunction with the following figures, wherein FIGS. 1 and 2 are perspective views of a surgical cutting and fastening instrument according to various embodiments of the present invention;

Figure 41:
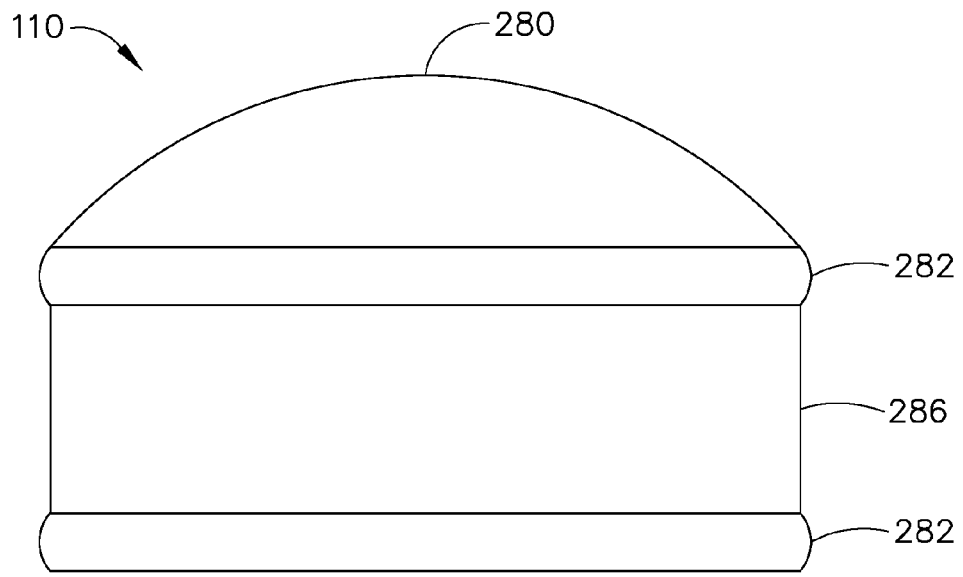
Figure 42:
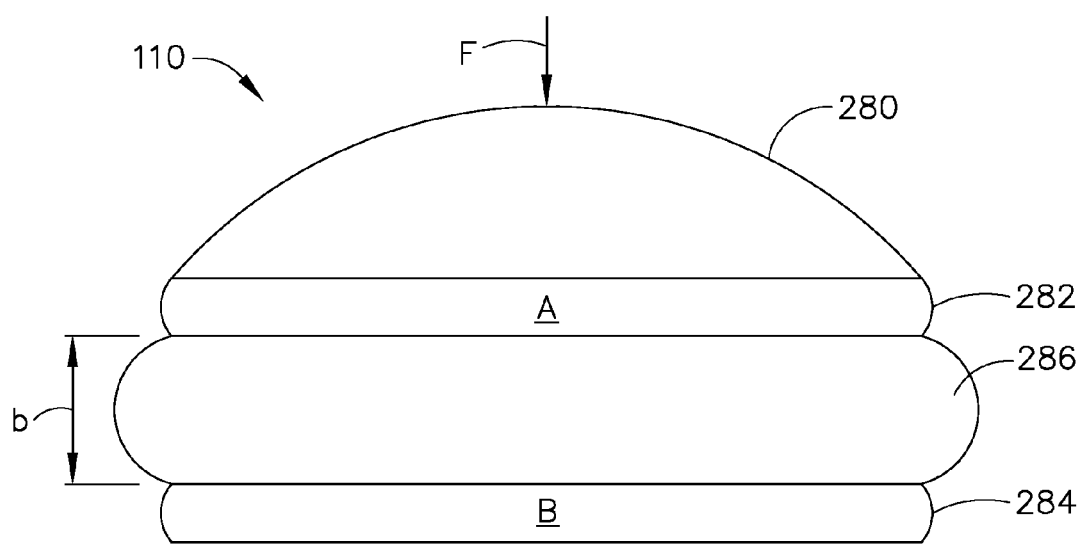

FIGS. 23A-B show a universal joint ("u-joint") that may be employed at the articulation point of the instrument according to various embodiments of the present invention;

FIGS. 24A-B shows a torsion cable that may be employed at the articulation point of the instrument according to various embodiments of the present invention;

FIGS. 25-31 illustrate a surgical cutting and fastening instrument with power assist according to another embodiment of the present invention;

FIGS. 32-36 illustrate a surgical cutting and fastening instrument with power assist according to yet another embodiment of the present invention;

FIGS. 37-40 illustrate a surgical cutting and fastening instrument with tactile feedback to embodiments of the present invention; and FIGS. 41-42 illustrate a proportional sensor that may be used according to various embodiments of the present invention.

DETAILED DESCRIPTION

Figure 1:
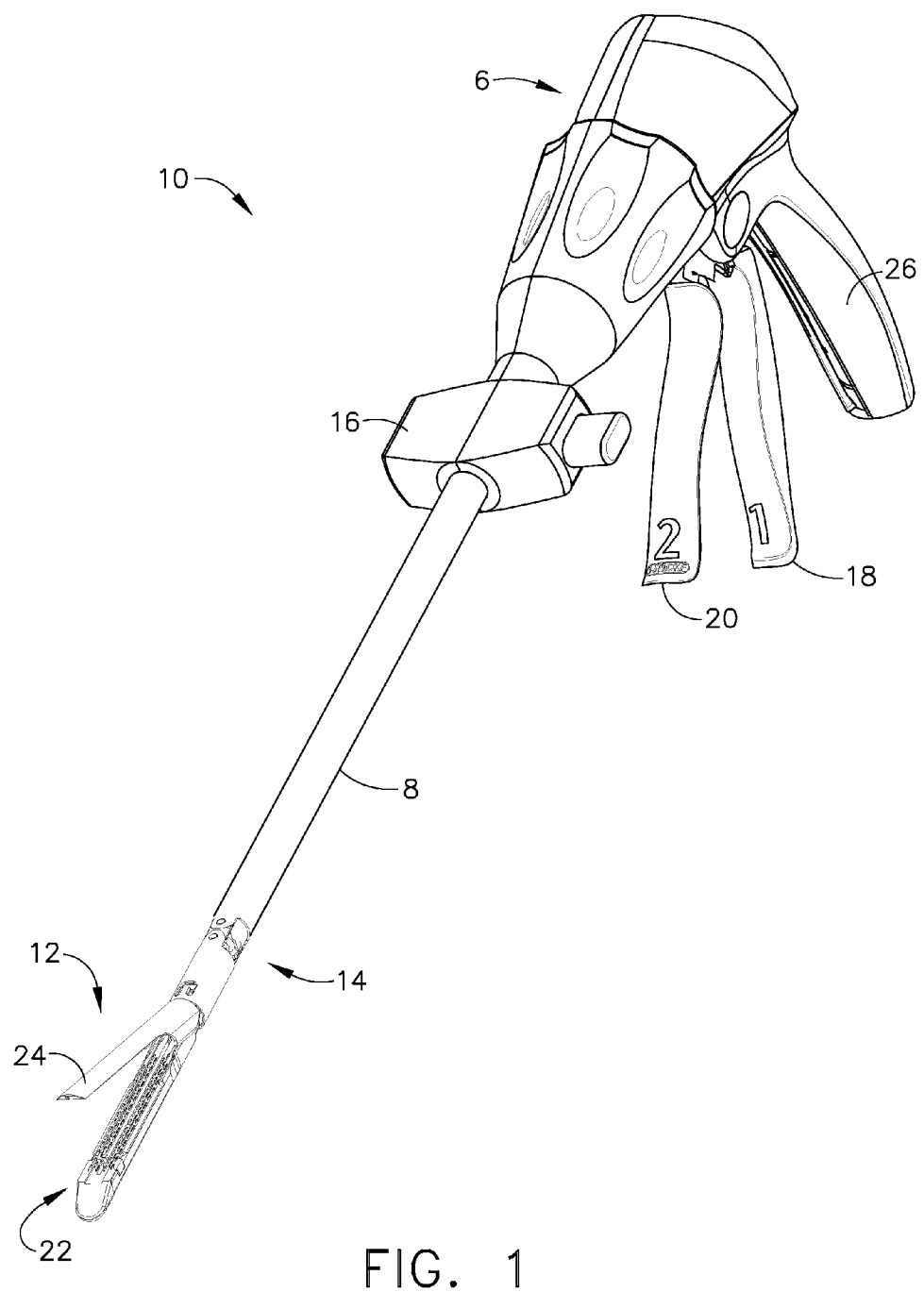
Figure 2:
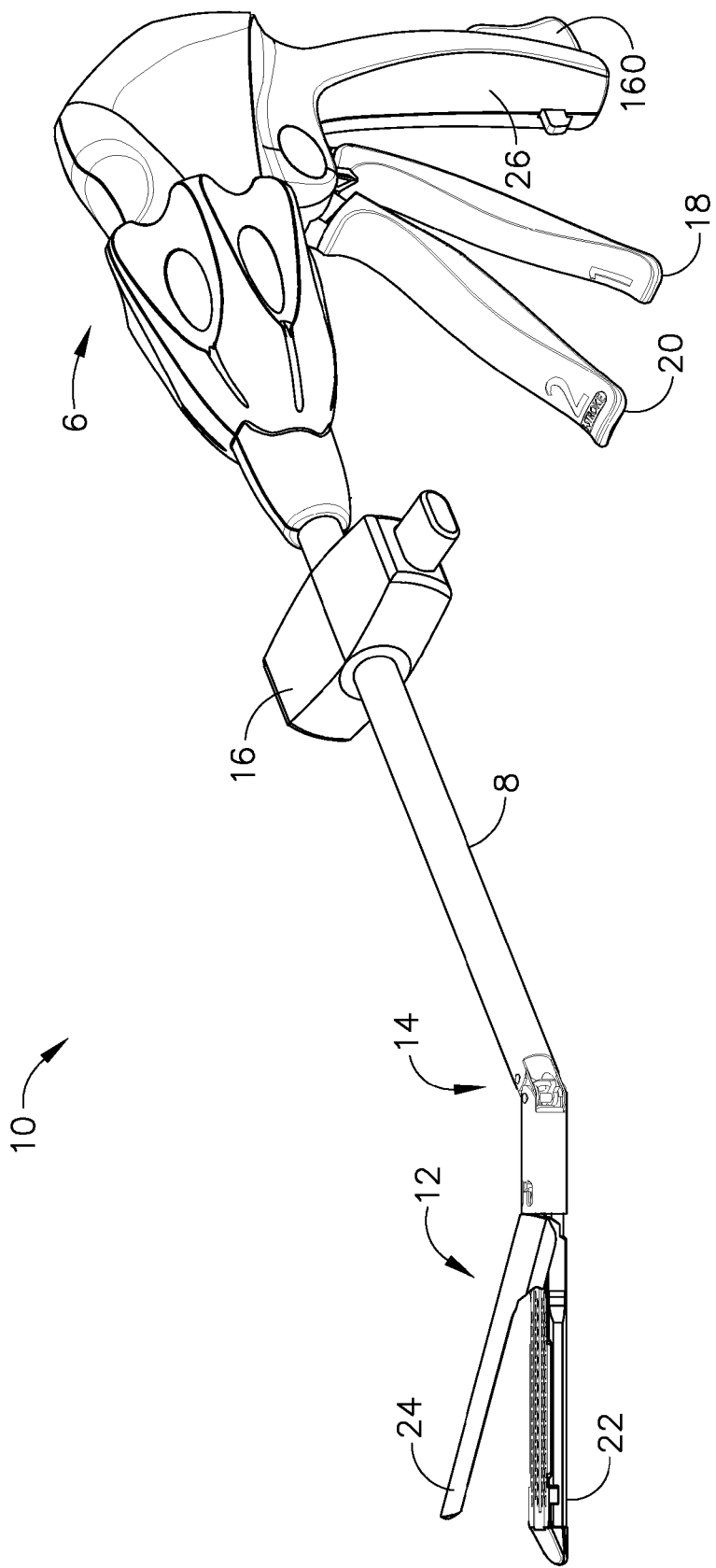

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, as a slide release button 160 shown in FIG. 14, and/or button 172 shown in FIG. 16.

Figure 3:
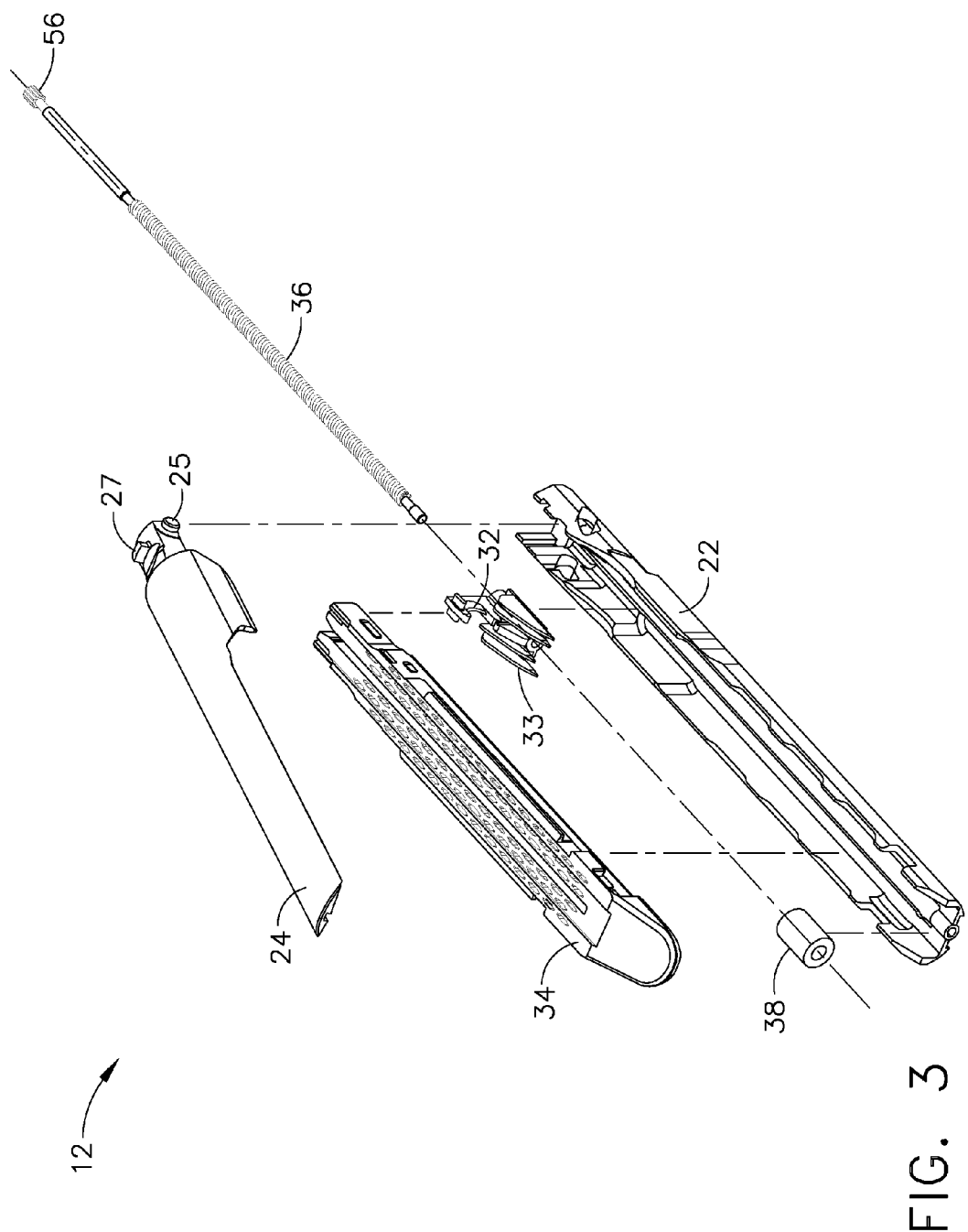
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled "Surgical stapling instrument incorporating an E-beam firing mechanism," which is incorporated herein by reference, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTROSURGICAL HEMOSTATIC DEVICE WITH RECESSED AND/OR OFFSET ELECTRODES" to Yates et al., which are incorporated herein by reference, disclose an endoscopic cutting instrument that uses RF energy to seal the severed tissue. U.S. patent application Ser. No. 11/267,811 to Jerome R. Morgan, et. al, and U.S. patent application Ser. No. 11/267,383 to Frederick E. Shelton, IV, et. al., which are also incorporated herein by reference, disclose an endoscopic cutting instrument that uses adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
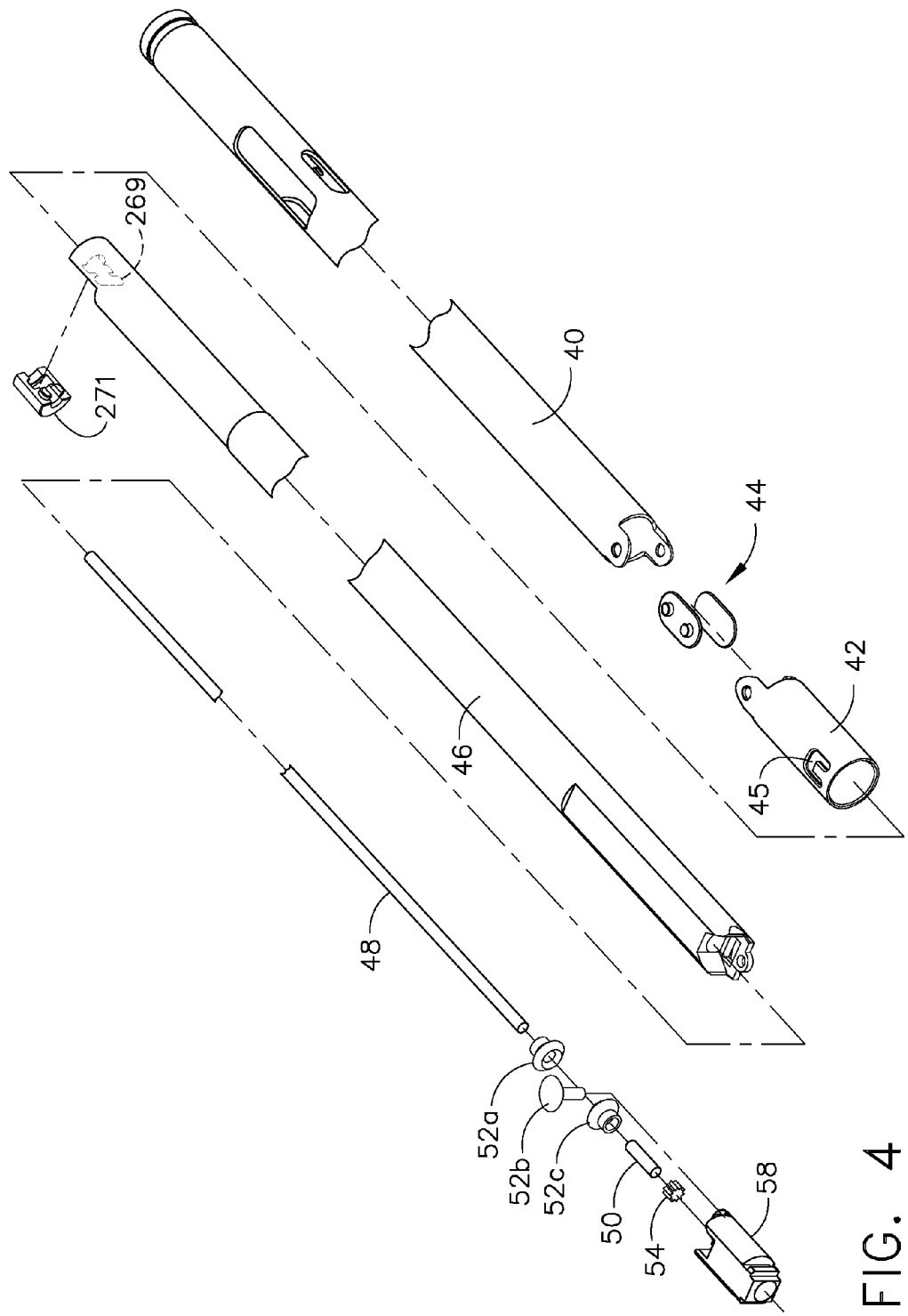
Figure 5:
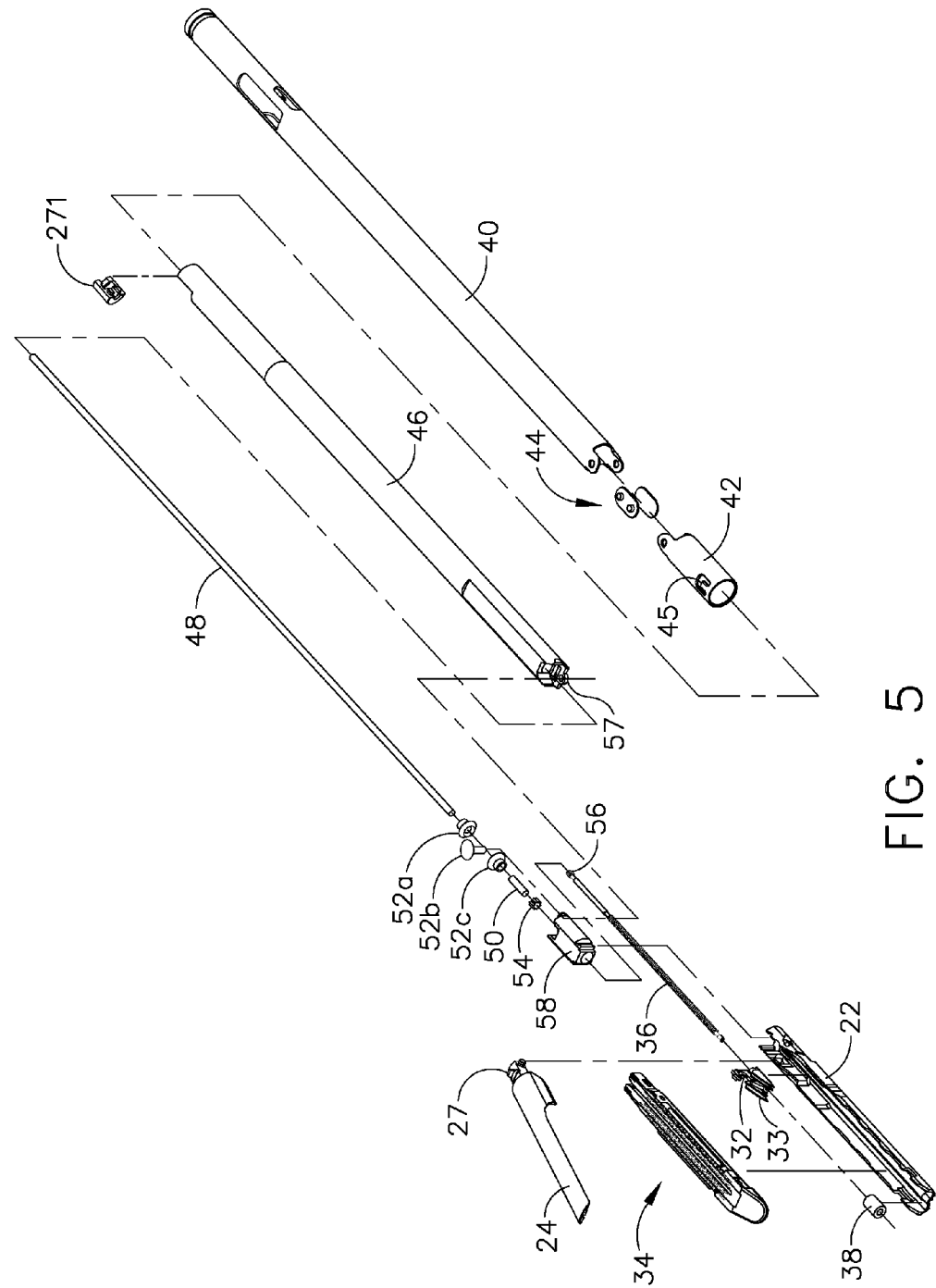
Figure 6:
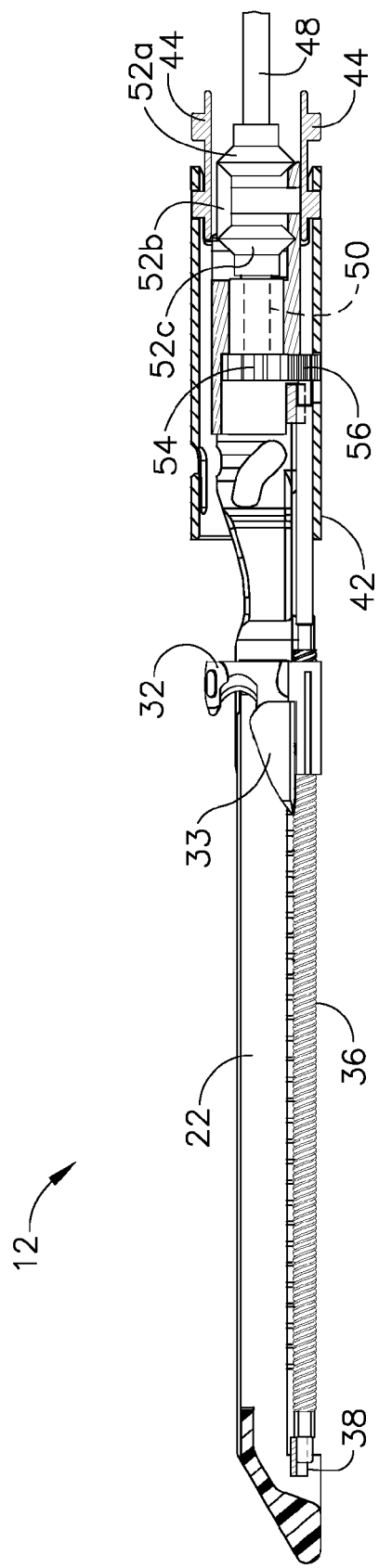
FIG. 6 is a side view of the end effector according to various embodiments of the present invention.
Figure 7:
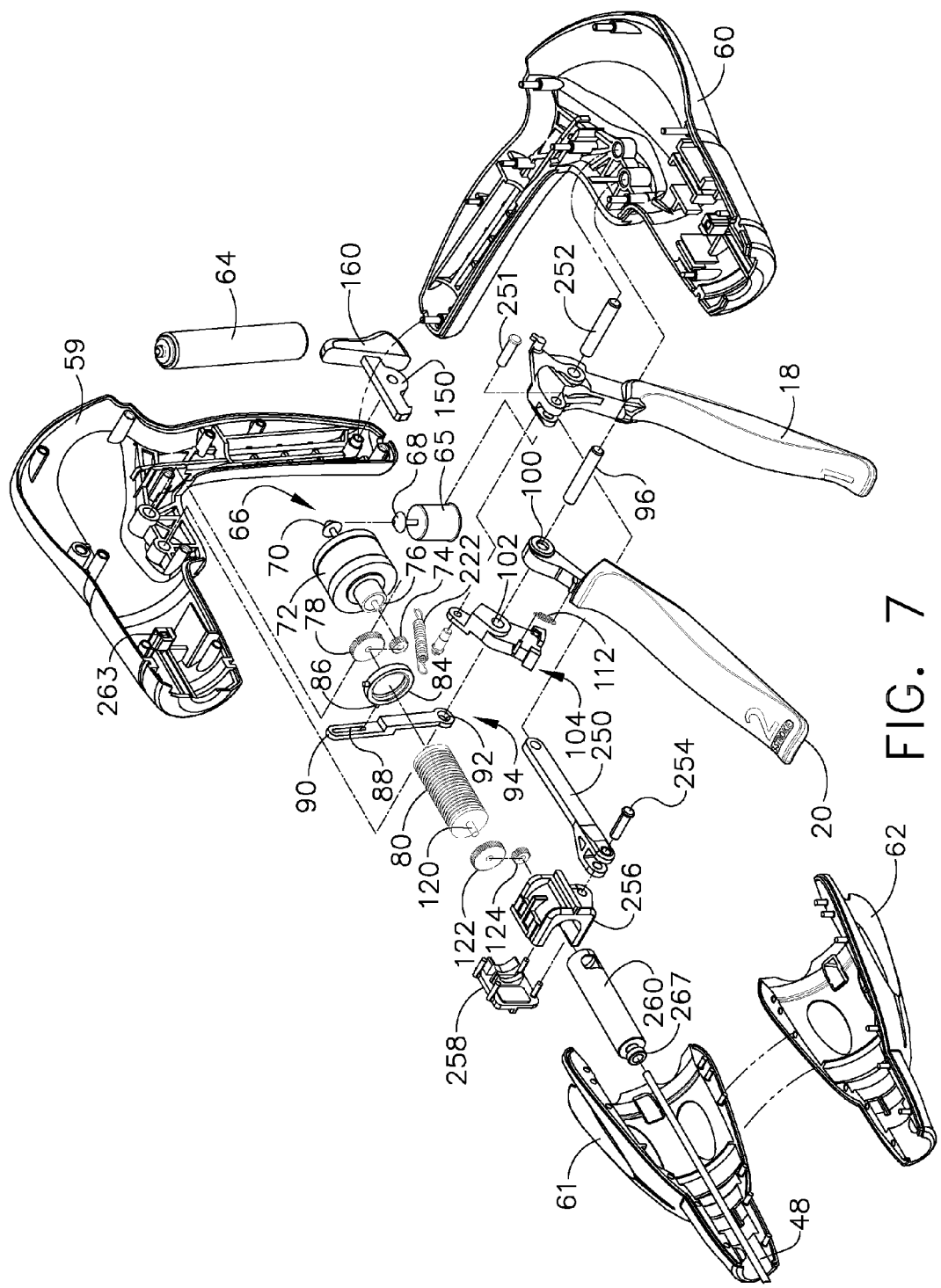
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverse the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

As described above, because of the lack of user feedback for the cutting/stapling operation, there is a general lack of acceptance among physicians of motor-driven endocutters where the cutting/stapling operation is actuated by merely pressing a button. In contrast, embodiments of the present invention provide a motor-driven endocutter with user-feedback of the deployment, force, and/or position of the cutting instrument in the end effector.

FIGS. 7-10 illustrate an exemplary embodiment of a motor-driven endocutter, and in particular the handle thereof, that provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 110, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
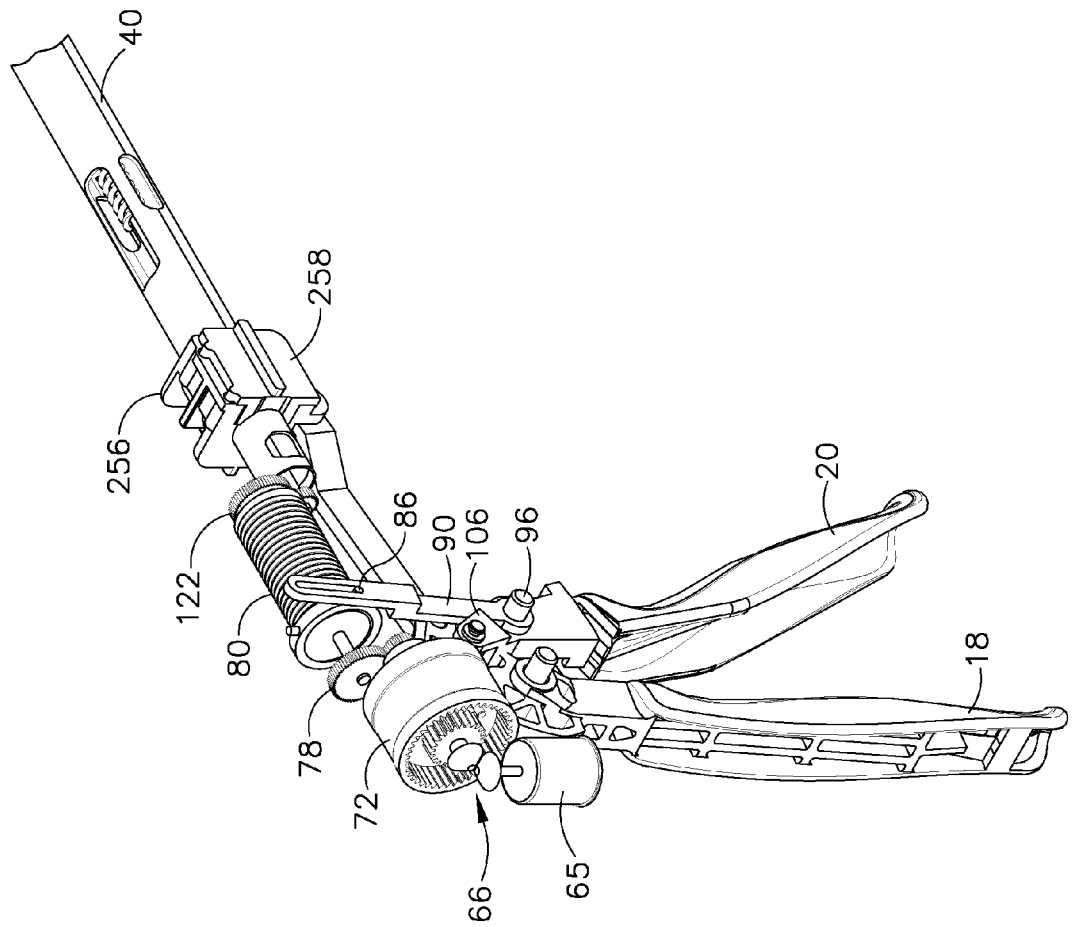
FIGS. 8 and 9 are partial perspective views of the handle according to various embodiments of the present invention.
Figure 9:
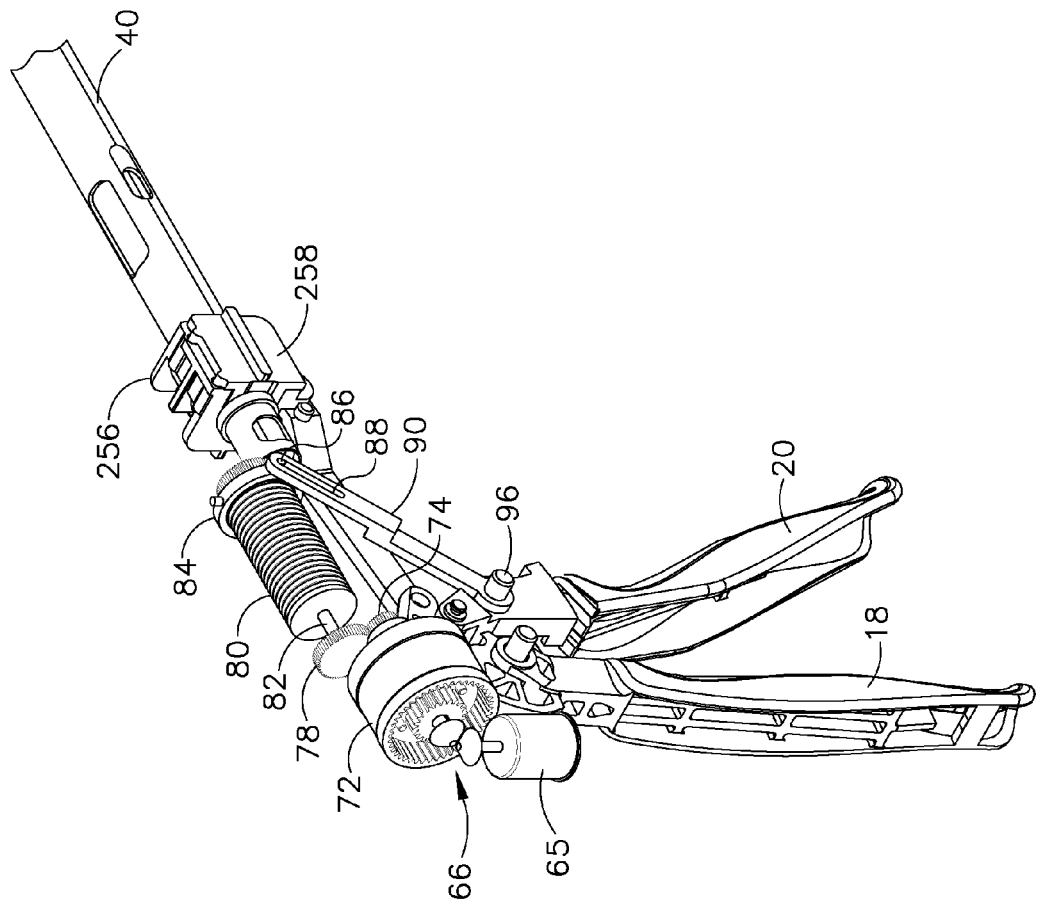
Figure 10:
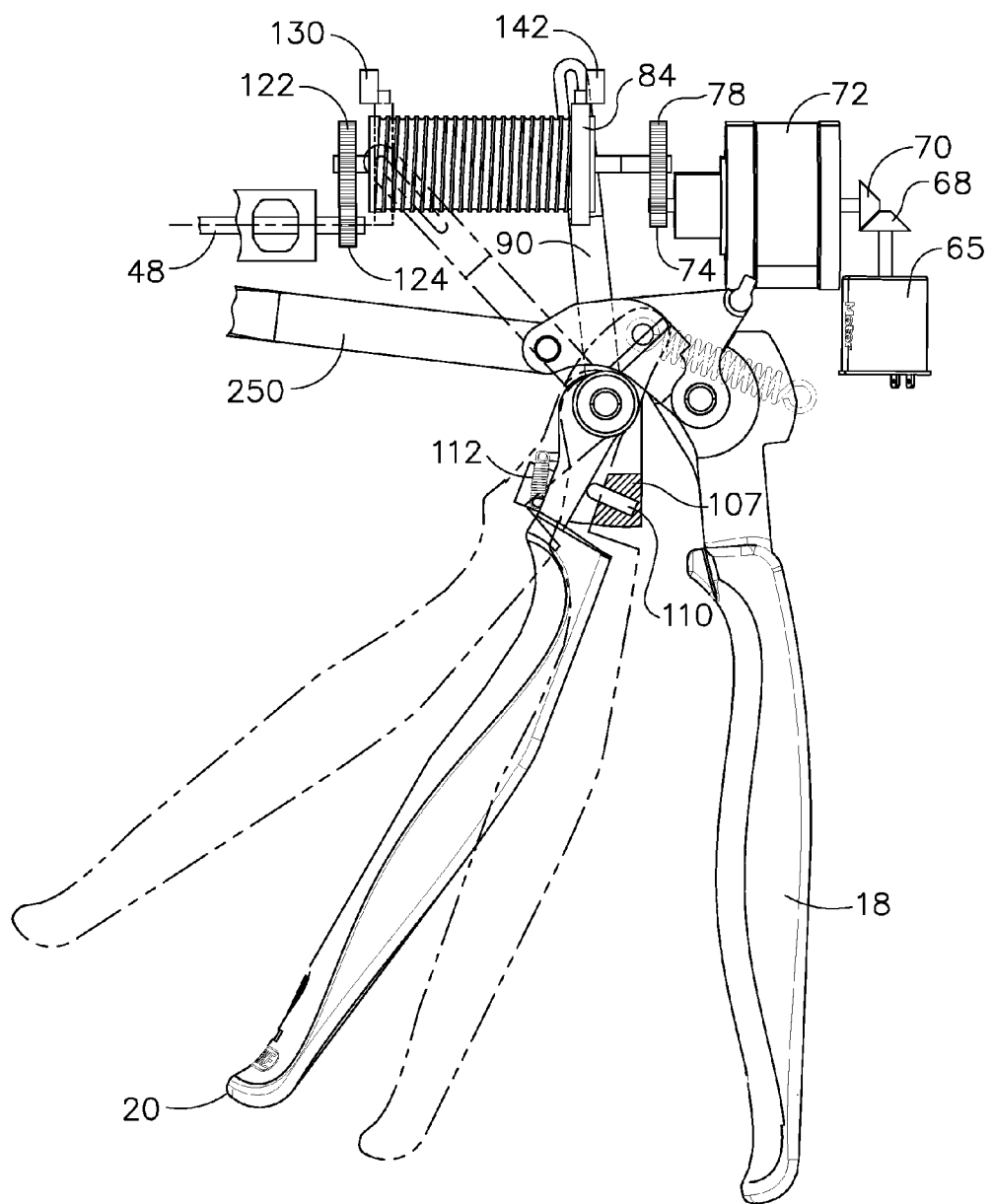
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

FIGS. 41 and 42 illustrate two states of a variable sensor that may be used as the run motor sensor 110 according to various embodiments of the present invention. The sensor 110 may include a face portion 280, a first electrode (A) 282, a second electrode (B) 284, and a compressible dielectric material 286 (e.g., EAP) between the electrodes 282, 284. The sensor 110 may be positioned such that the face portion 280 contacts the firing trigger 20 when retracted. Accordingly, when the firing trigger 20 is retracted, the dielectric material 286 is compressed, as shown in FIG. 42, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric 286 is compressed due to retraction of the firing trigger 20 (denoted as force "F" in FIG. 42) is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
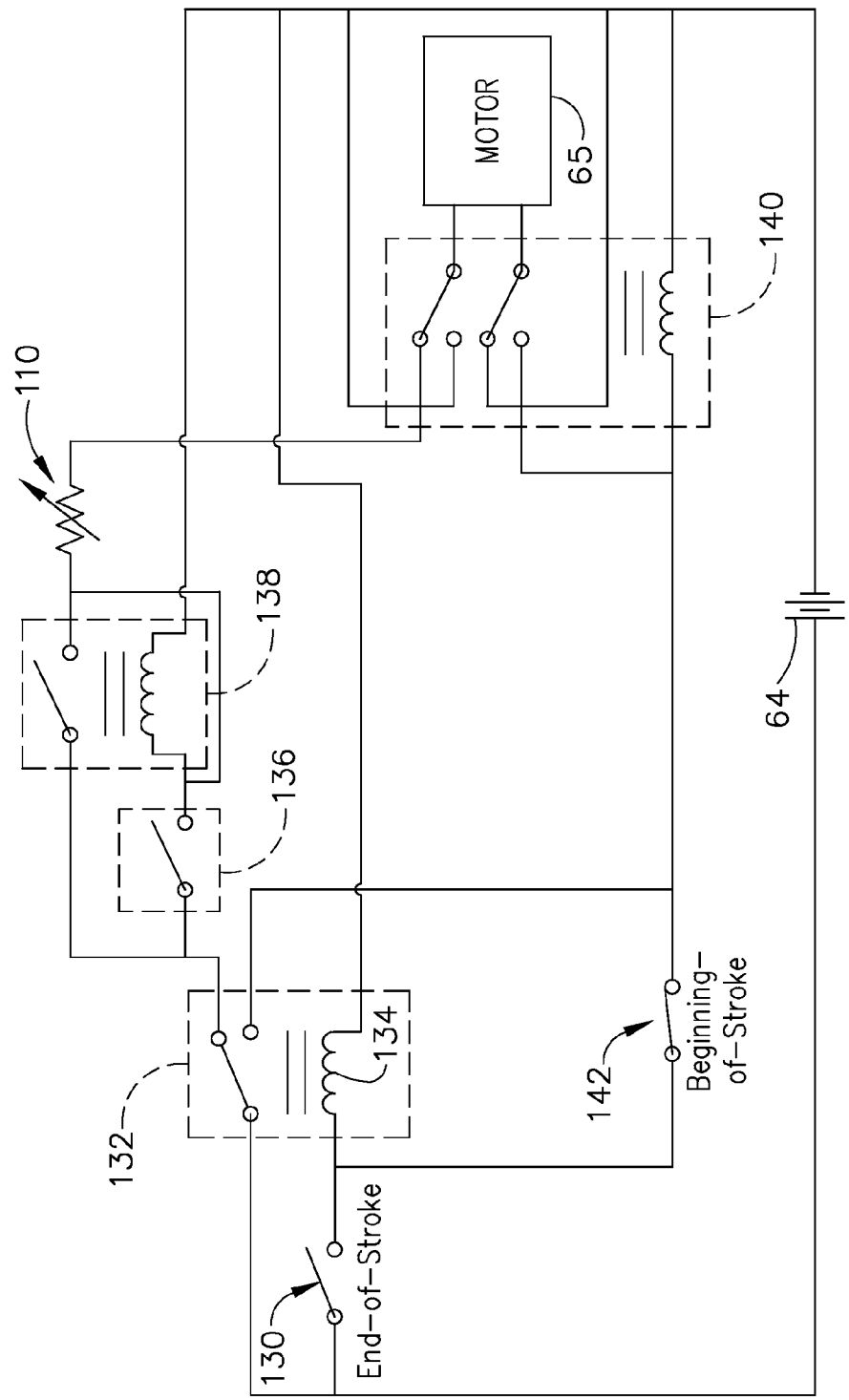
FIG. 11 is a schematic diagram of a circuit used in the instrument according to various embodiments of the present invention.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 132. This causes the relay 132 to assume its energized state (not shown in FIG. 13), which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction.

Because the stop motor sensor switch 142 is normally-closed, current will flow back to the relay 132 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
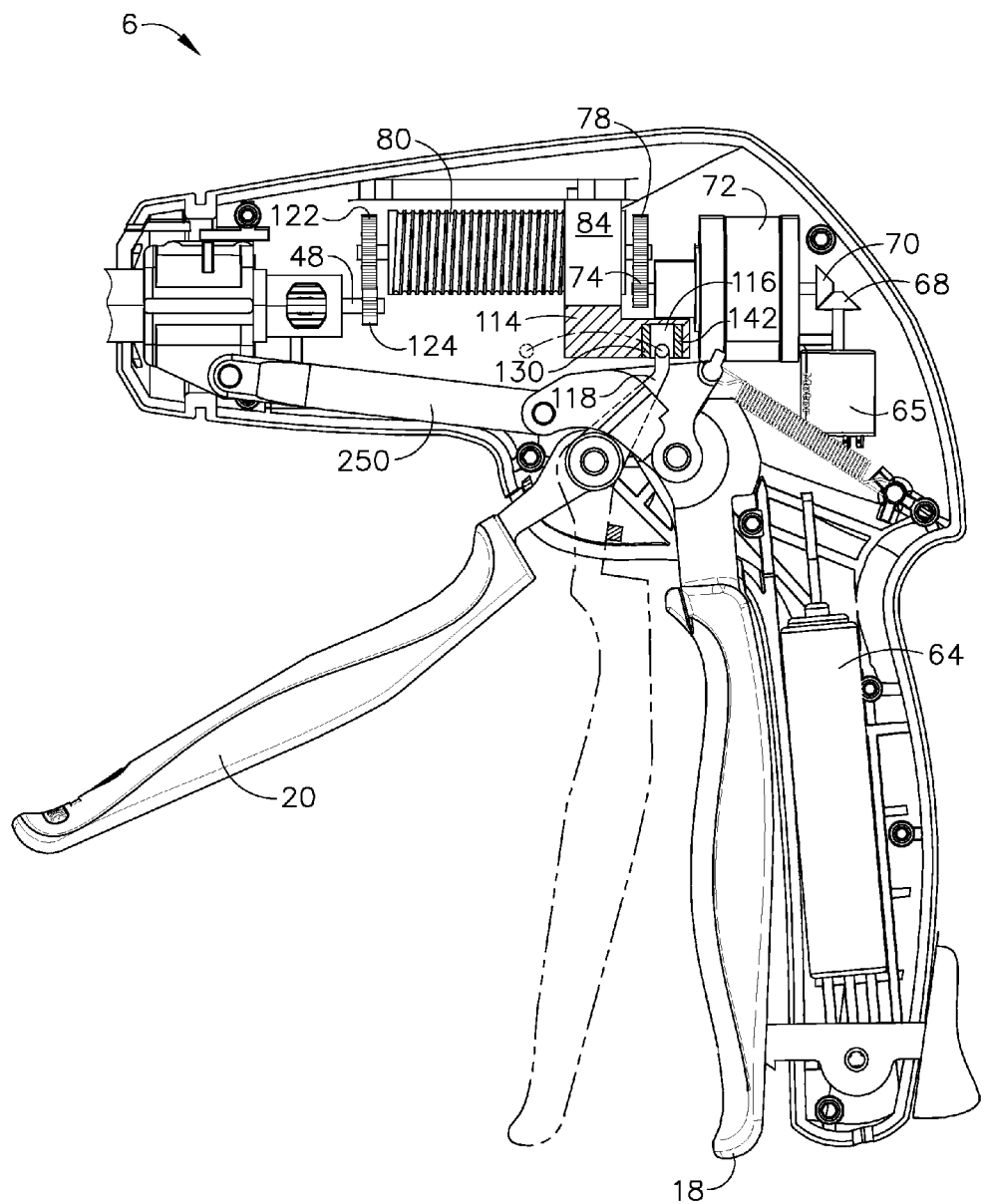
FIGS. 12-13 are side views of the handle according to other embodiments of the present invention.

FIG. 12 is a side-view of the handle 6 of a power-assist motorized endocutter according to another embodiment. The embodiment of FIG. 12 is similar to that of FIGS. 7-10 except that in the embodiment of FIG. 12, there is not slotted arm connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximate end of the notch 116. As the ring 84 moves down the helical gear drum 80 (and back), the sensor portion 114 moves with it. Further, as shown in FIG. 12, the middle piece 104 may have an arm 118 that extends into the notch 12.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate CCW with the firing trigger 20 due to the forward motion stop 107 that engages the firing trigger 20. The CCW rotation of the middle piece 104 cause the arm 118 to rotate CCW with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximate end of the helical gear drum 80, the arm will contact and thereby trip the stop motor sensor 142. Such actions may reverse and stop the motor 65, respectively, as described above.

Figure 13:
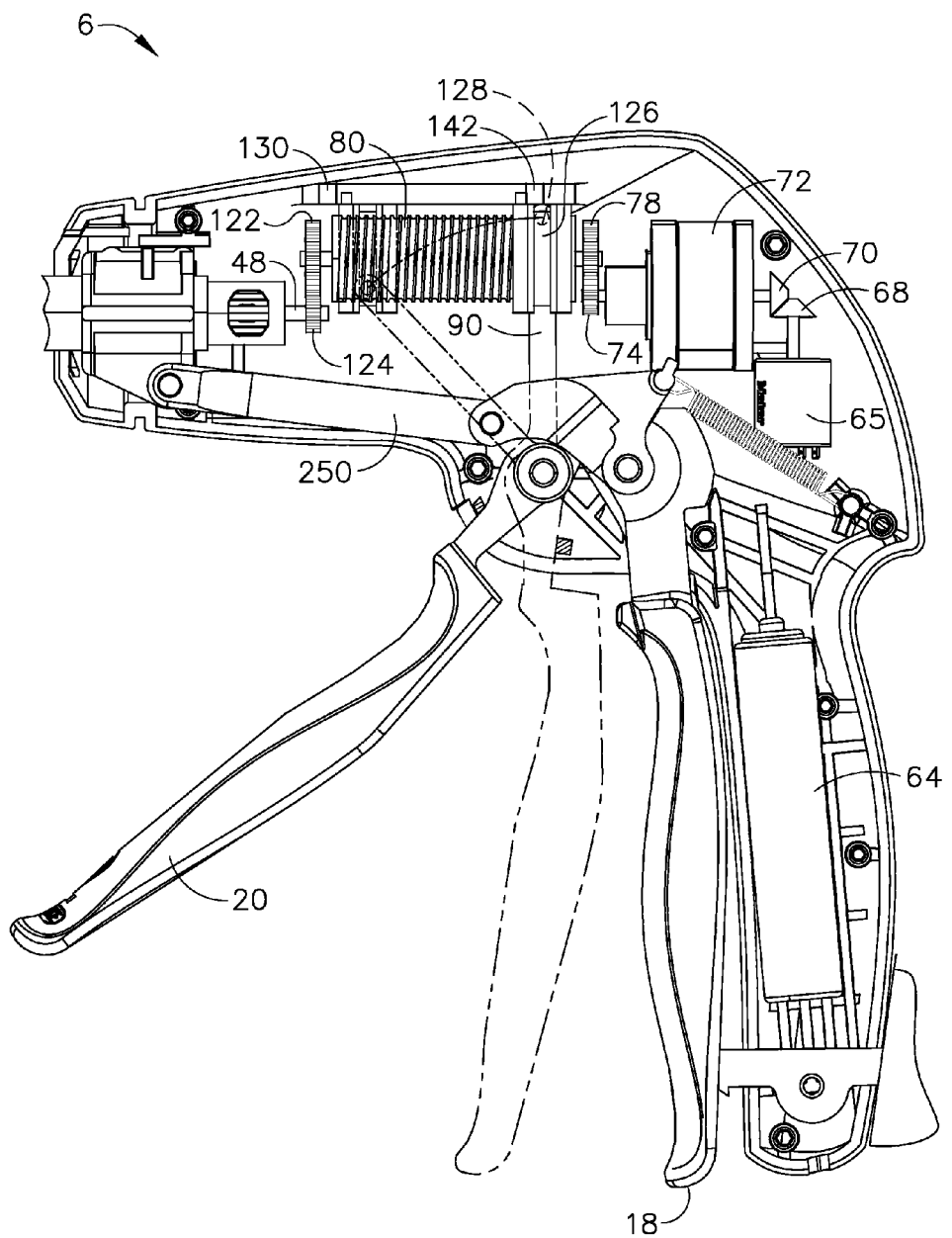

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90. Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates CCW as the ring 84 advances due to the post 128 being disposed in the channel 126, as shown in FIG. 13.

Figure 14:
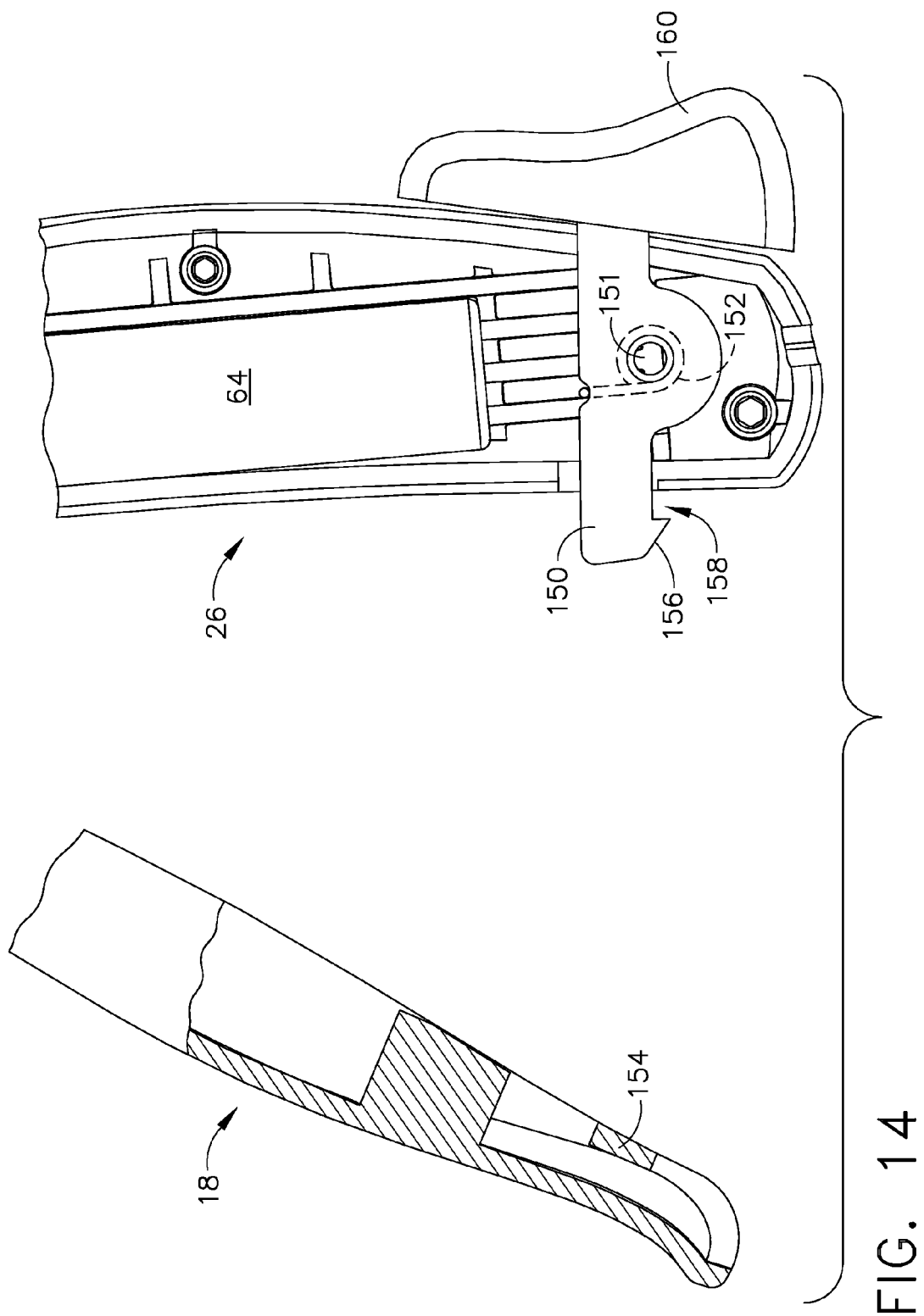
FIGS. 14-22 illustrate different mechanisms for locking the closure trigger according to various embodiments of the present invention.
Figure 15:
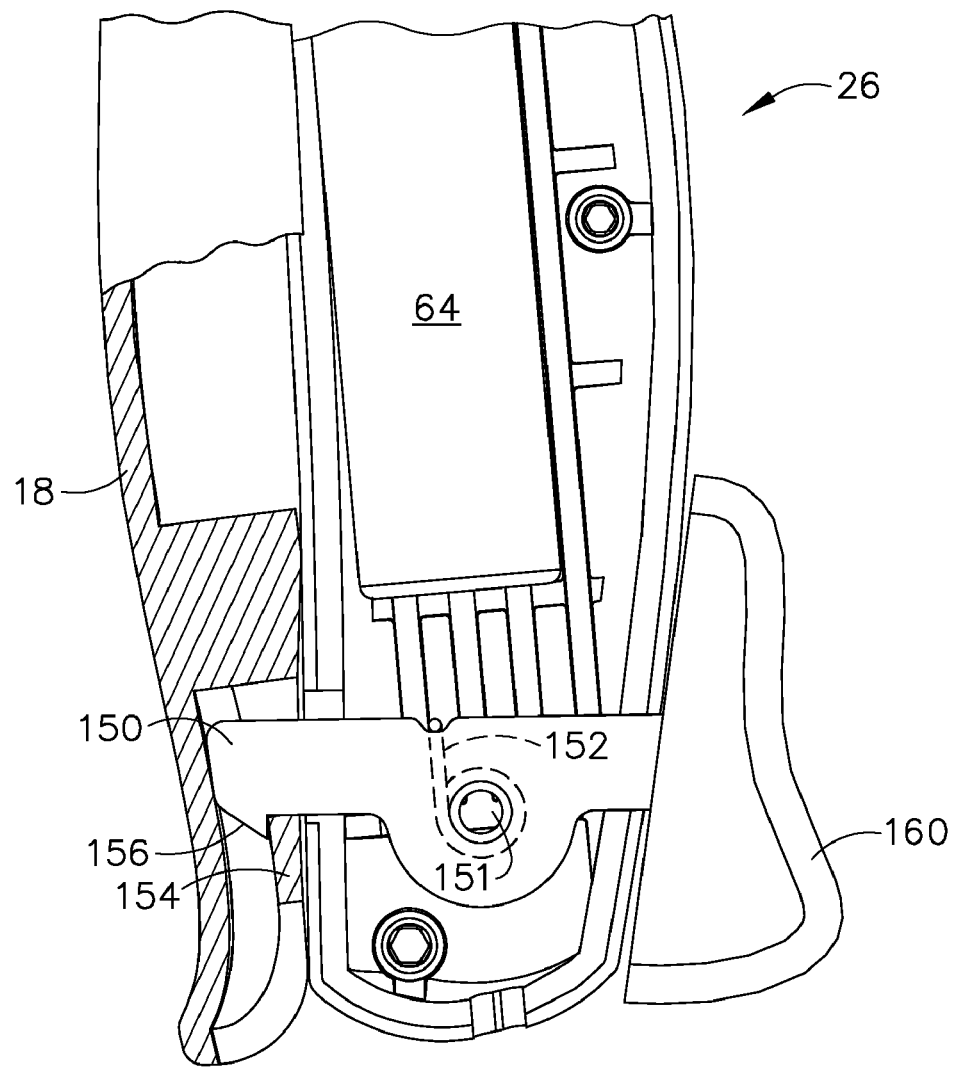

As mentioned above, in using a two-stroke motorized instrument, the operator first pulls back and locks the closure trigger 18. FIGS. 14 and 15 show one embodiment of a way to lock the closure trigger 18 to the pistol grip portion 26 of the handle 6. In the illustrated embodiment, the pistol grip portion 26 includes a hook 150 that is biased to rotate CCW about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or CW in FIGS. 12-13) until the closure bar 154 completely passes the sloped portion 156 passes into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 CW such that the closure bar 154 is released from the recessed notch 158.

Figure 16:
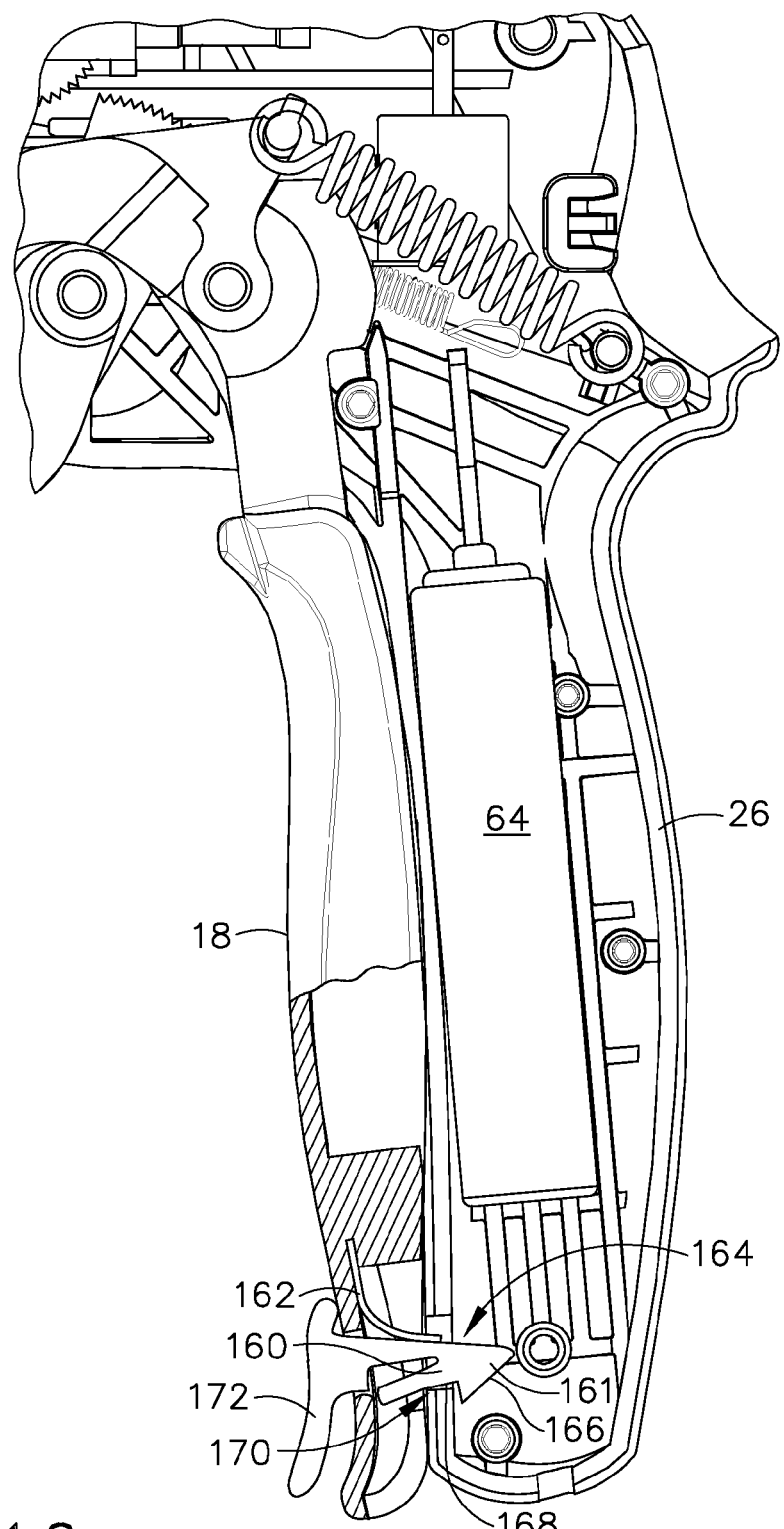

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or CW) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate CCW. Eventually the lower chamfered surface 166 fully passes the lower sidewall 168, removing the CCW force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate CCW and allowing the arrow-head portion 161 to slide out of the opening 164.

Figure 17:
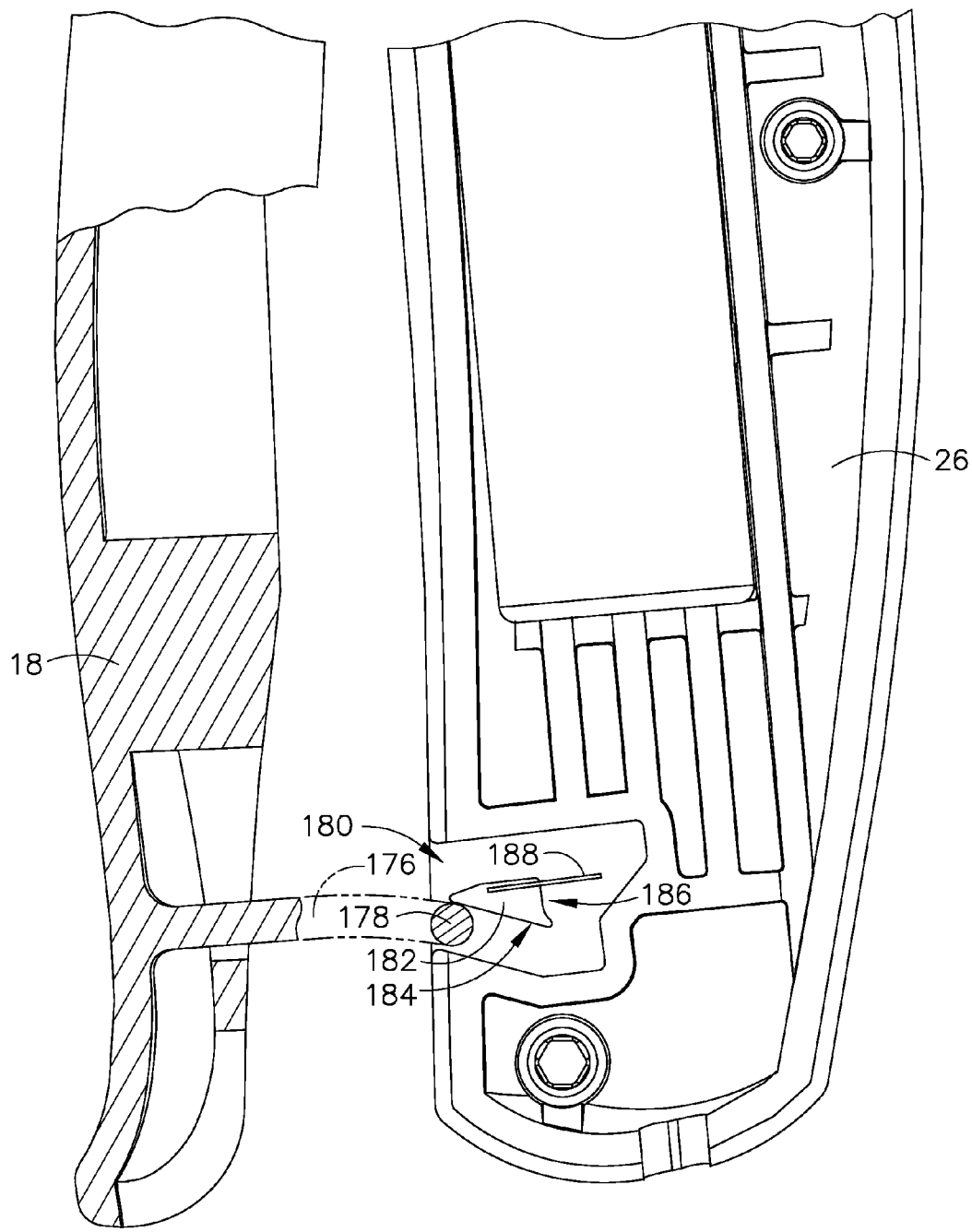
Figure 18:
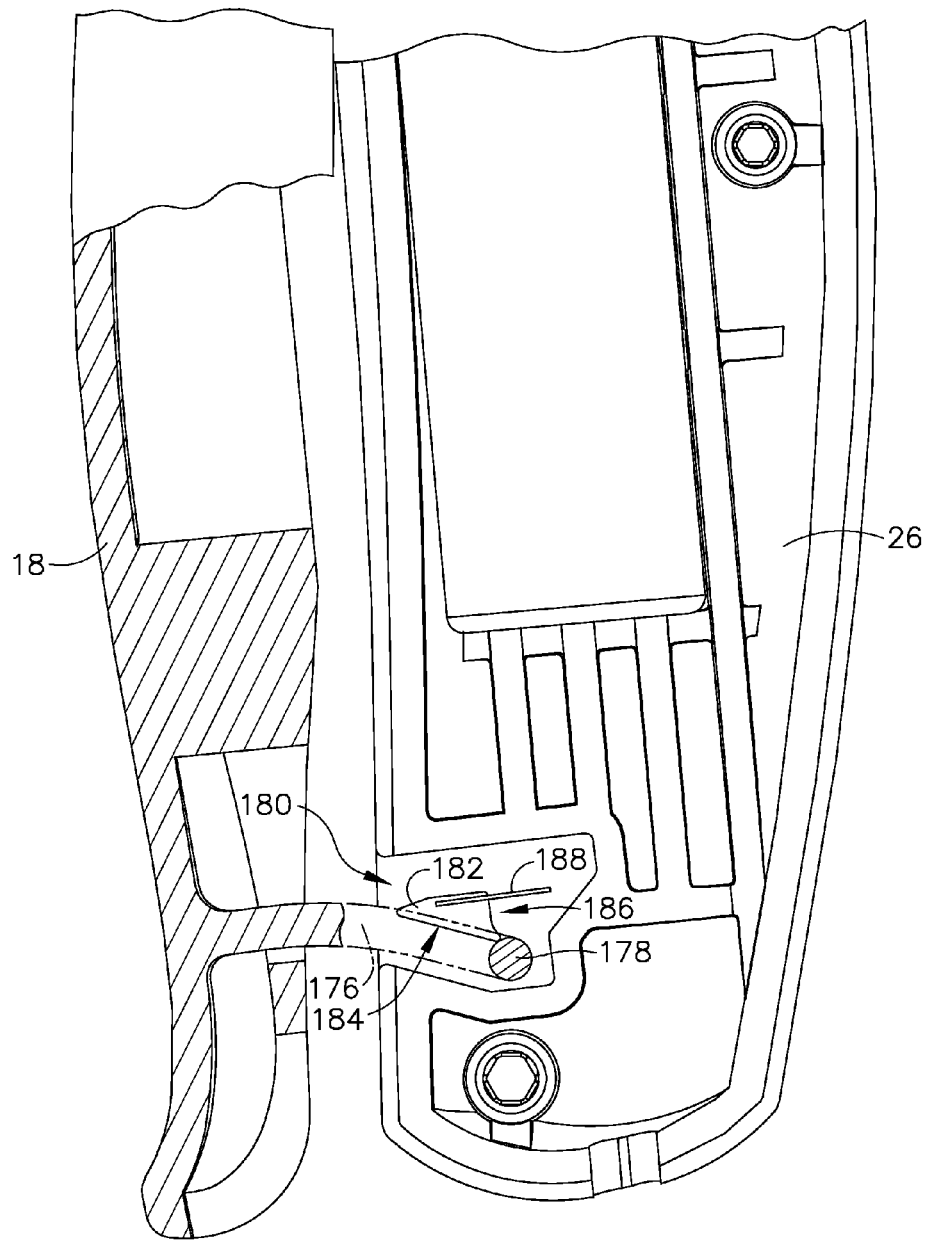
Figure 19:
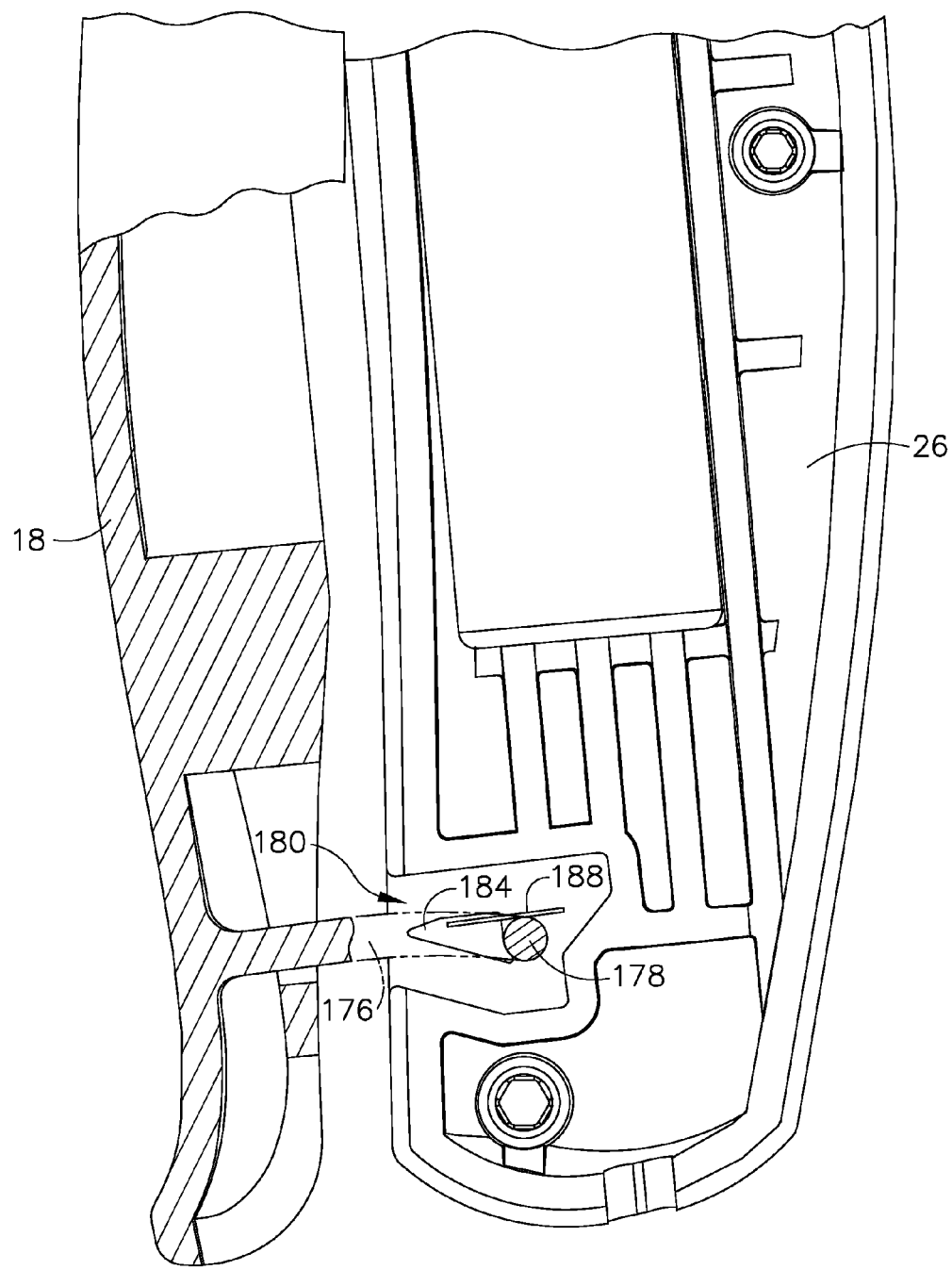

FIGS. 17-22 show a closure trigger locking mechanism according to another embodiment. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (i.e., the arm 176 is rotated CW) by the lower surface 184 of the wedge 182, as shown in FIGS. 17 and 18. When the pin 178 fully passes the lower surface 184, the CW force on the arm 176 is removed, and the pin 178 is rotated CCW such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
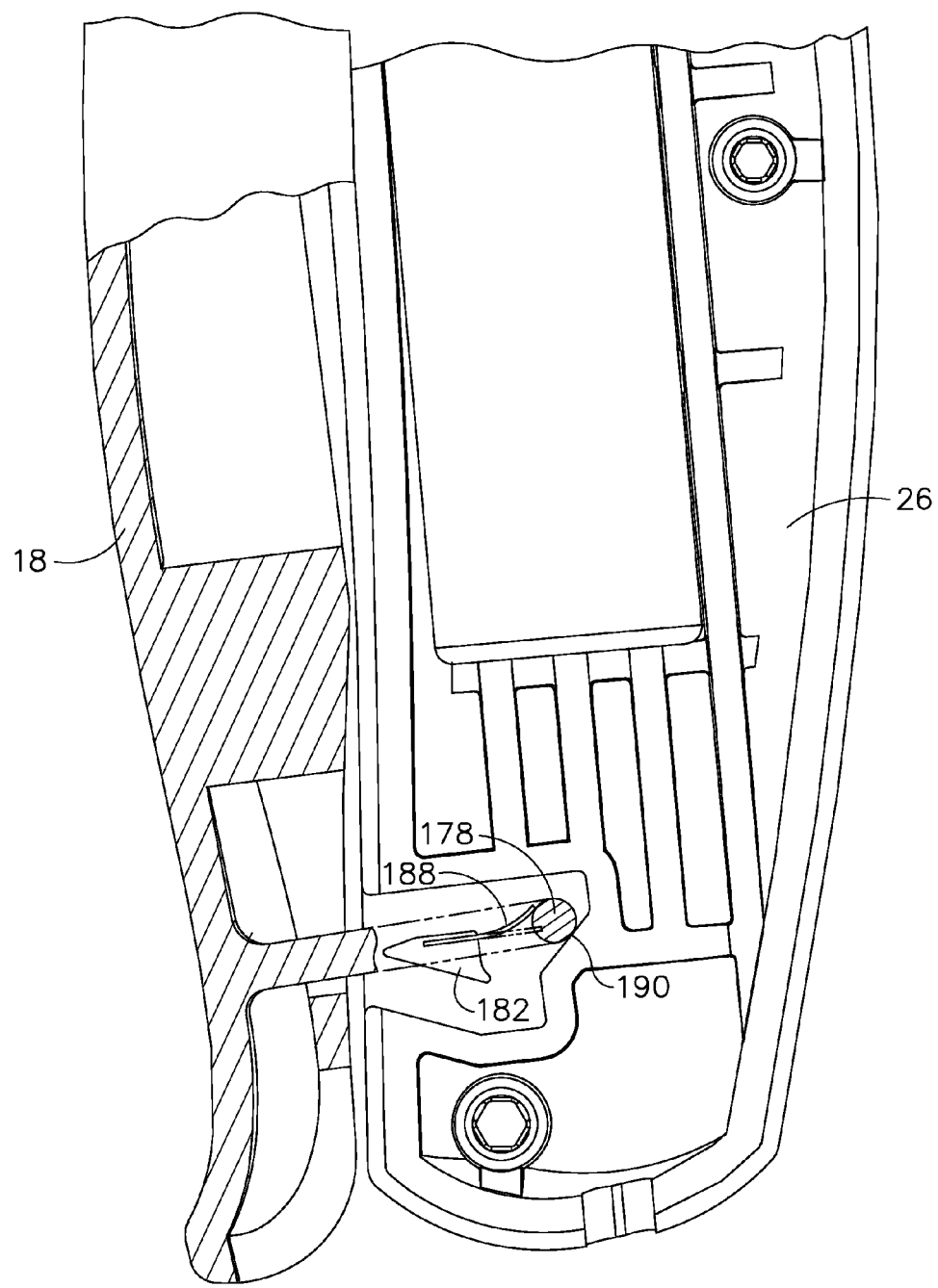
Figure 21:
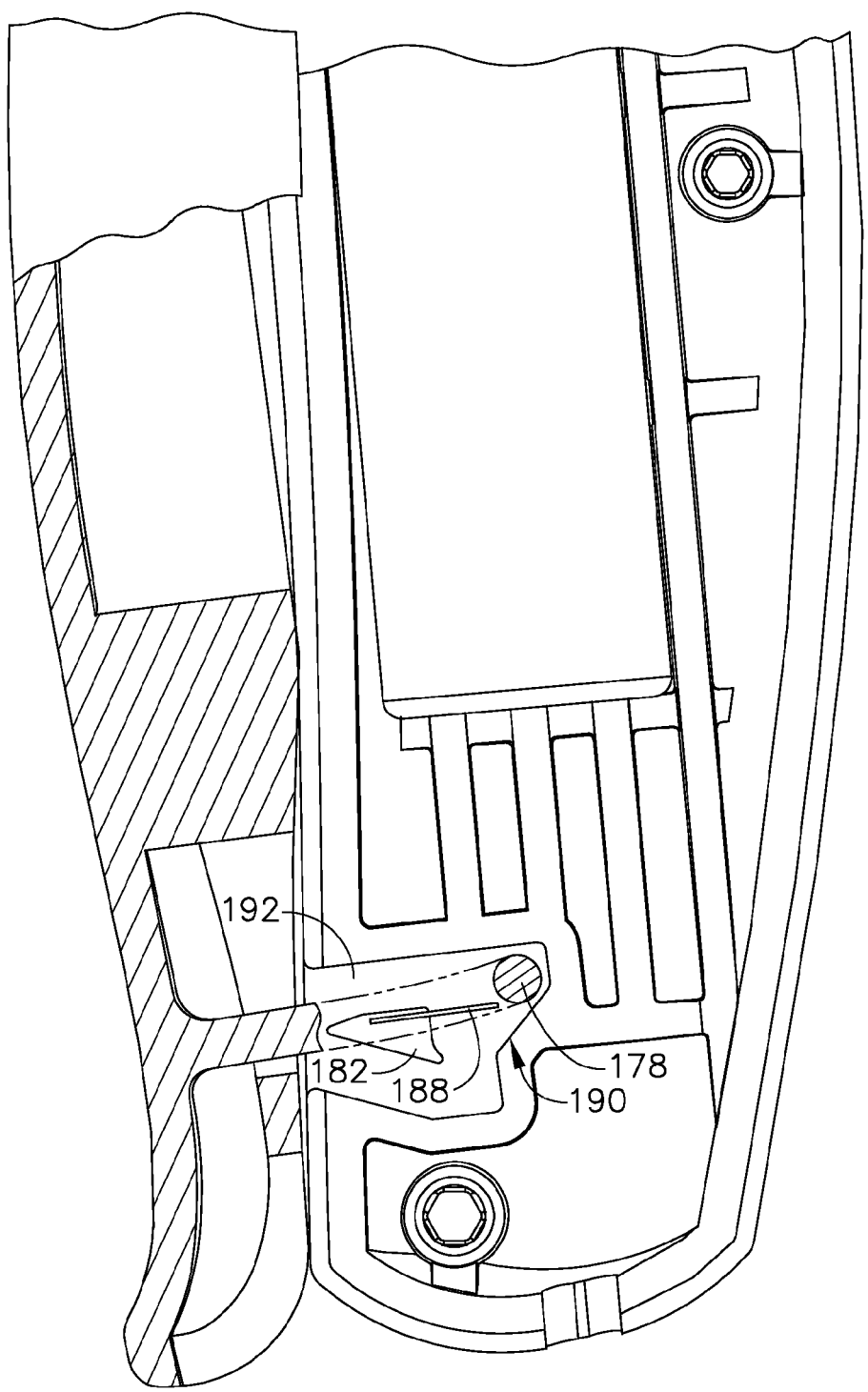
Figure 22:
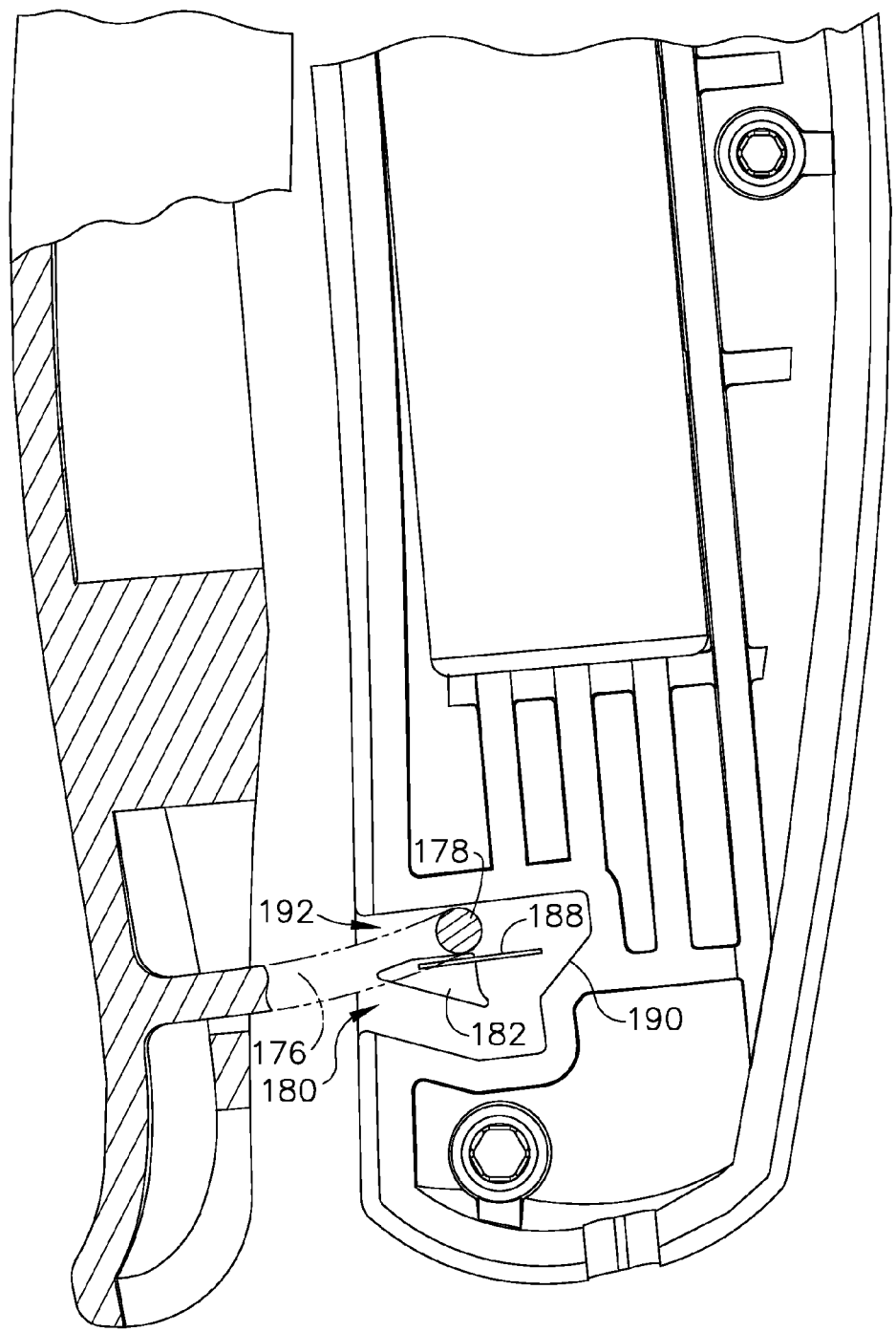
Figure 25:
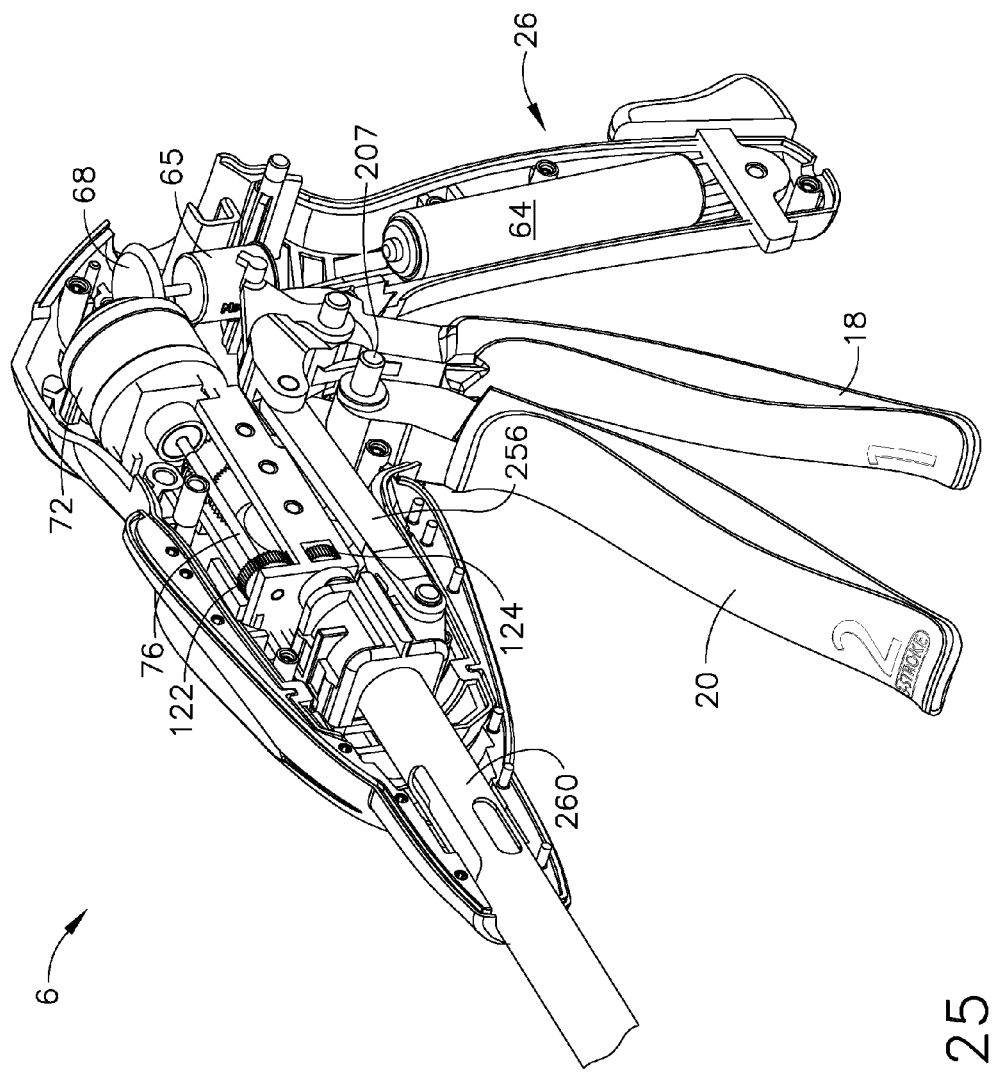
Figure 26:
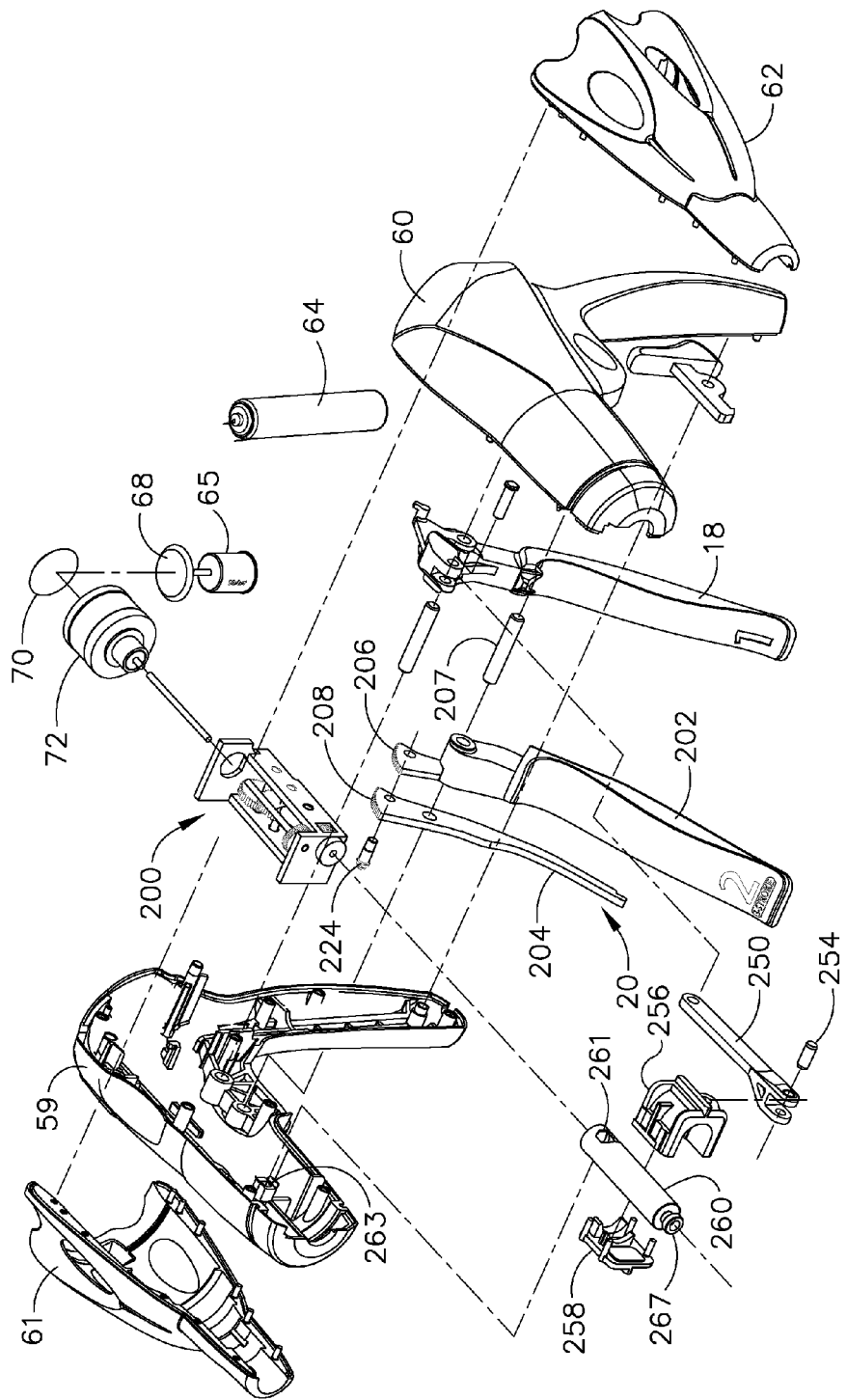
Figure 27:
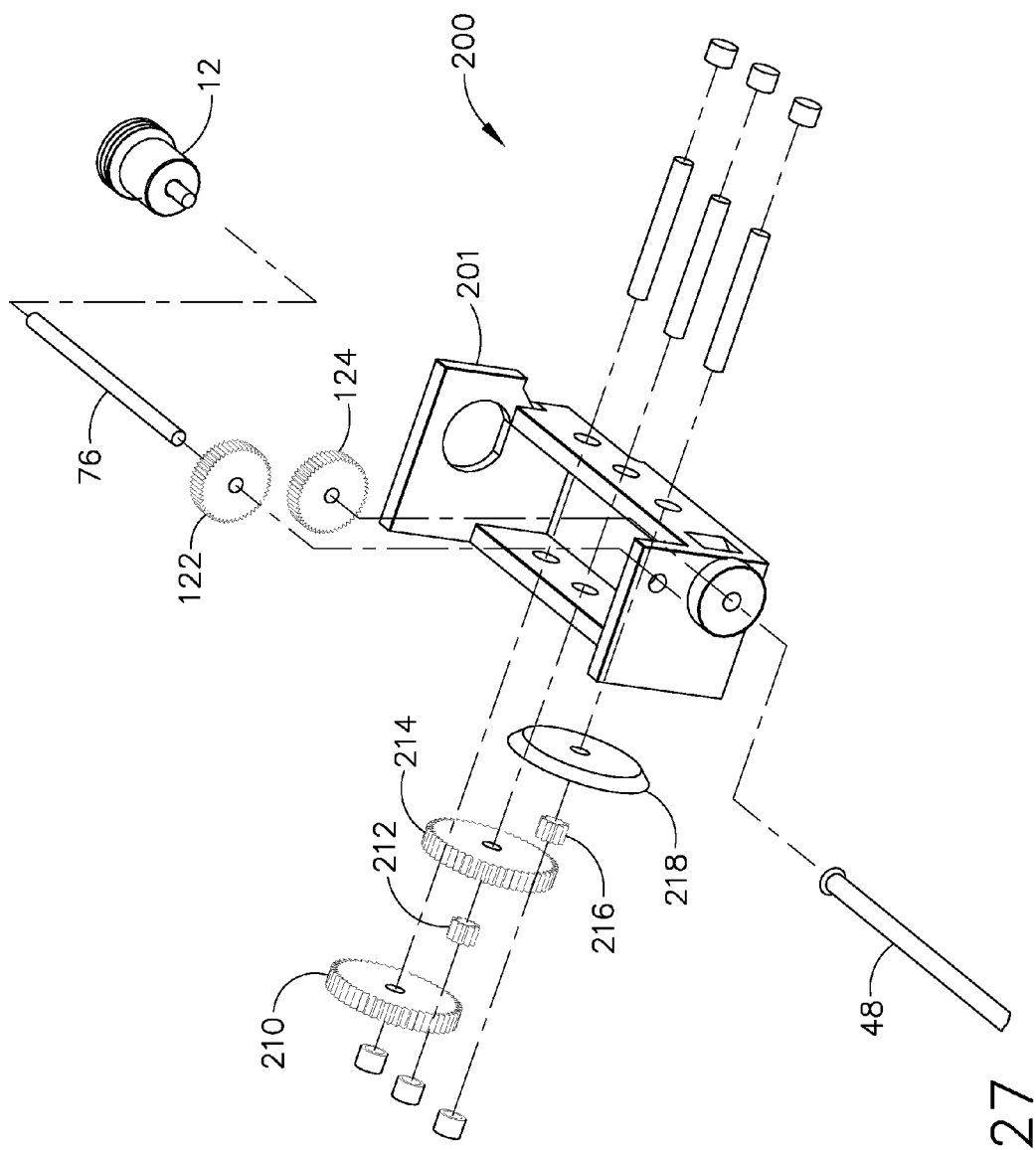
Figure 28:
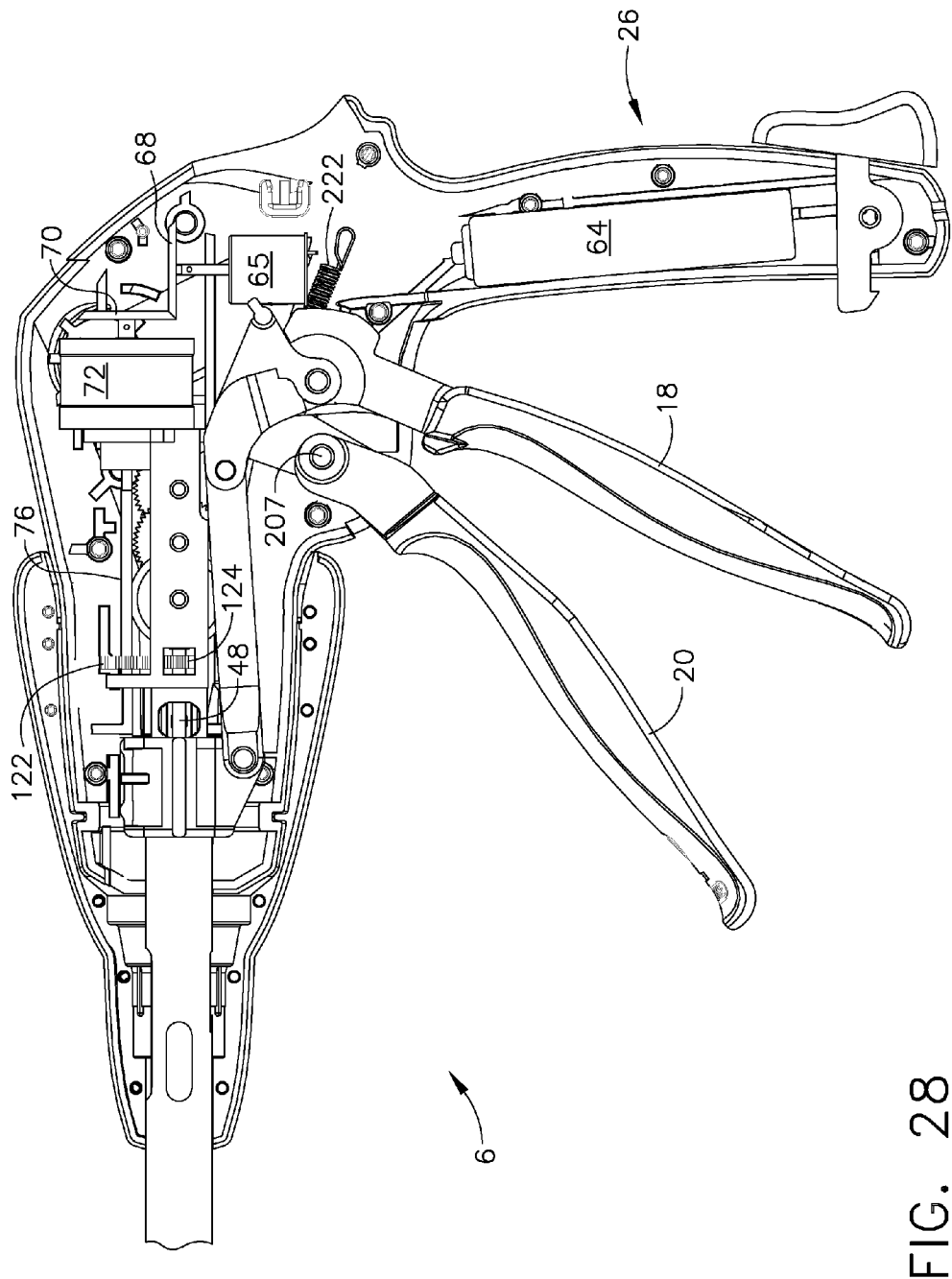
Figure 29:
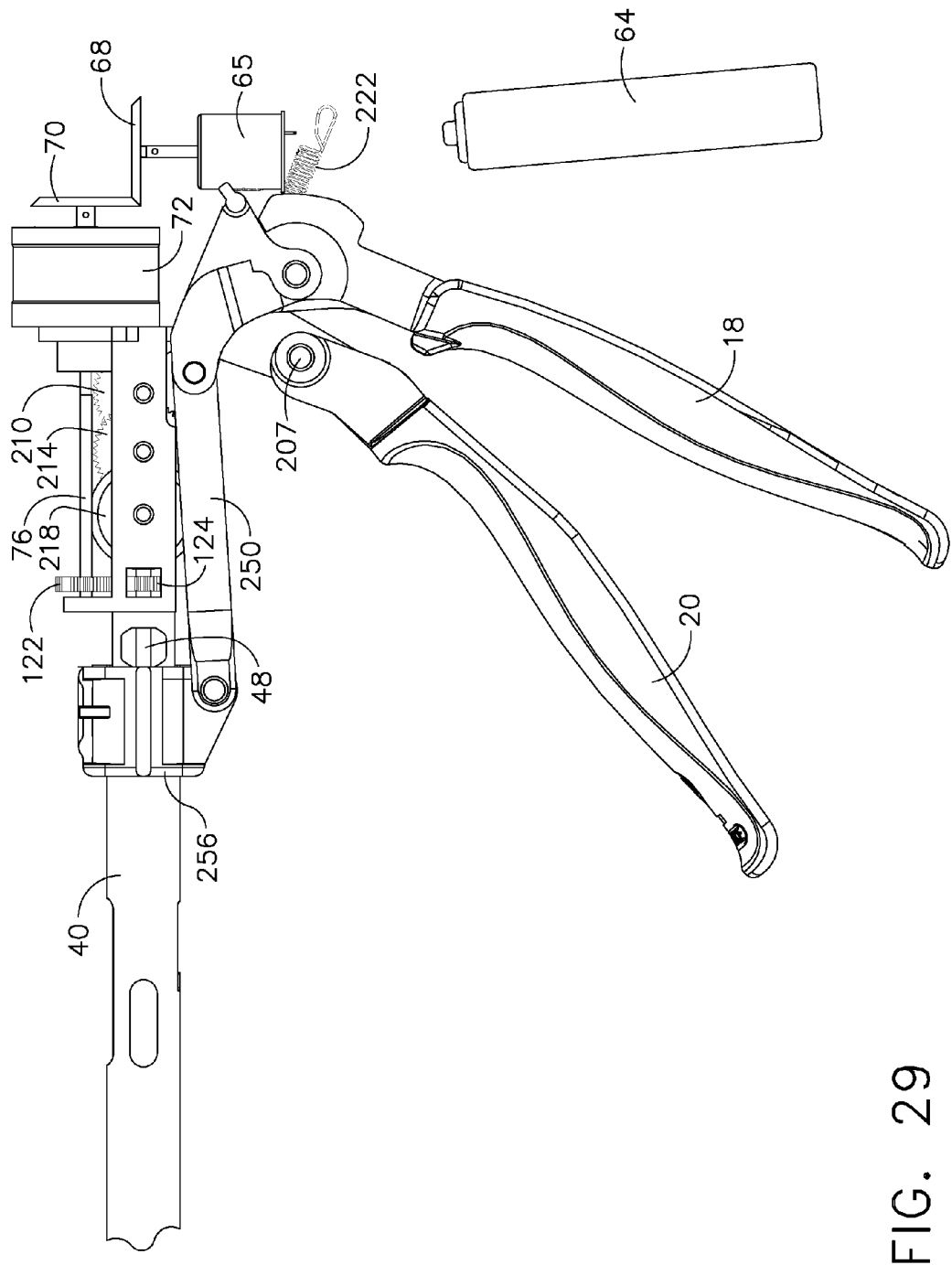
Figure 30:
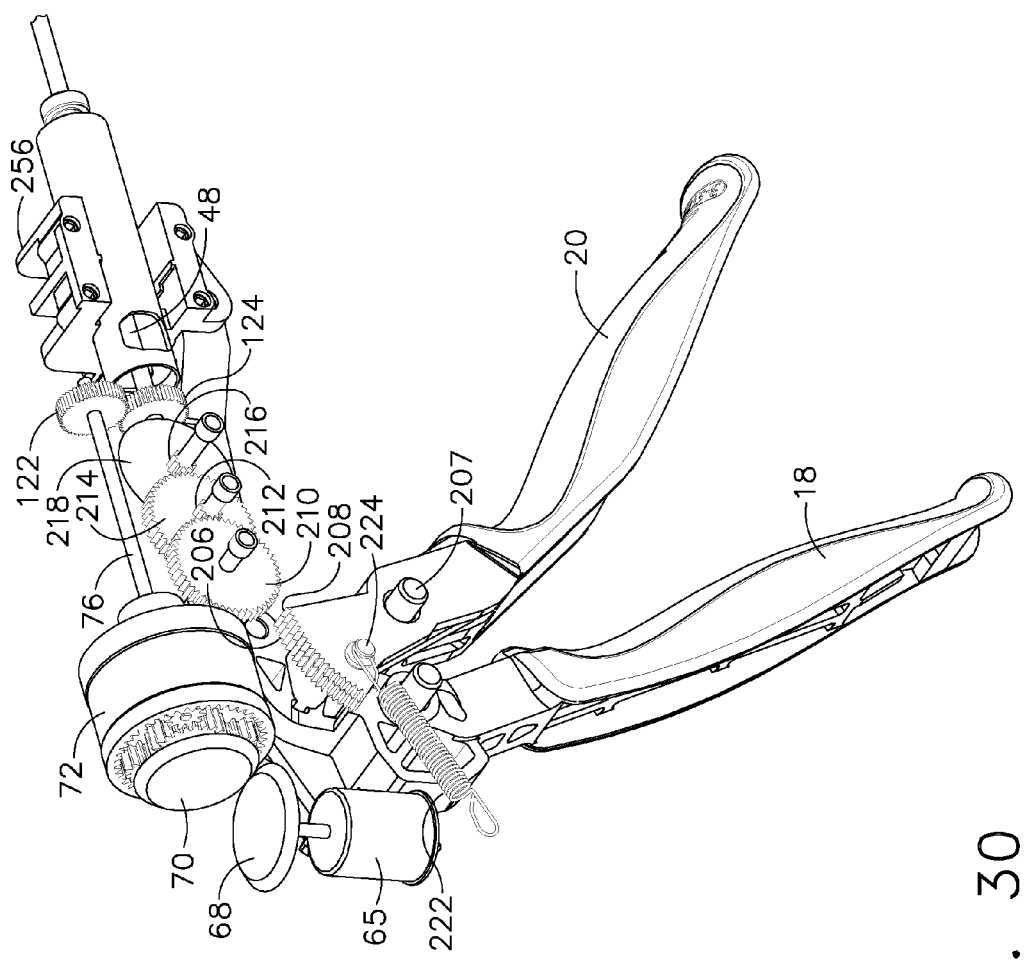
Figure 31:
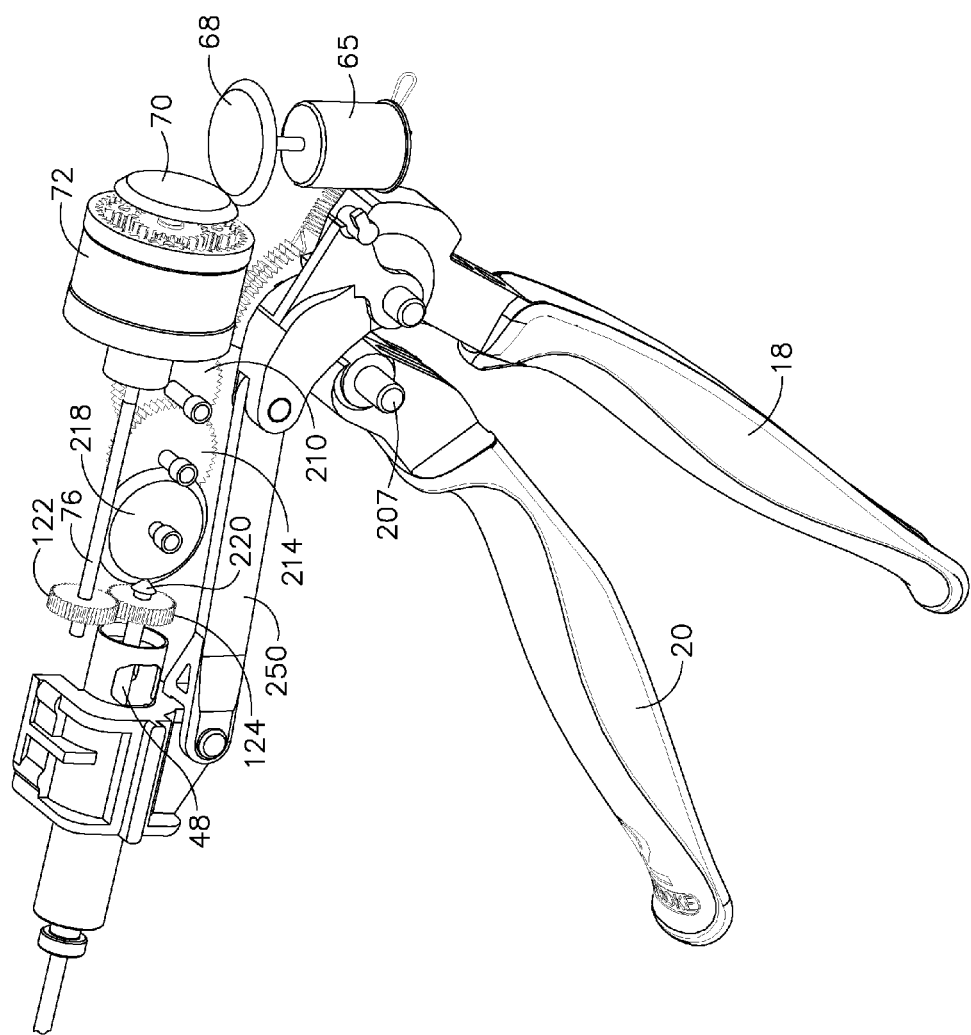

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22.

FIGS. 23A-B show a universal joint ("u-joint") 195. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist according to another embodiment of the present invention. The embodiment of FIGS. 25-31 is similar to that of FIGS. 6-10 except that instead of the helical gear drum 80, the embodiment of FIGS. 23-28 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximate end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 23-32 is another power assist, motorized instrument 10 that provides feedback to the user regarding the loading force experienced by the cutting instrument.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 207 may be inserted through openings in the firing trigger pieces 202, 204 and may be the point about which the firing trigger 20 rotates. In addition, a spring 222 may bias the firing trigger 20 to rotate in a CCW direction. The spring 222 may have a distal end connected to a pin 224 that is connected to the pieces 202, 204 of the firing trigger 20. The proximate end of the spring 222 may be connected to one of the handle exterior lower side pieces 59, 60.

In the illustrated embodiment, both the main body portion 202 and the stiffening portion 204 includes gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 68, 70 to rotate, which causes the planetary gear 72 to rotate, which causes, via the drive shaft 76, the ring gear 122 to rotate. The ring gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate CCW when the motor 65 provides forward drive for the end effector 12 (and to rotate CCW when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate CCW, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife/sled driving member 32) and the end of retraction operation (full retraction of the knife/sled driving member 32). A similar circuit to that described above in connection with FIG. 11 may be used to appropriately power the motor 65.

FIGS. 32-36 illustrate a two-stroke, motorized surgical cutting and fastening instrument 10 with power assist according to another embodiment. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the CW direction. The upper portion 230 may also include a lower arm 234 that contacts an upper surface of the lower portion 228 of the firing trigger 20 such that when the upper portion 230 is caused to rotate CW the lower portion 228 also rotates CW, and when the lower portion 228 rotates CCW the upper portion 230 also rotates CCW. Similarly, the lower portion 228 includes a rotational stop 238 that engages a lower shoulder of the upper portion 230. In that way, when the upper portion 230 is caused to rotate CCW the lower portion 228 also rotates CCW, and when the lower portion 228 rotates CW the upper portion 230 also rotates CW.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include a reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
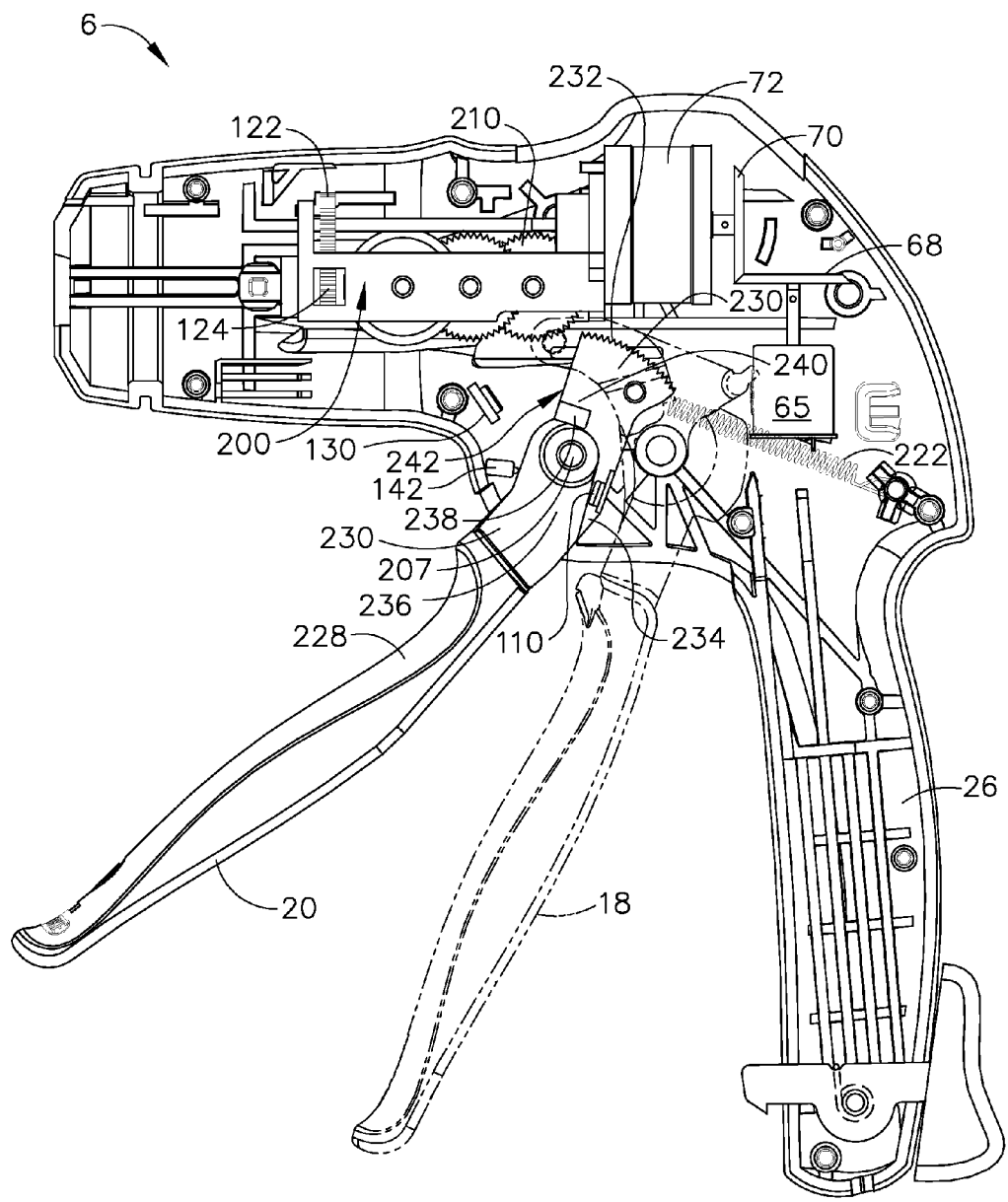
Figure 33:
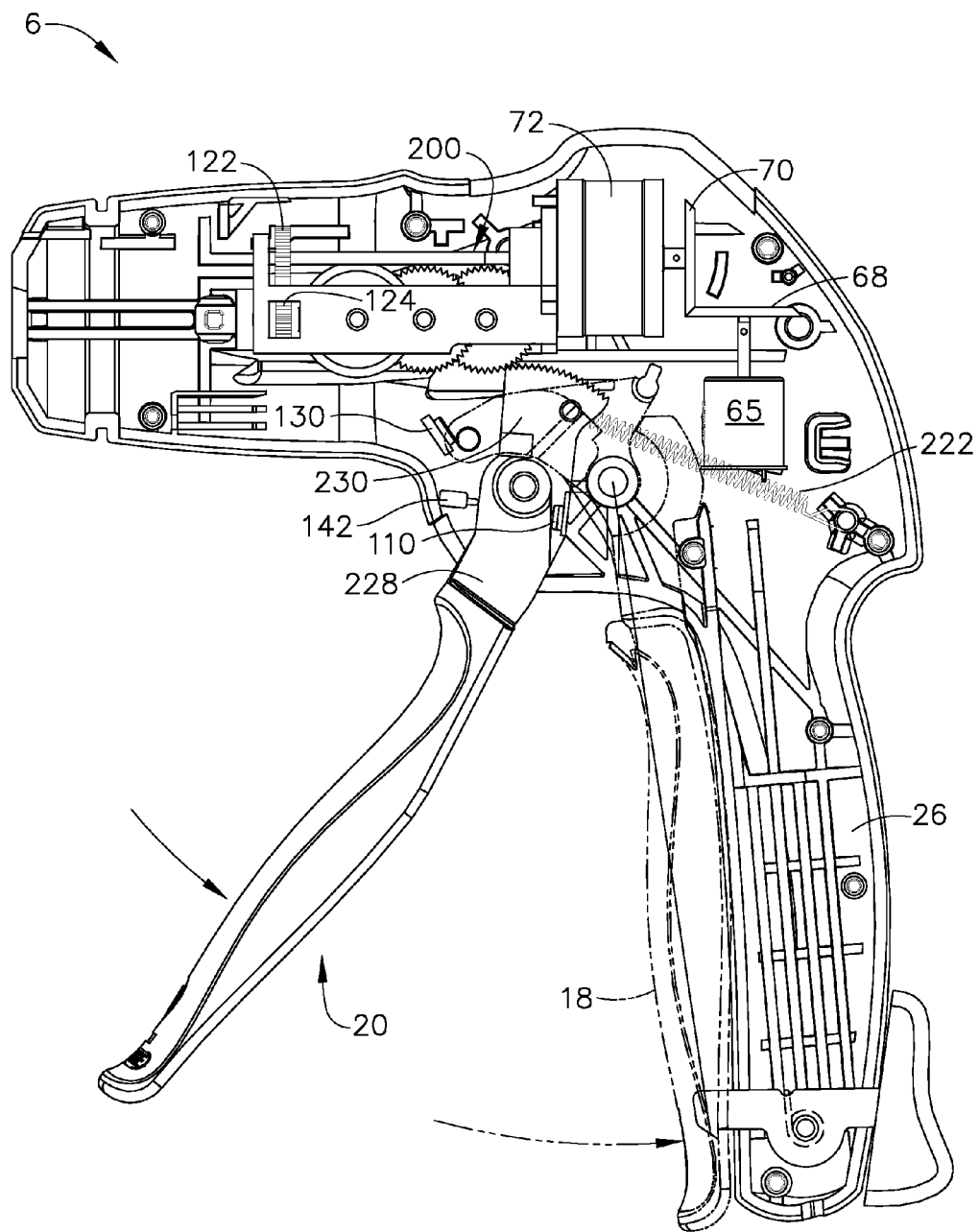
Figure 34:
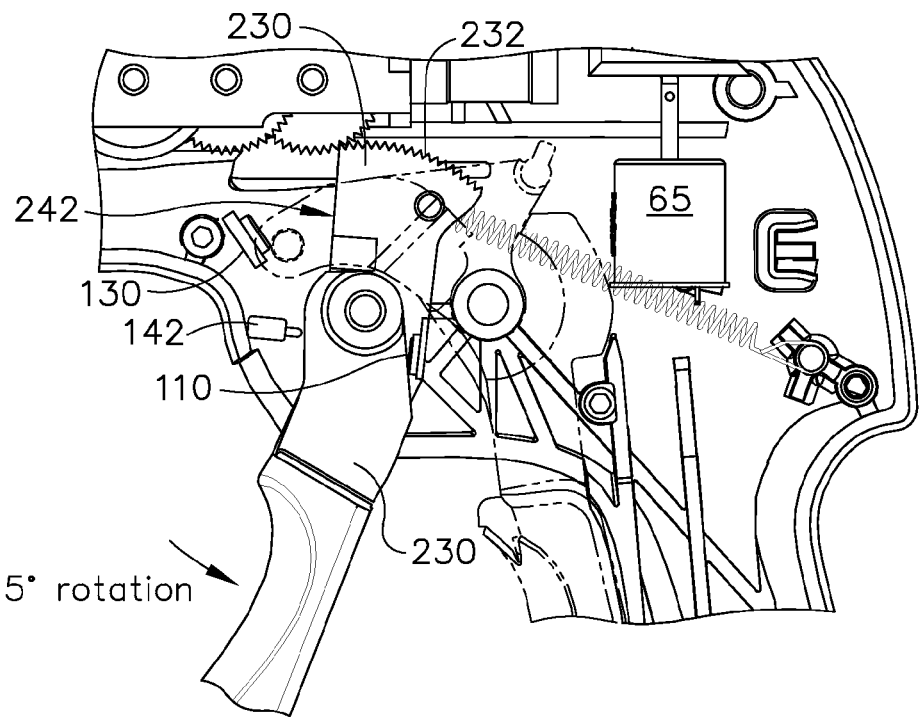
Figure 35:
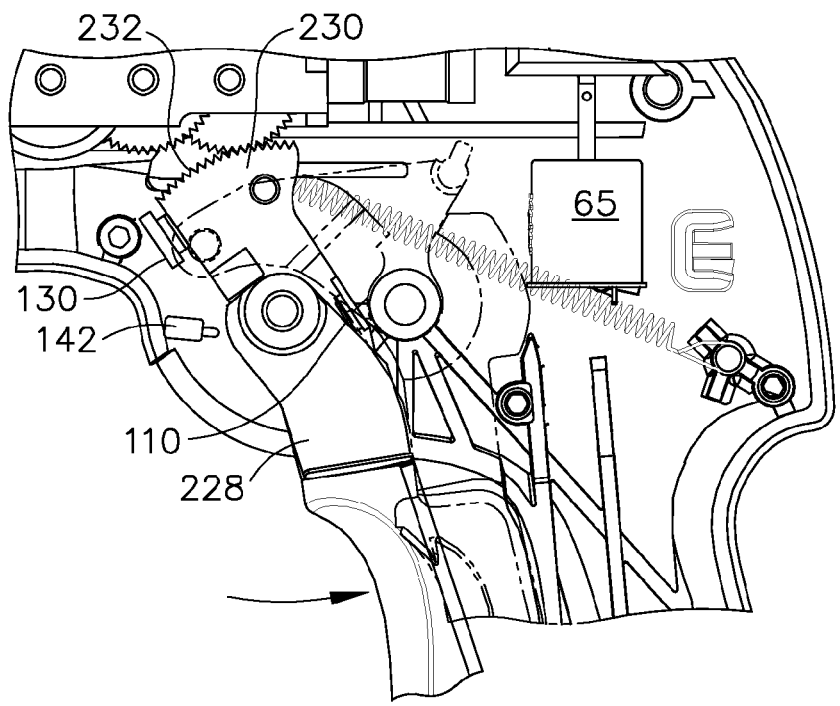
Figure 36:
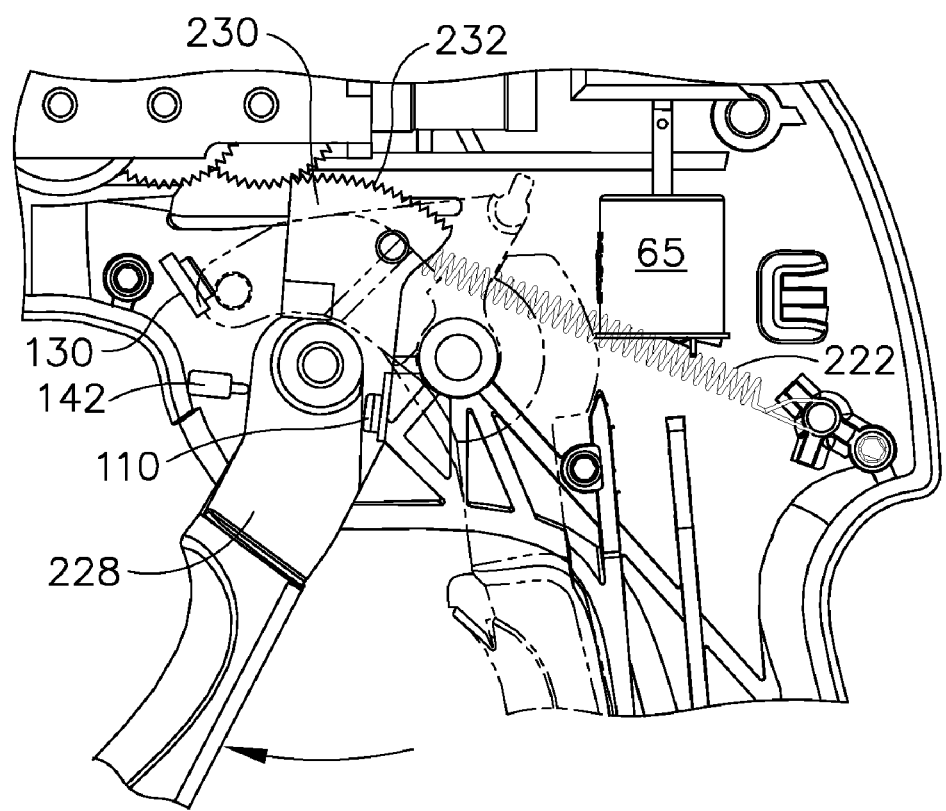

In operation, when an operator retracts the closure trigger 18 into the locked position, the firing trigger 20 is retracted slightly (through mechanisms known in the art, including U.S. Pat. No. 6,978,921 to Frederick Shelton, IV et. al and U.S. Pat. No. 6,905,057 to Jeffery S. Swayze et. al, which are incorporated herein by reference) so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (i.e., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 232 is caused to rotate CCW, which causes the lower portion 228 to also rotate CCW.

When the knife 32 is fully deployed (i.e., at the end of the cutting stroke), the front face 242 of the upper portion 230 trips the reverse motor sensor 130, which sends a signal to the motor 65 to reverse rotational directional. This causes the main drive shaft assembly to reverse rotational direction to retract the knife 32. Reverse rotation of the main drive shaft assembly causes the gears 210-220 in the gear box assembly to reverse direction, which causes the upper portion 230 of the firing trigger 20 to rotate CW, which causes the lower portion 228 of the firing trigger 20 to rotate CW until the lower portion 228 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate CCW, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor, gear drive train, and end effector) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments of the present invention, the user may be provided with tactile feedback regarding the position of the knife 32 in the end effector, but without having the firing trigger 20 geared into the gear drive train. FIGS. 37-40 illustrate a motorized surgical cutting and fastening instrument with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIG. 32-36, however, the upper portion 230 does not have a gear portion that mates with part of the gear drive train. Instead, the instrument includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
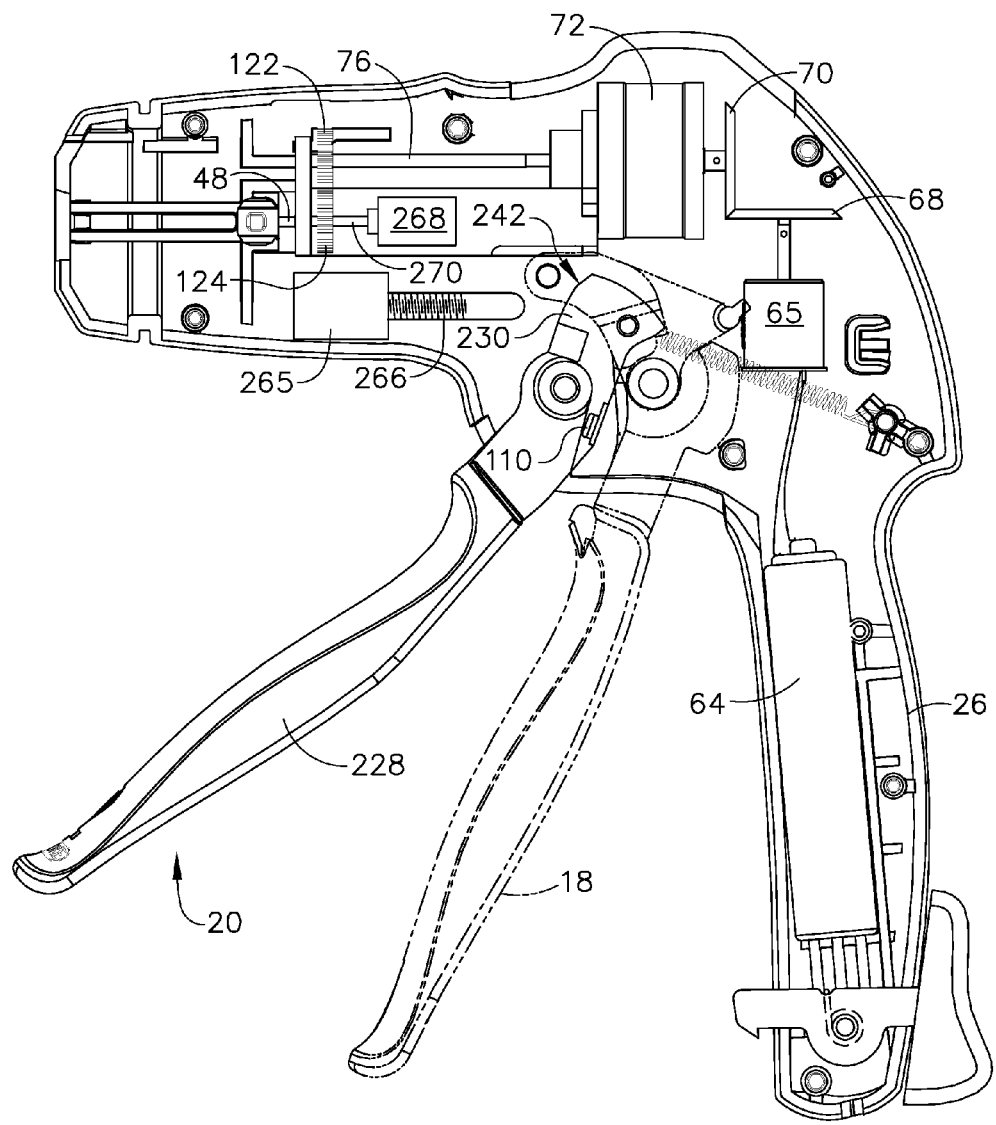
Figure 38:
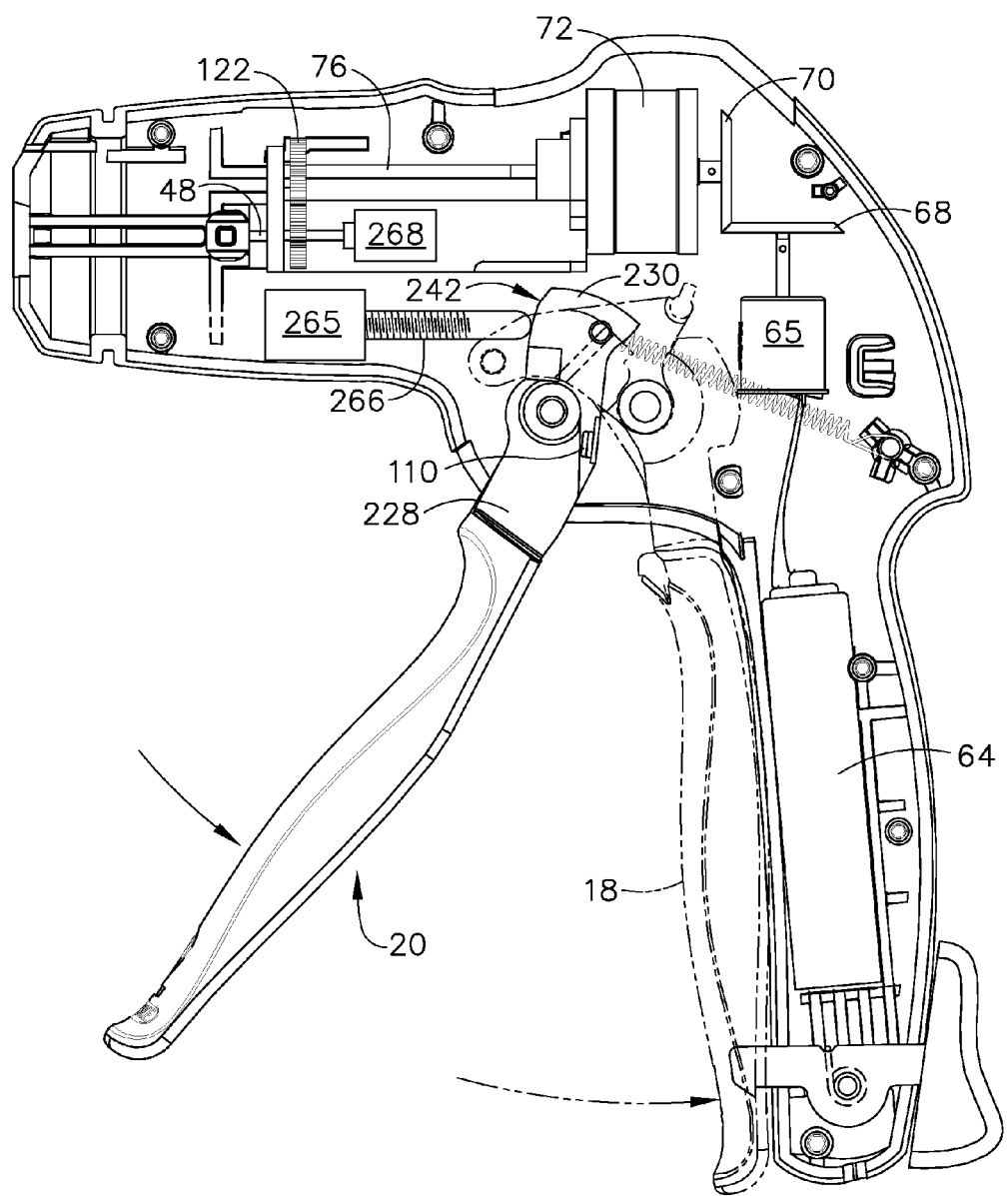
Figure 39:
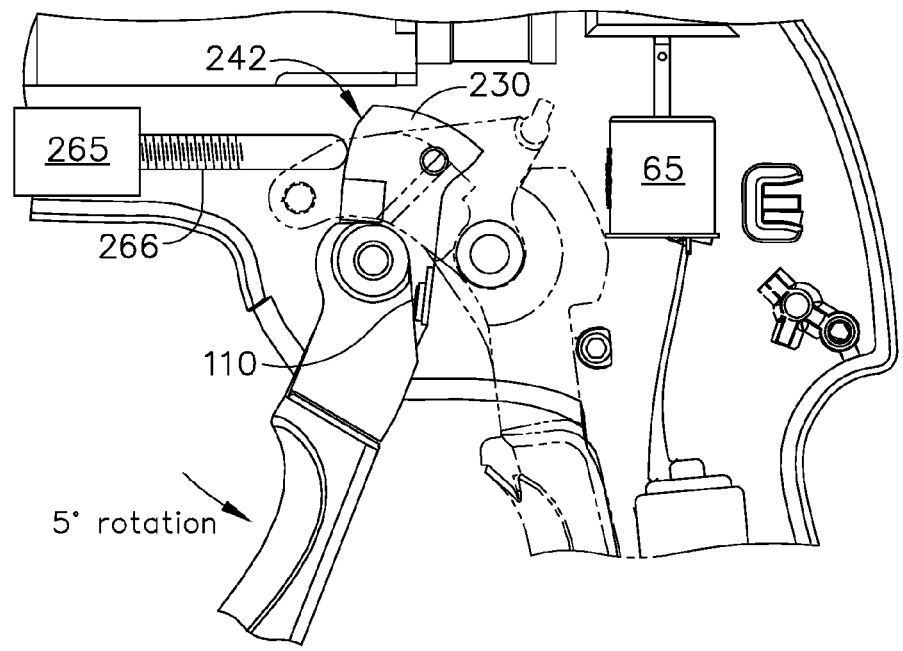
Figure 40:
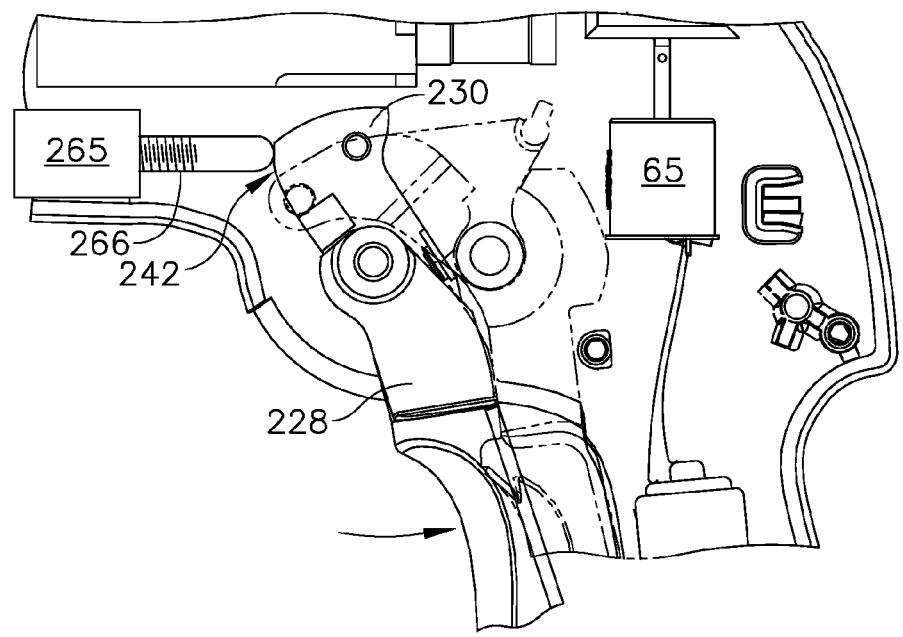

In operation, as shown in FIG. 37, when the closure trigger 18 is not locked into the clamped position, the firing trigger 20 rotated away from the pistol grip portion 26 of the handle 6 such that the front face 242 of the upper portion 230 of the firing trigger 20 is not in contact with the proximate end of the threaded rod 266. When the operator retracts the closure trigger 18 and locks it in the clamped position, the firing trigger 20 rotates slightly towards the closure trigger 20 so that the operator can grasp the firing trigger 20, as shown in FIG. 38. In this position, the front face 242 of the upper portion 230 contacts the proximate end of the threaded rod 266.

As the user then retracts the firing trigger 20, after an initial rotational amount (e.g., 5 degrees of rotation) the run motor sensor 110 may be activated such that, as explained above, the sensor 110 sends a signal to the motor 65 to cause it to rotate at a forward speed proportional to the amount of retraction force applied by the operator to the firing trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to caused the second motor 265 to rotate, which causes the threaded rod 266 to retract into the motor 265. This allows the upper portion 230 of the firing trigger 20 to rotate CCW, which allows the lower portion 228 of the firing trigger to also rotate CCW. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (i.e., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate CW, which causes the lower portion 228 to rotate CW. In that way, the operator may experience a CW force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

The various embodiments of the present invention have been described above in connection with cutting-type surgical instruments. It should be noted, however, that in other embodiments, the inventive surgical instrument disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A surgical cutting and fastening instrument comprising:
an end effector comprising:
an elongate channel;
a clamping member pivotably connected to the channel; and a moveable cutting instrument for traversing the channel to cut an object clamped in the end effector by the clamping member when the clamping member is in a clamped position;
a main drive shaft assembly for actuating the cutting instrument in the end effector;
a gear drive train connected to the main drive shaft assembly;
a motor for actuating the gear drive train;
a closure trigger;
a mechanical closure system connected to the closure trigger and to the clamping member for causing the clamping member to pivot to the clamped position when the closure trigger is retracted; and
a firing trigger separate from the closure trigger for actuating the motor when the firing trigger is retracted to cause the cutting instrument to traverse the channel such that a loading force on the firing trigger when retracted is related to another loading force experienced by the cutting instrument as the cutting instrument cuts the object clamped in the end effector.

2. The surgical cutting and fastening instrument of claim 1, wherein the mechanical closure system comprises:
a bracket connected to the closure trigger; and
a closure tube assembly having a distal end connected to the clamping member and a proximate end seated in the bracket.

3. The surgical cutting and fastening instrument of claim 2, wherein retraction of the closure trigger causes the closure tube assembly to slide proximately such that the clamping member rotates from an open position to the clamped position.

4. The surgical cutting and fastening instrument of claim 3, wherein the end effector includes a staple cartridge seated in the elongate channel and the clamping member comprises an anvil.

5. The surgical cutting and fastening instrument of claim 3, further comprising a locking mechanism for locking the closure trigger when retracted.

6. The surgical cutting and fastening instrument of claim 3, wherein the end effector further comprises a helical drive screw, such that forward rotation of the helical drive screw causes the cutting instrument to undertake the cutting stroke by traveling distally along the channel, and reverse rotation of the helical drive screw causes the cutting instrument to retract by traveling proximately along the channel.

7. The surgical cutting and fastening instrument of claim 3, wherein the main drive shaft assembly includes articulation means for articulating the end effector.

8. The surgical cutting and fastening instrument of claim 3, wherein the firing trigger is geared into the gear drive train.

9. The surgical cutting and fastening instrument of claim 3, further comprising a tactile position feedback system for applying force to the firing trigger such that the position of the firing trigger is related to the position of the cutting instrument in the end effector.

10. The surgical cutting and fastening instrument of claim 3, further comprising a run motor sensor for sensing retracting of the firing trigger, wherein, when retraction of the firing trigger is sensed by the run motor sensor, the motor is signaled to forward rotate to cause cutting of the object positioned in the end effector by the cutting instrument.

11. The surgical cutting and fastening instrument of claim 10, wherein the run motor sensor comprises a proportional switch such that the rate of rotation of the motor is proportional to the retraction force applied to the firing trigger.

12. The surgical cutting and fastening instrument of claim 11, further comprising:
a reverse motor sensor for sensing a condition indicative of an end of a cutting stroke by the cutting instrument; and
a stop motor sensor for sensing a condition indicative of retraction of the cutting instrument.

13. The surgical cutting and fastening instrument of claim 3, wherein the mechanical closure system further comprises a yoke connecting the closure trigger to the bracket.

14. The surgical cutting and fastening instrument of claim 3, wherein the motor and a battery for powering the motor are disposed in a handle of the instrument.

15. The surgical cutting and fastening instrument of claim 3, wherein the closure tube assembly comprises a proximate closure tube and a distal closure tube, and wherein the main drive shaft assembly is disposed inside the closure tube assembly.

16. The surgical cutting and fastening instrument of claim 15, further comprising a spine tube disposed between the closure tube assembly and the main drive shaft assembly.

17. The surgical cutting and fastening instrument of claim 1, wherein the rotational position of the firing trigger is related to the position of the cutting instrument in the end effector.

18. A surgical cutting and fastening instrument comprising:
an end effector comprising:
an elongate channel;
a clamping member pivotably connected to the channel; and
a moveable cutting instrument for traversing the channel to cut an object clamped in the end effector by the clamping member when the clamping member is in a clamped position;
a main drive shaft assembly for actuating the cutting instrument in the end effector;
a handle comprising:
a gear drive train connected to the main drive shaft assembly;
a motor for actuating the gear drive train;
a closure trigger; and
a firing trigger separate from the closure trigger for actuating the motor when the firing trigger is retracted, wherein a loading force on the firing trigger when retracted is related to another loading force experienced by the cutting instrument; and
a mechanical closure system connected to the closure trigger and to the clamping member for causing the clamping member to pivot to the clamped position when the closure trigger is retracted, wherein the mechanical closure system comprises:
a bracket connected to the closure trigger; and
a closure tube assembly having a distal end connected to the clamping member and a proximate end seated in the bracket.

19. The surgical cutting and fastening instrument of claim 18, wherein retraction of the closure trigger causes the closure tube assembly to slide proximately such that the clamping member rotates from an open position to the clamped position.

20. The surgical cutting and fastening instrument of claim 19, wherein the end effector further comprises a helical drive screw, such that forward rotation of the helical drive screw causes the cutting instrument to undertake the cutting stroke by traveling distally along the channel, and reverse rotation of the helical drive screw causes the cutting instrument to retract by traveling proximately along the channel.

21. The surgical cutting and fastening instrument of claim 18, wherein the rotational position of the firing trigger is related to the position of the cutting instrument in the end effector.

22. A surgical cutting and fastening instrument comprising:
- an end effector comprising:
  - an elongate channel;
  - a clamping member pivotably connected to the channel; and
  - a moveable cutting instrument for traversing the channel to cut an object clamped in the end effector by the clamping member when the clamping member is in a clamped position;
- a main drive shaft assembly for actuating the cutting instrument in the end effector;
- a gear drive train connected to the main drive shaft assembly;
- a motor for actuating the gear drive train;
- a closure trigger;
- means for causing the clamping member to pivot to the clamped position when the closure trigger is retracted; and
- a firing trigger separate from the closure trigger for actuating the motor when the firing trigger is retracted, wherein the rotational position of the firing trigger is related to the position of the cutting instrument in the end effector.

* * * * *